United States Patent [19]
Kubota et al.

[11] Patent Number: 5,599,770
[45] Date of Patent: Feb. 4, 1997

[54] HERBICIDAL COMPOSITION CONTAINING 2-BENZYLOXYPYRIMIDINE DERIVATIVES, PROCESSES FOR PRODUCING THE DERIVATIVES AND 2-BENZYLOXYPYRIMIDINE DERIVATIVES

[75] Inventors: Yoshikazu Kubota; Hisashi Kanno; Tsutomu Sato; Masato Arahira, all of Iwaki, Japan

[73] Assignee: Kureha Kagaku Kogyo Kabushiki Kaisha, Japan

[21] Appl. No.: 493,048

[22] Filed: Jun. 21, 1995

[30] Foreign Application Priority Data

Jul. 15, 1994 [JP] Japan .................... 6-186707

[51] Int. Cl.⁶ .............. C07D 239/34; C07D 239/52; C07D 239/60; A01N 43/54
[52] U.S. Cl. .............. 504/242; 504/243; 544/301; 544/302; 544/303; 544/304; 544/311; 544/312; 544/313; 544/314; 544/309; 544/315; 544/316; 544/318
[58] Field of Search .................... 544/301, 302, 544/303, 304, 311, 312, 313, 314, 309, 315, 316, 318; 504/242, 243

[56] References Cited

U.S. PATENT DOCUMENTS

| | | | |
|---|---|---|---|
| 4,941,910 | 7/1990 | Muller et al. | 504/243 |
| 5,139,563 | 8/1992 | Astles et al. | 504/243 |
| 5,238,907 | 8/1993 | Kruger et al. | 504/243 |
| 5,401,711 | 3/1995 | Sato et al. | 504/243 |

FOREIGN PATENT DOCUMENTS

| | | |
|---|---|---|
| 0249708 | 12/1987 | European Pat. Off. . |
| 0398692 | 11/1990 | European Pat. Off. . |
| 2360581 | 3/1978 | France . |
| WO92/19603 | 11/1992 | WIPO . |

OTHER PUBLICATIONS

Patent Abstracts of Japan, vol. 12, No. 22 (C–470) (2869) 22 Jan. 1988.
Chemical Abstracts, vol. 86, No. 5, 31 Jan. 1977, Abstract No. 25844s.
J. Chem. Soc., 1965, 5542–5551—Brown et al., "The Dimroth Rearrangement. Part IV".
J. Chem. Soc., 1975, 1798–1802—Kaspersen et al., "Unconventional Nucleotide Analogues. Part XIV".
J. Chem. Soc., 1959, 525–530—Hunt et al., "Pyrimidines. Part X".

*Primary Examiner*—John M. Ford
*Attorney, Agent, or Firm*—Parkhurst, Wendel & Burr, L.L.P.

[57] ABSTRACT

A herbicidal composition comprising a herbicidally effective amount of a 2-benzyloxypyrimidine derivative represented by the formula (I):

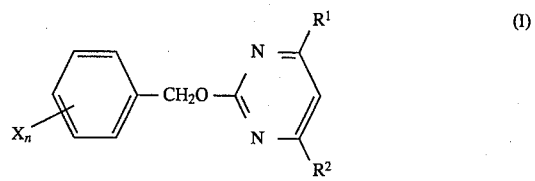

wherein $R^1$ and $R^2$ are each independently H, a halogen, hydroxyl, $C_1$–$C_4$ alkyl, $C_1$–$C_4$ haloalkyl, $C_3$–$C_5$ alkenyl, $C_3$–$C_5$ alkynyl, $C_1$–$C_4$ alkoxy, $C_1$–$C_4$ haloalkoxy, $C_3$–$C_5$ alkenyloxy, $C_3$–$C_5$ alkynyloxy, $C_1$–$C_4$ alkylthio, or phenyl;

n is an integer of 0 to 5; and each X which may be identical or different if n is greater than 1, is a halogen, $C_1$–$C_4$ alkyl, $C_1$–$C_4$ haloalkyl, $C_1$–$C_4$ alkoxy, $C_1$–$C_4$ alkylthio, $C_7$–$C_9$ aralkyloxy, phenyl, hydroxymethyl, hydroxycarbonyl, $C_1$–$C_4$ alkoxycarbonyl, or nitro, and an adjuvant.

4 Claims, No Drawings

HERBICIDAL COMPOSITION CONTAINING 2-BENZYLOXYPYRIMIDINE DERIVATIVES, PROCESSES FOR PRODUCING THE DERIVATIVES AND 2-BENZYLOXYPYRIMIDINE DERIVATIVES

BACKGROUND OF THE INVENTION

The present invention relates to a herbicidal composition containing a 2-benzyloxypyrimidine derivative, processes for the production of the derivative as well as a novel 2-benzyloxypyrimidine derivative.

Among 2-benzyloxypyrimidine derivatives, three compounds, that is, 2-benzyloxypyrimidine, 2-benzyloxy-4-ethoxypyrimidine and 2-benzyloxy-4,6-dimethylpyrimidine are respectively described in the following documents: 2-benzyloxypyrimidine: J. Chem. Soc., 1965, 5542–5549; 2-benzyloxy-4-ethoxypyrimidine: J. Chem. Soc., Perkin Trans. 1, 1975, 1798–1802; and 2-benzyloxy-4,6-dimethylpyrimidine: J. Chem. Soc., 1959, 525–530.

However, there hasn't been any known document which describes herbicidal activity of 2-benzyloxypyrimidine derivatives including these three compounds.

The present inventors have found the 2-benzyloxypyrimidine derivatives having herbicidal activity and, after having studied herbicidal properties thereof and processes for the production thereof, have attained the present invention.

SUMMARY OF THE INVENTION

In a first aspect of the invention, it is provided a herbicidal composition comprising a herbicidally effective amount of a 2-benzyloxypyrimidine derivative represented by the formula (I):

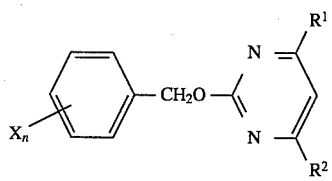

wherein
$R^1$ and $R^2$ are each independently H, a halogen, hydroxyl, $C_1$–$C_4$ alkyl, $C_1$–$C_4$ haloalkyl, $C_3$–$C_5$ alkenyl, $C_3$–$C_5$ alkynyl, $C_1$–$C_4$ alkoxy, $C_1$–$C_4$ haloalkoxy, $C_3$–$C_5$ alkenyloxy, $C_3$–$C_5$ alkynyloxy, $C_1$–$C_4$ alkylthio, or phenyl;

n is an integer of 0 to 5; and each X which may be identical or different if n is greater than 1, is a halogen, $C_1$–$C_4$ alkyl, $C_1$–$C_4$ haloalkyl, $C_1$–$C_4$ alkoxy, $C_1$–$C_4$ alkylthio, $C_7$–$C_9$ aralkyloxy, phenyl, hydroxymethyl, hydroxycarbonyl, $C_1$–$C_4$ alkoxycarbonyl, or nitro, and an adjuvant.

In a second aspect of the invention, it is provided a process for producing a 2-benzyloxypyrimidine derivative of the formula (I):

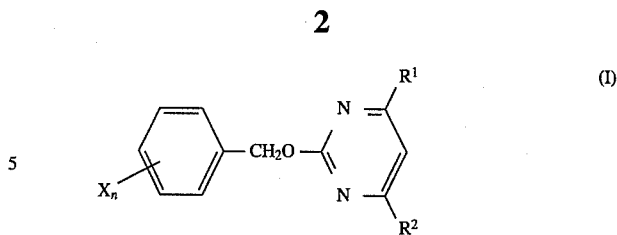

wherein
$R^1$, $R^2$, X, and n are as defined above, comprising reacting a compound of the formula (II):

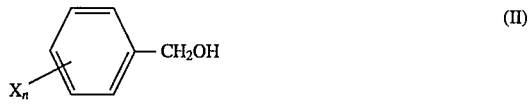

wherein
X and n are as defined above, with a compound of the formula (III):

wherein
$R^1$ and $R^2$ are as defined above; and

Z is a halogen, $C_1$–$C_4$ alkylsulfonyl, $C_7$–$C_9$ aralkylsulfonyl, or arylsulfonyl, in the presence of a basic compound, with a proviso that the case in which 2-benzyloxy-4,6-dimethylpyrimidine is prepared by starting with 2-chloro-4,6-dimethylpyrimidine and benzyl alcohol is excluded.

In a third aspect of the invention, it is provided a process for producing a 2-benzyloxypyrimidine derivative of the formula (I-b):

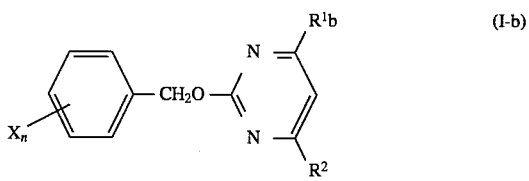

wherein
$R^1b$ is $C_1$–$C_4$ alkoxy, $C_1$–$C_4$ haloalkoxy, $C_3$–$C_5$ alkenyloxy, $C_1$–$C_4$ alkylthio, or $C_3$–$C_5$ alkynyloxy;

$R^2$ is H, a halogen, hydroxyl, $C_1$–$C_4$ alkyl, $C_1$–$C_4$ haloalkyl, $C_3$–$C_5$ alkenyl, $C_3$–$C_5$ alkynyl, $C_1$–$C_4$ alkoxy, $C_1$–$C_4$ haloalkoxy, $C_3$–$C_5$ alkenyloxy, $C_3$–$C_5$ alkynyloxy, $C_1$–$C_4$ alkylthio, or phenyl;

n is an integer of 0 to 5, and each X which may be identical or different if n is greater than 1, is a halogen, $C_1$–$C_4$ alkyl, $C_1$–$C_4$ haloalkyl, $C_1$–$C_4$ alkoxy, $C_1$–$C_4$ alkylthio, $C_7$–$C_9$ aralkyloxy, phenyl, hydroxymethyl, hydroxycarbonyl, $C_1$–$C_4$ alkoxycarbonyl, or nitro, comprising reacting a 2-benzyloxypyrimidine derivative of the formula (I-a):

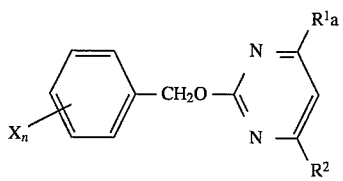

wherein

R¹a is a halogen; and

R², X, and n are as defined above, with an alcohol or alkanethiol to nucleophilically substitute for either one or both of halogens at the positions 4 and 6 on the pyrimidine ring of the 2-benzyloxypyrimidine derivative of the formula (I-a).

In a fourth aspect of the invention, it is provided a 2-benzyloxypyrimidine derivative represented by the formula (I):

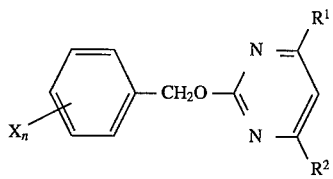

wherein

R¹ and R² are each independently H, a halogen, hydroxyl, $C_1$–$C_4$ alkyl, $C_1$–$C_4$ haloalkyl, $C_3$–$C_5$ alkenyl, $C_3$–$C_5$ alkynyl, $C_1$–$C_4$ alkoxy, $C_1$–$C_4$ haloalkoxy, $C_3$–$C_5$ alkenyloxy, $C_3$–$C_5$ alkynyloxy, $C_1$–$C_4$ alkylthio or phenyl;

n is an integer of 0 to 5; and each X which may be identical or different if n is greater than 1, is a halogen, $C_1$–$C_4$ alkyl, $C_1$–$C_4$ haloalkyl, $C_1$–$C_4$ alkoxy, $C_1$–$C_4$ alkylthio, $C_7$–$C_9$ aralkyloxy, phenyl, hydroxymethyl, hydroxycarbonyl, $C_1$–$C_4$ alkoxycarbonyl, or nitro, with a proviso that 2-benzyloxypyrimidine, 2-benzyloxy-4-ethoxypyrimidine and 2-benzyloxy-4,6-dimethylpyrimidine are excluded.

DETAILED DESCRIPTION OF THE INVENTION

The terms "haloalkyl" and "haloalkoxy" used herein mean respectively alkyl and alkoxy in which at least one hydrogen is substituted with a halogen.

R¹ and R² each independently, preferably includes the following atoms and groups:

hydrogen;

a halogen such as chlorine and bromine;

hydroxyl;

$C_1$–$C_4$ alkyl such as methyl (abbreviated as "Me" in the Table 1 (1/15 to 15/15), Table 3 and Table 4 given below. The following substituents are also shown therein by the abbreviations or rational formulae in parentheses), ethyl (Et), 1-methylethyl (i-Pr), propyl (Pr), and butyl;

$C_1$–$C_4$ haloalkyl such as trifluoromethyl ($CF_3$), fluoromethyl, difluoromethyl, and 2,2,2-trifluoroethyl;

$C_3$–$C_5$ alkenyl such as allyl and crotyl;

$C_3$–$C_5$ alkynyl such as 2-propynyl;

$C_1$–$C_4$ alkoxy such as methoxy (OMe), ethoxy (OEt), (1-methylethyl)oxy (O-i-Pr), propoxy (OPr), (2-methylpropyl)oxy (O-i-Bu), (1-methylpropyl)oxy, and butoxy (OBu);

$C_1$–$C_4$ haloalkoxy such as difluoromethoxy ($OCHF_2$), 1,1,2,2-tetrafluoroethoxy, 2,2,2-trifluoroethoxy ($OCH_2CF_3$), 2-fluoroethoxy, 2-bromo-1,1,2-trifluoroethoxy, 2,2,3,3,3-pentafluoropropoxy ($OCH_2C_2F_5$), 1,1,2,3,3,3-hexafluoropropoxy, and 2-chloro-1,1,2-trifluoroethoxy;

$C_3$–$C_5$ alkenyloxy such as allyloxy ($OCH_2CH=CH_2$), (2-methyl-2-propenyl)oxy ($OCH_2C(Me)=CH_2$), crotyloxy ($OCH_2CH=CHMe$), (3-methyl-2-butenyl)oxy ($OCH_2CH=C(Me)_2$), and (3-methyl-3-butenyl)oxy ($OCH_2CH_2C(Me)=CH_2$);

$C_3$–$C_5$ alkynyloxy such as (2-propynyl)oxy ($OCH_2CCH$);

$C_1$–$C_4$ alkylthio such as methylthio (SMe), ethylthio (SEt), and propylthio (SPr); and phenyl (Ph).

More preferably, R¹ and R² each independently represents methyl or methoxy, and at least one of R¹ and R² is methoxy.

X preferably includes the following atoms and groups:

a halogen such as fluorine, chlorine, bromine, and iodine;

$C_1$–$C_4$ alkyl such as methyl (Me), ethyl (Et), 1-methylethyl (i-Pr), and butyl;

$C_1$–$C_4$ haloalkyl such as trifluoromethyl ($CF_3$), fluoromethyl, difluoromethyl, and 2,2,2-trifluoroethyl;

$C_1$–$C_4$ alkoxy such as methoxy (OMe), ethoxy (OEt), (1-methylethyl)oxy, and (1-methylpropyl)oxy;

$C_1$–$C_4$ alkylthio such as methylthio (SMe) and (1-methylethyl)thio;

$C_7$–$C_9$ aralkyloxy such as benzyloxy (OBn), (1-phenylethyl)oxy, (1-phenylpropyl)oxy, and (3-phenylpropyl)oxy;

phenyl;

hydroxymethyl ($CH_2OH$);

hydroxycarbonyl (COOH);

$C_1$–$C_4$ alkoxycarbonyl such as methoxycarbonyl (COOMe), ethoxycarbonyl (COOEt), (1-methylethyl)oxycarbonyl, propoxycarbonyl, and butoxycarbonyl; and nitro ($NO_2$).

More preferably, X is a halogen.

If n is greater than 1, each X may be identical or different. Also preferably, n is an integer of 0 to 3, more preferably 0 to 2.

Z preferably includes the following atoms and groups:

a halogen such as chlorine and bromine;

$C_1$–$C_4$ alkylsulfonyl such as methylsulfonyl and ethylsulfonyl;

$C_7$–$C_9$ aralkylsulfonyl such as benzylsulfonyl; and arylsulfonyl (usually $C_6$–$C_8$) such as phenylsulfonyl and p-tolylsulfonyl.

According to the present invention, solvents are generally used for the production of derivatives represented by the formula (I). Examples of the solvents which may be suitably used are set forth below and, when the preparing process of the present invention is carried out in a solvent, solvents below may be used alone or in combination of two or more:

water;

organic acids such as formic acid, acetic acid, and propionic acid;

aromatic hydrocarbons such as benzene, toluene, xylene, and methylnaphthalene;

aliphatic hydrocarbons such as petroleum ether, pentane, hexane, heptane, and methylcyclohexane;

halogenated hydrocarbons such as methylene chloride, chloroform, carbon tetrachloride, and chlorobenzene;

alcohols such as methanol, ethanol, i-propanol, and t-butanol;

amides such as dimethylformamide, dimethylacetamide, and N-methyl-2-pyrrolidinone;

ethers such as diethyl ether, dimethoxyethane, diisopropyl ether, tetrahydrofuran, diglyme, and dioxane;

ketones such as acetone and methyl ethyl ketone; and others including carbon disulfide, acetonitrile, ethyl acetate, acetic anhydride, pyridine, dimethyl sulfoxide, hexamethylphosphoric amide, and the like.

When the combination of the solvents incapable of forming a homogeneous phase is used, the reaction may suitably be conducted in the presence of a phase transfer catalyst such as a conventional quaternary ammonium salt or crown ether.

Examples of the basic compounds which may be used in the process of the present invention are as follows:

alkaline metal carbonates such as sodium carbonate and potassium carbonate;

alkaline earth metal carbonates such as magnesium carbonate, calcium carbonate, and barium carbonate;

alkaline metal hydroxides such as sodium hydroxide and potassium hydroxide;

alkaline earth metal hydroxides such as magnesium hydroxide and calcium hydroxide;

alkaline earth metal oxides such as magnesium oxide and calcium oxide;

alkaline metals such as lithium, sodium, and potassium as well as alkaline earth metals such as magnesium;

alkaline metal alkoxides such as sodium methoxide, sodium ethoxide, and potassium t-butoxide;

alkaline metal hydrides such as sodium hydride and potassium hydride;

alkaline earth metal hydrides such as calcium hydride;

organic metal compounds such as methyl lithium, ethyl lithium, n-butyl lithium, and phenyl lithium;

organic Grignard reagents such as methylmagnesium iodide, ethylmagnesium bromide, and n-butylmagnesium bromide;

organic metal compounds of alkaline metals and organic copper compounds prepared from Grignard reagents and copper(I) salts;

alkaline metal amides such as lithium diisopropylamide;

ammonium hydroxides which may be unsubstituted or N-substituted with alkyl or aralkyl such as aqueous ammonia, benzyltrimethylammonium hydroxide, and tetramethylammonium hydroxide; and organic amines such as methylamine, ethylamine, n-propylamine, benzylamine, ethanolamine, dimethylamine, benzylmethylamine, dibenzylamine, triethylamine, triethanolamine, and pyridine.

Also, an acid may be used in the present invention for, for example, post-treatment in the production, if necessary. Examples of the acid include inorganic acids such as hydrochloric acid, hydrobromic acid, hydroiodic acid, perchloric acid, and sulfuric acid; organic acids such as formic acid, acetic acid, butyric acid, and p-toluenesulfonic acid; and Lewis acids such as boron trifluoride, aluminum chloride, and zinc chloride.

Examples of 2-benzyloxypyrimidine derivatives of the formula (I) are shown in Table 1 (1/15 to 15/15).

TABLE 1

(1/15)

| No. | Xn and position | | | | | $R^1$ | $R^2$ |
|---|---|---|---|---|---|---|---|
| | 2 | 3 | 4 | 5 | 6 | | |
| I-1 | Cl | H | H | H | H | H | H |
| I-2 | H | Cl | H | H | H | H | H |
| I-3 | H | H | Cl | H | H | H | H |
| I-4 | Cl | H | H | H | H | Me | H |
| I-5 | H | Cl | H | H | H | Me | H |
| I-6 | H | H | Cl | H | H | Me | H |
| I-7 | H | H | H | H | H | Me | H |
| I-8 | Cl | H | H | H | H | Me | Me |
| I-9 | H | Cl | H | H | H | Me | Me |
| I-10 | F | H | H | H | H | Me | Me |
| I-11 | Br | H | H | H | H | Me | Me |
| I-12 | OMe | H | H | H | H | Me | Me |
| I-13 | H | F | H | H | H | Me | Me |
| I-14 | H | Br | H | H | H | Me | Me |
| I-15 | H | OMe | H | H | H | Me | Me |
| I-16 | H | H | Cl | H | H | Me | Me |
| I-17 | H | H | F | H | H | Me | Me |
| I-18 | H | H | Br | H | H | Me | Me |
| I-19 | H | H | OMe | H | H | Me | Me |
| I-20 | H | H | H | H | H | Me | Me |
| I-21 | F | H | F | H | H | Me | O-i-Pr |
| I-22 | Et | H | H | H | H | Me | O-i-Pr |
| I-23 | H | F | F | H | H | Me | O-i-Pr |
| I-24 | H | H | H | H | H | Me | OCH$_2$CF$_3$ |
| I-25 | F | F | H | H | H | OMe | OMe |
| I-26 | Me | Me | OMe | H | H | OMe | OMe |
| I-27 | OMe | OMe | H | H | H | OMe | OMe |
| I-28 | Cl | H | Cl | H | H | OMe | OMe |
| I-29 | F | H | F | H | H | OMe | OMe |
| I-30 | Me | H | Me | H | H | OMe | OMe |
| I-31 | OMe | Me | OMe | H | H | OMe | OMe |
| I-32 | OMe | H | OMe | H | H | OMe | OMe |
| I-33 | Cl | H | H | Cl | H | OMe | OMe |
| I-34 | F | H | H | F | H | OMe | OMe |
| I-35 | Me | H | H | Me | H | OMe | OMe |
| I-36 | OMe | H | H | OMe | H | OMe | OMe |
| I-37 | Cl | H | H | H | Cl | OMe | OMe |
| I-38 | F | H | H | H | F | OMe | OMe |
| I-39 | OEt | H | H | H | H | OMe | OMe |
| I-40 | Cl | H | H | H | F | OMe | OMe |
| I-41 | CF$_3$ | H | H | H | H | OMe | OMe |
| I-42 | OMe | H | H | H | H | OMe | OMe |
| I-43 | I | H | H | H | H | OMe | OMe |
| I-44 | H | OMe | OMe | OMe | H | OMe | OMe |
| I-45 | H | Cl | Cl | H | H | OMe | OMe |
| I-46 | H | F | F | H | H | OMe | OMe |
| I-47 | H | Me | Me | H | H | OMe | OMe |
| I-48 | H | Cl | H | Cl | H | OMe | OMe |
| I-49 | H | F | H | F | H | OMe | OMe |
| I-50 | H | Me | H | Me | H | OMe | OMe |
| I-51 | H | OMe | H | OMe | H | OMe | OMe |
| I-52 | H | CF$_3$ | H | CF$_3$ | H | OMe | OMe |
| I-53 | H | CF$_3$ | H | H | H | OMe | OMe |
| I-54 | H | OEt | Me | H | H | OMe | OMe |
| I-55 | H | OEt | OMe | H | H | OMe | OMe |
| I-56 | H | NO$_2$ | H | H | H | OMe | OMe |
| I-57 | H | OBn | H | H | H | OMe | OMe |
| I-58 | H | OMe | H | H | H | OMe | OMe |
| I-59 | H | I | H | H | H | OMe | OMe |
| I-60 | H | H | i-Pr | H | H | OMe | OMe |
| I-61 | H | H | CF$_3$ | H | H | OMe | OMe |
| I-62 | H | OMe | OEt | H | H | OMe | OMe |
| I-63 | H | H | Ph | H | H | OMe | OMe |
| I-64 | OMe | H | Br | H | H | OMe | OMe |
| I-65 | H | OMe | OBn | H | H | OMe | OMe |
| I-66 | H | H | OBn | H | H | OMe | OMe |

TABLE 1-continued (1/15)

| No. | 2 | 3 | 4 | 5 | 6 | R¹ | R² |
|---|---|---|---|---|---|---|---|
| I-67 | H | H | SMe | H | H | OMe | OMe |
| I-68 | H | H | OMe | H | H | OMe | OMe |

TABLE 1

(2/15)

| No. | 2 | 3 | 4 | 5 | 6 | R¹ | R² |
|---|---|---|---|---|---|---|---|
| I-69 | F | H | F | H | H | Br | Br |
| I-70 | Cl | H | H | H | H | Br | Br |
| I-71 | F | H | H | H | H | Br | Br |
| I-72 | H | F | F | H | H | Br | Br |
| I-73 | H | F | H | F | H | Br | Br |
| I-74 | H | Cl | H | H | H | Br | Br |
| I-75 | H | F | H | H | H | Br | Br |
| I-76 | H | H | Cl | H | H | Br | Br |
| I-77 | H | H | CF₃ | H | H | Br | Br |
| I-78 | H | H | F | H | H | Br | Br |
| I-79 | H | H | Me | H | H | Br | Br |
| I-80 | H | H | OMe | H | H | Br | Br |
| I-81 | H | H | H | H | H | Br | Br |
| I-82 | F | F | H | H | H | Cl | CF₃ |
| I-83 | F | H | F | H | H | Cl | CF₃ |
| I-84 | F | H | H | F | H | Cl | CF₃ |
| I-85 | F | H | H | H | F | Cl | CF₃ |
| I-86 | CF₃ | H | H | H | H | Cl | CF₃ |
| I-87 | COOMe | H | H | H | H | Cl | CF₃ |
| I-88 | Cl | H | H | H | H | Cl | CF₃ |
| I-89 | F | H | H | H | H | Cl | CF₃ |
| I-90 | Br | H | H | H | H | Cl | CF₃ |
| I-91 | Me | H | H | H | H | Cl | CF₃ |
| I-92 | OMe | H | H | H | H | Cl | CF₃ |
| I-93 | I | H | H | H | H | Cl | CF₃ |
| I-94 | H | F | F | H | H | Cl | CF₃ |
| I-95 | H | F | H | F | H | Cl | CF₃ |
| I-96 | H | CF₃ | H | H | H | Cl | CF₃ |
| I-97 | H | Cl | H | H | H | Cl | CF₃ |
| I-98 | H | F | H | H | H | Cl | CF₃ |
| I-99 | H | Br | H | H | H | Cl | CF₃ |
| I-100 | H | Me | H | H | H | Cl | CF₃ |
| I-101 | H | OMe | H | H | H | Cl | CF₃ |
| I-102 | H | I | H | H | H | Cl | CF₃ |
| I-103 | H | H | CF₃ | H | H | Cl | CF₃ |
| I-104 | H | H | Cl | H | H | Cl | CF₃ |
| I-105 | H | H | F | H | H | Cl | CF₃ |
| I-106 | H | H | Br | H | H | Cl | CF₃ |
| I-107 | H | H | Me | H | H | Cl | CF₃ |
| I-108 | H | H | OMe | H | H | Cl | CF₃ |
| I-109 | H | H | I | H | H | Cl | CF₃ |
| I-110 | H | H | H | H | H | Cl | CF₃ |
| I-111 | F | F | H | H | H | Cl | Cl |
| I-112 | Me | Me | OMe | H | H | Cl | Cl |
| I-113 | OMe | OMe | H | H | H | Cl | Cl |
| I-114 | Cl | H | Cl | H | H | Cl | Cl |
| I-115 | F | H | F | H | H | Cl | Cl |
| I-116 | Me | H | Me | H | H | Cl | Cl |
| I-117 | OMe | Me | OMe | H | H | Cl | Cl |
| I-118 | OMe | H | OMe | H | H | Cl | Cl |
| I-119 | Cl | H | H | Cl | H | Cl | Cl |
| I-120 | F | H | H | F | H | Cl | Cl |
| I-121 | Me | H | H | Me | H | Cl | Cl |
| I-122 | OMe | H | H | OMe | H | Cl | Cl |
| I-123 | Cl | H | H | H | Cl | Cl | Cl |
| I-124 | F | H | H | H | F | Cl | Cl |
| I-125 | COOEt | H | H | H | H | Cl | Cl |
| I-126 | CF₃ | H | H | H | H | Cl | Cl |
| I-127 | COOH | H | H | H | H | Cl | Cl |
| I-128 | CH₂OH | H | H | H | H | Cl | Cl |

TABLE 1-continued (2/15)

| No. | 2 | 3 | 4 | 5 | 6 | R¹ | R² |
|---|---|---|---|---|---|---|---|
| I-129 | COOMe | H | H | H | H | Cl | Cl |
| I-130 | Et | H | H | H | H | Cl | Cl |
| I-131 | OEt | H | H | H | H | Cl | Cl |
| I-132 | Cl | H | H | H | F | Cl | Cl |
| I-133 | Cl | H | H | H | H | Cl | Cl |
| I-134 | F | H | H | H | H | Cl | Cl |
| I-135 | Br | H | H | H | H | Cl | Cl |
| I-136 | Me | H | H | H | H | Cl | Cl |
| I-137 | OMe | H | H | H | H | Cl | Cl |
| I-138 | I | H | H | H | H | Cl | Cl |
| I-139 | H | OMe | OMe | OMe | H | Cl | Cl |
| I-140 | H | Cl | Cl | H | H | Cl | Cl |
| I-141 | H | F | F | H | H | Cl | Cl |
| I-142 | H | Me | Me | H | H | Cl | Cl |
| I-143 | H | OMe | H | OMe | H | Cl | Cl |
| I-144 | H | Cl | H | Cl | H | Cl | Cl |
| I-145 | H | F | H | F | H | Cl | Cl |
| I-146 | H | Me | H | Me | H | Cl | Cl |
| I-147 | H | CF₃ | H | CF₃ | H | Cl | Cl |
| I-148 | H | CF | H | H | H | Cl | Cl |
| I-149 | H | OBn | H | H | H | Cl | Cl |
| I-150 | H | OEt | OMe | H | H | Cl | Cl |
| I-151 | H | Cl | H | H | H | Cl | Cl |
| I-152 | H | NO₂ | H | H | H | Cl | Cl |
| I-153 | H | F | H | H | H | Cl | Cl |
| I-154 | H | Br | H | H | H | Cl | Cl |
| I-155 | H | Me | H | H | H | Cl | Cl |
| I-156 | H | OMe | H | H | H | Cl | Cl |
| I-157 | H | I | H | H | H | Cl | Cl |
| I-158 | H | H | i-Pr | H | H | Cl | Cl |
| I-159 | H | H | CF₃ | H | H | Cl | Cl |
| I-160 | H | OMe | OBn | H | H | Cl | Cl |
| I-161 | H | H | OBn | H | H | Cl | Cl |
| I-162 | H | H | SMe | H | H | Cl | Cl |
| I-163 | H | H | CO₂Me | H | H | Cl | Cl |
| I-164 | H | OMe | OEt | H | H | Cl | Cl |
| I-165 | H | H | Cl | H | H | Cl | Cl |
| I-166 | H | H | Ph | H | H | Cl | Cl |
| I-167 | H | H | F | H | H | Cl | Cl |
| I-168 | OMe | H | Br | H | H | Cl | Cl |
| I-169 | H | H | Br | H | H | Cl | Cl |
| I-170 | H | H | Me | H | H | Cl | Cl |
| I-171 | H | H | OMe | H | H | Cl | Cl |
| I-172 | H | H | I | H | H | Cl | Cl |
| I-173 | H | H | H | H | H | Cl | Cl |
| I-174 | F | F | H | H | H | Cl | Et |
| I-175 | F | H | F | H | H | Cl | Et |
| I-176 | F | H | H | F | H | Cl | Et |
| I-177 | F | H | H | H | F | Cl | Et |
| I-178 | CF₃ | H | H | H | H | Cl | Et |
| I-179 | COOMe | H | H | H | H | Cl | Et |
| I-180 | Cl | H | H | H | H | Cl | Et |
| I-181 | F | H | H | H | H | Cl | Et |
| I-182 | Br | H | H | H | H | Cl | Et |
| I-183 | Me | H | H | H | H | Cl | Et |
| I-184 | OMe | H | H | H | H | Cl | Et |
| I-185 | I | H | H | H | H | Cl | Et |
| I-186 | H | F | F | H | H | Cl | Et |
| I-187 | H | F | H | F | H | Cl | Et |
| I-188 | H | CF₃ | H | H | H | Cl | Et |
| I-189 | H | Cl | H | H | H | Cl | Et |
| I-190 | H | F | H | H | H | Cl | Et |
| I-191 | H | Br | H | H | H | Cl | Et |
| I-192 | H | Me | H | H | H | Cl | Et |
| I-193 | H | OMe | H | H | H | Cl | Et |
| I-194 | H | I | H | H | H | Cl | Et |
| I-195 | H | H | CF₃ | H | H | Cl | Et |
| I-196 | H | H | Cl | H | H | Cl | Et |
| I-197 | H | H | F | H | H | Cl | Et |
| I-198 | H | H | Br | H | H | Cl | Et |
| I-199 | H | H | Me | H | H | Cl | Et |
| I-200 | H | H | OMe | H | H | Cl | Et |
| I-201 | H | H | I | H | H | Cl | Et |

TABLE 1-continued (2/15)

| No. | 2 | 3 | 4 | 5 | 6 | $R^1$ | $R^2$ |
|---|---|---|---|---|---|---|---|
| I-202 | H | H | H | H | H | Cl | Et |
| I-203 | F | F | H | H | H | Cl | Me |
| I-204 | Cl | H | Cl | H | H | Cl | Me |
| I-205 | F | H | F | H | H | Cl | Me |
| I-206 | Me | H | Me | H | H | Cl | Me |
| I-207 | Cl | H | H | Cl | H | Cl | Me |
| I-208 | F | H | H | F | H | Cl | Me |
| I-209 | Me | H | H | Me | H | Cl | Me |
| I-210 | Cl | H | H | H | Cl | Cl | Me |
| I-211 | F | H | H | H | F | Cl | Me |
| I-212 | $CF_3$ | H | H | H | H | Cl | Me |
| I-213 | COOMe | H | H | H | H | Cl | Me |
| I-214 | Cl | H | H | H | H | Cl | Me |
| I-215 | F | H | H | H | H | Cl | Me |
| I-216 | Br | H | H | H | H | Cl | Me |
| I-217 | Me | H | H | H | H | Cl | Me |
| I-218 | OMe | H | H | H | H | Cl | Me |
| I-219 | I | H | H | H | H | Cl | Me |
| I-220 | H | Cl | Cl | H | H | Cl | Me |
| I-221 | H | F | F | H | H | Cl | Me |
| I-222 | H | Me | Me | H | H | Cl | Me |
| I-223 | H | Cl | H | Cl | H | Cl | Me |
| I-224 | H | F | H | F | H | Cl | Me |
| I-225 | H | Me | H | Me | H | Cl | Me |
| I-226 | H | $CF_3$ | H | H | H | Cl | Me |
| I-227 | H | Cl | H | H | H | Cl | Me |
| I-228 | H | F | H | H | H | Cl | Me |
| I-229 | H | Br | H | H | H | Cl | Me |
| I-230 | H | Me | H | H | H | Cl | Me |
| I-231 | H | OMe | H | H | H | Cl | Me |
| I-232 | H | I | H | H | H | Cl | Me |
| I-233 | H | H | $CF_3$ | H | H | Cl | Me |
| I-234 | H | H | Cl | H | H | Cl | Me |
| I-235 | H | H | F | H | H | Cl | Me |
| I-236 | H | H | Br | H | H | Cl | Me |
| I-237 | H | H | Me | H | H | Cl | Me |
| I-238 | H | H | OMe | H | H | Cl | Me |
| I-239 | H | H | I | H | H | Cl | Me |
| I-240 | H | H | H | H | H | Cl | Me |
| I-241 | F | F | H | H | H | Cl | Ph |
| I-242 | F | H | F | H | H | Cl | Ph |
| I-243 | F | H | H | F | H | Cl | Ph |
| I-244 | F | H | H | H | F | Cl | Ph |
| I-245 | $CF_3$ | H | H | H | H | Cl | Ph |
| I-246 | COOMe | H | H | H | H | Cl | Ph |
| I-247 | Cl | H | H | H | H | Cl | Ph |
| I-248 | F | H | H | H | H | Cl | Ph |
| I-249 | Br | H | H | H | H | Cl | Ph |
| I-250 | Me | H | H | H | H | Cl | Ph |
| I-251 | OMe | H | H | H | H | Cl | Ph |
| I-252 | I | H | H | H | H | Cl | Ph |
| I-253 | H | F | F | H | H | Cl | Ph |
| I-254 | H | F | H | F | H | Cl | Ph |
| I-255 | H | $CF_3$ | H | H | H | Cl | Ph |
| I-256 | H | Cl | H | H | H | Cl | Ph |
| I-257 | H | F | H | H | H | Cl | Ph |
| I-258 | H | Br | H | H | H | Cl | Ph |
| I-259 | H | Me | H | H | H | Cl | Ph |
| I-260 | H | OMe | H | H | H | Cl | Ph |
| I-261 | H | I | H | H | H | Cl | Ph |
| I-262 | H | H | $CF_3$ | H | H | Cl | Ph |
| I-263 | H | H | Cl | H | H | Cl | Ph |
| I-264 | H | H | F | H | H | Cl | Ph |
| I-265 | H | H | Br | H | H | Cl | Ph |
| I-266 | H | H | Me | H | H | Cl | Ph |
| I-267 | H | H | OMe | H | H | Cl | Ph |
| I-268 | H | H | I | H | H | Cl | Ph |
| I-269 | H | H | H | H | H | Cl | Ph |
| I-270 | F | F | H | H | H | Cl | Pr |
| I-271 | F | H | F | H | H | Cl | Pr |
| I-272 | F | H | H | F | H | Cl | Pr |
| I-273 | F | H | H | H | F | Cl | Pr |
| I-274 | $CF_3$ | H | H | H | H | Cl | Pr |
| I-275 | COOMe | H | H | H | H | Cl | Pr |
| I-276 | Cl | H | H | H | H | Cl | Pr |
| I-277 | F | H | H | H | H | Cl | Pr |
| I-278 | Br | H | H | H | H | Cl | Pr |
| I-279 | Me | H | H | H | H | Cl | Pr |
| I-280 | OMe | H | H | H | H | Cl | Pr |
| I-281 | I | H | H | H | H | Cl | Pr |
| I-282 | H | F | F | H | H | Cl | Pr |
| I-283 | H | F | H | F | H | Cl | Pr |
| I-284 | H | $CF_3$ | H | H | H | Cl | Pr |
| I-285 | H | Cl | H | H | H | Cl | Pr |
| I-286 | H | F | H | H | H | Cl | Pr |
| I-287 | H | Br | H | H | H | Cl | Pr |
| I-288 | H | Me | H | H | H | Cl | Pr |
| I-289 | H | OMe | H | H | H | Cl | Pr |
| I-290 | H | I | H | H | H | Cl | Pr |
| I-291 | H | H | $CF_3$ | H | H | Cl | Pr |
| I-292 | H | H | Cl | H | H | Cl | Pr |
| I-293 | H | H | F | H | H | Cl | Pr |
| I-294 | H | H | Br | H | H | Cl | Pr |
| I-295 | H | H | Me | H | H | Cl | Pr |
| I-296 | H | H | OMe | H | H | Cl | Pr |
| I-297 | H | H | I | H | H | Cl | Pr |
| I-298 | H | H | H | H | H | Cl | Pr |
| I-299 | F | F | H | H | H | Cl | i-Pr |
| I-300 | F | H | F | H | H | Cl | i-Pr |
| I-301 | F | H | H | F | H | Cl | i-Pr |
| I-302 | F | H | H | H | F | Cl | i-Pr |
| I-303 | $CF_3$ | H | H | H | H | Cl | i-Pr |
| I-304 | H | H | H | H | H | Cl | i-Pr |
| I-305 | Cl | H | H | H | H | Cl | i-Pr |
| I-306 | F | H | H | H | H | Cl | i-Pr |
| I-307 | Br | H | H | H | H | Cl | i-Pr |
| I-308 | Me | H | H | H | H | Cl | i-Pr |
| I-309 | OMe | H | H | H | H | Cl | i-Pr |
| I-310 | I | H | H | H | H | Cl | i-Pr |
| I-311 | H | F | F | H | H | Cl | i-Pr |
| I-312 | H | F | H | F | H | Cl | i-Pr |
| I-313 | H | $CF_3$ | H | H | H | Cl | i-Pr |
| I-314 | H | Cl | H | H | H | Cl | i-Pr |
| I-315 | H | F | H | H | H | Cl | i-Pr |
| I-316 | H | Br | H | H | H | Cl | i-Pr |
| I-317 | H | Me | H | H | H | Cl | i-Pr |
| I-318 | H | OMe | H | H | H | Cl | i-Pr |
| I-319 | H | I | H | H | H | Cl | i-Pr |
| I-320 | H | H | $CF_3$ | H | H | Cl | i-Pr |
| I-321 | H | H | Cl | H | H | Cl | i-Pr |
| I-322 | H | H | F | H | H | Cl | i-Pr |
| I-323 | H | H | Br | H | H | Cl | i-Pr |
| I-324 | H | H | Me | H | H | Cl | i-Pr |
| I-325 | H | H | OMe | H | H | Cl | i-Pr |
| I-326 | H | H | I | H | H | Cl | i-Pr |
| I-327 | H | H | H | H | H | Cl | i-Pr |

TABLE 1

(3/15)

| No. | $X_n$ | $R^1$ | $R^1$ |
|---|---|---|---|
| I-328 | n = 0 for | OCHF$_2$ | OCHF$_2$ |
| I-329 | Compound I-328 | CF$_3$ | OCH$_2$C(Me)=CH$_2$ |
| I-330 | through | CF$_3$ | OCH$_2$CCH |
| I-331 | Compound I-437 | CF$_3$ | OCH$_2$CH$_2$C(Me)=CH$_2$ |
| I-332 | | CF$_3$ | OCH$_2$CH=C(Me)$_2$ |
| I-333 | | CF$_3$ | OCH$_2$CH=CH$_2$ |
| I-334 | | CF$_3$ | OCH$_2$CH=CHMe |
| I-335 | | Cl | O-i-Bu |
| I-336 | | Cl | OBu |
| I-337 | | Cl | OCH$_2$C(Me)=CH$_2$ |
| I-338 | | Cl | OCH$_2$C$_2$F$_5$ |
| I-339 | | Cl | OCH$_2$CCH |
| I-340 | | Cl | OCH$_2$CF$_3$ |
| I-341 | | Cl | OCH$_2$CH$_2$C(Me)=CH$_2$ |
| I-342 | | Cl | OCH$_2$CH=C(Me)$_2$ |
| I-343 | | Cl | OCH$_2$CH=CH$_2$ |
| I-344 | | Cl | OCH$_2$CH=CHMe |
| I-345 | | Cl | OEt |
| I-346 | | Cl | OMe |
| I-347 | | Cl | OPr |
| I-348 | | Et | OCH$_2$C(Me)=CH$_2$ |
| I-349 | | Et | OCH$_2$CCH |
| I-350 | | Et | OCH$_2$CH$_2$C(Me)=CH$_2$ |
| I-351 | | Et | OCH$_2$CH=C(Me)$_2$ |
| I-352 | | Et | OCH$_2$CH=CH$_2$ |
| I-353 | | Et | OCH$_2$CH=CHMe |
| I-354 | | Me | O-i-Pr |
| I-355 | | Me | OCH$_2$C(Me)=CH$_2$ |
| I-356 | | Me | OCH$_2$CCH |
| I-357 | | Me | OCH$_2$CH$_2$C(Me)=CH$_2$ |
| I-358 | | Me | OCH$_2$CH=C(Me)$_2$ |
| I-359 | | Me | OCH$_2$CH=CH$_2$ |
| I-360 | | Me | OCH$_2$CH=CHMe |
| I-361 | | Me | OEt |
| I-362 | | Me | OMe |
| I-363 | | O-i-Bu | O-i-Bu |
| I-364 | | OBu | OBu |
| I-365 | | OCH$_2$C(Me)=CH$_2$ | OCH$_2$C(Me)=CH$_2$ |
| I-366 | | OCH$_2$CCH | OCH$_2$CCH |
| I-367 | | OCH$_2$CH$_2$C(Me)=CH$_2$ | OCH$_2$CH$_2$C(Me)=CH$_2$ |
| I-368 | | OCH$_2$CH=C(Me)$_2$ | OCH$_2$CH=C(Me)$_2$ |
| I-369 | | OCH$_2$CH=CH$_2$ | OCH$_2$CH=CH$_2$ |
| I-370 | | OCH$_2$CH=CHMe | OCH$_2$CH=CHMe |
| I-371 | | OEt | OEt |
| I-372 | | OMe | OMe |
| I-373 | | OPr | OPr |
| I-374 | | Pr | OCH$_2$C(Me)=CH$_2$ |
| I-375 | | Pr | OCH$_2$CCH |
| I-376 | | Pr | OCH$_2$CH$_2$C(Me)=CH$_2$ |
| I-377 | | Pr | OCH$_2$CH=C(Me)$_2$ |
| I-378 | | Pr | OCK21CN=CN2 |
| I-379 | | Pr | OCH$_2$CH=CHMe |
| I-380 | | i-Pr | OCH$_2$C(Me)=CH$_2$ |
| I-381 | | i-Pr | OCH$_2$CCH |
| I-382 | | i-Pr | OCH$_2$CH$_2$C(Me)=CH$_2$ |
| I-383 | | i-Pr | OCH$_2$CH=C(Me)$_2$ |
| I-384 | | i-Pr | OCH$_2$CH=CH$_2$ |
| I-385 | | i-Pr | OCH$_2$CH=CHMe |
| I-386 | | O-i-Bu | OCH$_2$C(Me)=CH$_2$ |
| I-387 | | O-i-Bu | OCH$_2$CCH |
| I-388 | | O-i-Bu | OCH$_2$CH$_2$C(Me)=CH$_2$ |
| I-389 | | O-i-Bu | OCH$_2$CH=C(Me)$_2$ |
| I-390 | | O-i-Bu | OCH$_2$CH=CH$_2$ |
| I-391 | | O-i-Bu | OCH$_2$CH=CHMe |
| I-392 | | OBu | O-i-Bu |
| I-393 | | OBu | OCH$_2$C(Me)=CH$_2$ |
| I-394 | | OBu | OCH$_2$CCH |
| I-395 | | OBu | OCH$_2$CH$_2$C(Me)=CH$_2$ |
| I-396 | | OBu | OCH$_2$CH=C(Me)$_2$ |
| I-397 | | OBu | OCH$_2$CH=CH$_2$ |
| I-398 | | OBu | OCH$_2$CH=CHMe |
| I-399 | | OCH$_2$CF$_3$ | OCH$_2$C(Me)=CH$_2$ |
| I-400 | | OCH$_2$CF$_3$ | OCH$_2$C$_2$F$_5$ |
| I-401 | | OCH$_2$CF$_3$ | OCH$_2$CCH |
| I-402 | | OCH$_2$CF$_3$ | OCH$_2$CH$_2$C(Me)=CH$_2$ |

TABLE 1-continued (3/15)

| No. | $X_n$ | $R^1$ | $R^1$ |
|---|---|---|---|
| I-403 | | $OCH_2CF_3$ | $OCH_2CH=C(Me)_2$ |
| I-404 | | $OCH_2CF_3$ | $OCH_2CH=CH_2$ |
| I-405 | | $OCH_2CF_3$ | $OCH_2CH=CHMe$ |
| I-406 | | $OCH_2CH=CH_2$ | $OCH_2C(Me)=CH_2$ |
| I-407 | | $OCH_2CH=CH_2$ | $OCH_2CCH$ |
| I-408 | | $OCH_2CH=CH_2$ | $OCH_2CH_2C(Me)=CH_2$ |
| I-409 | | $OCH_2CH=CH_2$ | $OCH_2CH=C(Me)_2$ |
| I-410 | | $OCH_2CH=CH_2$ | $OCH_2CH=CHMe$ |
| I-411 | | OEt | O-i-Bu |
| I-412 | | OEt | OBu |
| I-413 | | OEt | $OCH_2C(Me)=CH_2$ |
| I-414 | | OEt | $OCH_2CCH$ |
| I-415 | | OEt | $OCH_2CH_2C(Me)=CH_2$ |
| I-416 | | OEt | $OCH_2CH=C(Me)_2$ |
| I-417 | | OEt | $OCH_2CH=CH_2$ |
| I-418 | | OEt | $OCH_2CH=CHMe$ |
| I-419 | | OEt | OPr |
| I-420 | | OMe | O-i-Bu |
| I-421 | | OMe | OBu |
| I-422 | | OMe | $OCH_2C(Me)=CH2-$ |
| I-423 | | OMe | $OCH_2CCH$ |
| I-424 | | OMe | $OCH_2CH_2C(Me)=CH_2$ |
| I-425 | | OMe | $OCH_2CH=C(Me)_2$ |
| I-426 | | OMe | $OCH_2CH=CH_2$ |
| I-427 | | OMe | $OCH_2CH=CHMe$ |
| I-428 | | OMe | OEt |
| I-429 | | OMe | OPr |
| I-430 | | OPr | O-i-Bu |
| I-431 | | OPr | OBu |
| I-432 | | OPr | $OCH_2C(Me)=CH_2$ |
| I-433 | | OPr | $OCH_2CCH$ |
| I-434 | | OPr | $OCH_2CH_2C(Me)=CH_2$ |
| I-435 | | OPr | $OCH_2CH=C(Me)_2$ |
| I-436 | | OPr | $OCH_2CH=CH_2$ |
| I-437 | | OPr | $OCH_2CH=CHMe$ |
| I-2001 | n = 0 for | Me | SMe |
| I-2002 | Compound I-2001 | Me | SEt |
| I-2003 | through | Me | SPr |
| I-2004 | Compound I-2015 | OMe | SMe |
| I-2005 | | OMe | SEt |
| I-2006 | | OMe | SPr |
| I-2007 | | SMe | SMe |
| I-2008 | | SEt | SEt |
| I-2009 | | SPr | SPr |
| I-2010 | | $OCH_2CH=CH_2$ | SMe |
| I-2011 | | $OCH_2CH=CH_2$ | SEt |
| I-2012 | | $OCH_2CH=CH_2$ | SPr |
| I-2013 | | Cl | SMe |
| I-2014 | | Cl | SEt |
| I-2015 | | Cl | SPr |

(4/15)

| No. | $X_n$ | $R^1$ | $R^1$ |
|---|---|---|---|
| I-438 | A chlorine atom | $OCHF_2$ | $OCHF_2$ |
| I-439 | at 2-position | $CF_3$ | $OCH_2C(Me)=CH_2$ |
| I-440 | (2-Cl) for | $CF_3$ | $OCH_2CCH$ |
| I-441 | Compound I-438 | $CF_3$ | $OCH_2CH_2C(Me)=CH_2$ |
| I-442 | through | $CF_3$ | $OCH_2CH=C(Me)_2$ |
| I-443 | Compound I-547 | $CF_3$ | $OCH_2CH=CH_2$ |
| I-444 | | $CF_3$ | $OCH_2CH=CHMe$ |
| I-445 | | Cl | O-i-Bu |
| I-446 | | Cl | OBu |
| I-447 | | Cl | $OCH_2C(Me)=CH_2$ |
| I-448 | | Cl | $OCH_2C_2F_5$ |
| I-449 | | Cl | $OCH_2CCH$ |
| I-450 | | Cl | $OCH_2CF_3$ |
| I-451 | | Cl | $OCH_2CH_2C(Me)=CH_2$ |
| I-452 | | Cl | $OCH_2CH=C(Me)_2$ |
| I-453 | | Cl | $OCH_2CH=CH_2$ |
| I-454 | | Cl | $OCH_2CH=CHMe$ |

-continued (4/15)

| No. | $X_n$ | $R^1$ | $R^1$ |
|---|---|---|---|
| I-455 | | Cl | OEt |
| I-456 | | Cl | OMe |
| I-457 | | Cl | OPr |
| I-458 | | Et | $OCH_2C(Me)=CH_2$ |
| I-459 | | Et | $OCH_2CCH$ |
| I-460 | | Et | $OCH_2CH_2C(Me)=CH_2$ |
| I-461 | | Et | $OCH_2CH=C(Me)_2$ |
| I-462 | | Et | $OCH_2CH=CH_2$ |
| I-463 | | Et | $OCH_2CH=CHMe$ |
| I-464 | | Me | O-i-Pr |
| I-465 | | Me | $OCH_2C(Me)=CH_2$ |
| I-466 | | Me | $OCH_2CCH$ |
| I-467 | | Me | $OCH_2CH_2C(Me)=CH_2$ |
| I-468 | | Me | $OCH_2CH=C(Me)_2$ |
| I-469 | | Me | $OCH_2CH=CH_2$ |
| I-470 | | Me | $OCH_2CH=CHMe$ |
| I-471 | | Me | OEt |
| I-472 | | Me | OMe |
| I-473 | | O-i-Bu | O-i-Bu |
| I-474 | | OBu | OBu |
| I-475 | | $OCH_2C(Me)=CH_2$ | $OCH_2C(Me)=CH_2$ |
| I-476 | | $OCH_2CCH$ | $OCH_2CCH$ |
| I-477 | | $OCH_2CH_2C(Me)=CH_2$ | $OCH_2CH_2C(Me)=CH_2$ |
| I-478 | | $OCH_2CH=C(Me)_2$ | $OCH_2CH=C(Me)_2$ |
| I-479 | | $OCH_2CH=CH_2$ | $OCH_2CH=CH_2$ |
| I-480 | | $OCH_2CH=CHMe$ | $OCH_2CH=CHMe$ |
| I-481 | | OEt | OEt |
| I-482 | | OMe | OMe |
| I-483 | | OPr | OPr |
| I-484 | | Pr | $OCH_2C(Me)=CH_2$ |
| I-485 | | Pr | $OCH_2CCH$ |
| I-486 | | Pr | $OCH_2CH_2C(Me)=CH_2$ |
| I-487 | | Pr | $OCH_2CH=C(Me)_2$ |
| I-488 | | Pr | $OCH_2CH=CH_2$ |
| I-489 | | Pr | $OCH_2CH=CHMe$ |
| I-490 | | i-Pr | $OCH_2C(Me)=CH_2$ |
| I-491 | | i-Pr | $OCH_2CCH$ |
| I-492 | | i-Pr | $OCH_2CH_2C(Me)=CH_2$ |
| I-493 | | i-Pr | $OCH_2CH=C(Me)_2$ |
| I-494 | | i-Pr | $OCH_2CH=CH_2$ |
| I-495 | | i-Pr | $OCH_2CH=CHMe$ |
| I-496 | | O-i-Bu | $OCH_2C(Me)=CH_2$ |
| I-497 | | O-i-Bu | $OCH_2CCH$ |
| I-498 | | O-i-Bu | $OCH_2CH_2C(Me)=CH_2$ |
| I-499 | | O-i-Bu | $OCH_2CH=C(Me)_2$ |
| I-500 | | O-i-Bu | $OCH_2CH=CH_2$ |
| I-501 | | O-i-Bu | $OCH_2CH=CHMe$ |
| I-502 | | OBu | O-i-Bu |
| I-503 | | OBu | $OCH_2C(Me)=CH_2$ |
| I-504 | | OBu | $OCH_2CCH$ |
| I-505 | | OBu | $OCH_2CH_2C(Me)=CH_2$ |
| I-506 | | OBu | $OCH_2CH=C(Me)_2$ |
| I-507 | | OBu | $OCH_2CH=CH_2$ |
| I-508 | | OBu | $OCH_2CH=CHMe$ |
| I-509 | | $OCH_2CF_3$ | $OCH_2C(Me)=CH_2$ |
| I-510 | | $OCH_2CF_3$ | $OCH_2C_2F_5$ |
| I-511 | | $OCH_2CF_3$ | $OCH_2CCH$ |
| I-512 | | $OCH_2CF_3$ | $OCH_2CH_2C(Me)=CH_2$ |
| I-513 | | $OCH_2CF_3$ | $OCH_2CH=C(Me)_2$ |
| I-514 | | $OCH_2CF_3$ | $OCH_2CH=CH_2$ |
| I-515 | | $OCH_2CF_3$ | $OCH_2CH=CHMe$ |
| I-516 | | $OCH_2CH=CH_2$ | $OCH_2C(Me)=CH_2$ |
| I-517 | | $OCH_2CH=CH_2$ | $OCH_2CCH$ |
| I-518 | | $OCH_2CH=CH_2$ | $OCH_2CH_2C(Me)=CH_2$ |
| I-519 | | $OCH_2CH=CH_2$ | $OCH_2CH=C(Me)_2$ |
| I-520 | | $OCH_2CH=CH_2$ | $OCH_2CH=CHMe$ |
| I-521 | | OEt | O-i-Bu |
| I-522 | | OEt | OBu |
| I-523 | | OEt | $OCH_2C(Me)=CH_2$ |
| I-524 | | OEt | $OCH_2CCH$ |
| I-525 | | OEt | $OCH_2CH_2C(Me)=CH_2$ |
| I-526 | | OEt | $OCH_2CH=C(Me)_2$ |
| I-527 | | OEt | $OCH_2CH=CH_2$ |
| I-528 | | OEt | $OCH_2CH=CHMe$ |
| I-529 | | OEt | OPr |
| I-530 | | OMe | O-i-Bu |

-continued (4/15)

| No. | $X_n$ | $R^1$ | $R^1$ |
|---|---|---|---|
| I-531 | | OMe | OBu |
| I-532 | | OMe | $OCH_2C(Me)=CH_2$ |
| I-533 | | OMe | $OCH_2CCH$ |
| I-534 | | OMe | $OCH_2CH_2C(Me)=CH_2$ |
| I-535 | | OMe | $OCH_2CH=C(Me)_2$ |
| I-536 | | OMe | $OCH_2CH=CH_2$ |
| I-537 | | OMe | $OCH_2CH=CHMe$ |
| I-538 | | OMe | OEt |
| I-539 | | OMe | OPr |
| I-540 | | OPr | O-i-Bu |
| I-541 | | OPr | OBu |
| I-542 | | OPr | $OCH_2C(Me)=CH_2$ |
| I-543 | | OPr | $OCH_2CCH$ |
| I-544 | | OPr | $OCH_2CH_2C(Me)=CH_2$ |
| I-545 | | OPr | $OCH_2CH=C(Me)_2$ |
| I-546 | | OPr | $OCH_2CH=CH_2$ |
| I-547 | | OPr | $OCH_2CH=CHMe$ |

TABLE 1

(5/15)

| No. | $X_n$ | $R^1$ | $R^1$ |
|---|---|---|---|
| I-548 | A fluorine atom | $OCHF_2$ | $OCHF_2$ |
| I-549 | at 2-position | $CF_3$ | $OCH_2C(Me)=CH_2$ |
| I-550 | (2-F) for | $CF_3$ | $OCH_2CCH$ |
| I-551 | Compound I-548 | $CF_3$ | $OCH_2CH_2C(Me)=CH_2$ |
| I-552 | through | $CF_3$ | $OCH_2CH=C(Me)_2$ |
| I-553 | Compound I-657 | $CF_3$ | $OCH_2CH=CH_2$ |
| I-554 | through | $CF_3$ | $OCH_2CH=CHMe$ |
| I-555 | Compound | Cl | O-i-Bu |
| I-556 | I-657 | Cl | OBu |
| I-557 | | Cl | $OCH_2C(Me)=CH_2$ |
| I-558 | | Cl | $OCH_2C_2F_5$ |
| I-559 | | Cl | $OCH_2CCH$ |
| I-560 | | Cl | $OCH_2CF_3$ |
| I-561 | | Cl | $OCH_2CH_2C(Me)=CH_2$ |
| I-562 | | Cl | $OCH_2CH=C(Me)_2$ |
| I-563 | | Cl | $OCH_2CH=CH_2$ |
| I-564 | | Cl | $OCH_2CH=CHMe$ |
| I-565 | | Cl | OEt |
| I-566 | | Cl | OMe |
| I-567 | | Cl | OPr |
| I-568 | | Et | $OCH_2C(Me)=CH_2$ |
| I-569 | | Et | $OCH_2CCH$ |
| I-570 | | Et | $OCH_2CH_2C(Me)=CH_2$ |
| I-571 | | Et | $OCH_2CH=C(Me)_2$ |
| I-572 | | Et | $OCH_2CH=CH_2$ |
| I-573 | | Et | $OCH_2CH=CHMe$ |
| I-574 | | Me | O-i-Pr |
| I-575 | | Me | $OCH_2C(Me)=CH_2$ |
| I-576 | | Me | $OCH_2CCH$ |
| I-577 | | Me | $OCH_2CH_2C(Me)=CH_2$ |
| I-578 | | Me | $OCH_2CH=C(Me)_2$ |
| I-579 | | Me | $OCH_2CH=CH_2$ |
| I-580 | | Me | $OCH_2CH=CHMe$ |
| I-581 | | Me | OEt |
| I-582 | | Me | OMe |
| I-583 | | O-i-Bu | O-i-Bu |
| I-584 | | OBu | OBu |
| I-585 | | $OCH_2C(Me)=CH_2$ | $OCH_2C(Me)=CH_2$ |
| I-586 | | $OCH_2CCH$ | $OCH_2CCH$ |
| I-587 | | $OCH_2CH_2C(Me)=CH_2$ | $OCH_2CH_2C(Me)=CH_2$ |
| I-588 | | $OCH_2CH=C(Me)_2$ | $OCH_2CH=C(Me)_2$ |
| I-589 | | $OCH_2CH=CH_2$ | $OCH_2CH=CH_2$ |
| I-590 | | $OCH_2CH=CHMe$ | $OCH_2CH=CHMe$ |
| I-591 | | OEt | OEt |
| I-592 | | OMe | OMe |
| I-593 | | OPr | OPr |
| I-594 | | Pr | $OCH_2C(Me)=CH_2$ |
| I-595 | | Pr | $OCH_2CCH$ |
| I-596 | | Pr | $OCH_2CH_2C(Me)=CH_2$ |
| I-597 | | Pr | $OCH_2CH=C(Me)_2$ |

TABLE 1-continued (5/15)

| No. | $X_n$ | $R^1$ | $R^1$ |
|---|---|---|---|
| I-598 | | Pr | OCH$_2$CH=CH$_2$ |
| I-599 | | Pr | OCH$_2$CH=CHMe |
| I-600 | | i-Pr | OCH$_2$C(Me)=CH$_2$ |
| I-601 | | i-Pr | OCH$_2$CCH |
| I-602 | | i-Pr | OCH$_2$CH$_2$C(Me)=CH$_2$ |
| I-603 | | i-Pr | OCH$_2$CH=C(Me)$_2$ |
| I-604 | | i-Pr | OCH$_2$CH=CH$_2$ |
| I-605 | | i-Pr | OCH$_2$CH=CHMe |
| I-606 | | O-i-Bu | OCH$_2$C(Me)=CH$_2$ |
| I-607 | | O-i-Bu | OCH$_2$CCH |
| I-608 | | O-i-Bu | OCH$_2$CH$_2$C(Me)=CH$_2$ |
| I-609 | | O-i-Bu | OCH$_2$CH=C(Me)$_2$ |
| I-610 | | O-i-Bu | OCH$_2$CH=CH$_2$ |
| I-611 | | O-i-Bu | OCH$_2$CH=CHMe |
| I-612 | | OBu | O-i-Bu |
| I-613 | | OBu | OCH$_2$C(Me)=CH$_2$ |
| I-614 | | OBu | OCH$_2$CCH |
| I-615 | | OBu | OCH$_2$CH$_2$C(Me)=CH$_2$ |
| I-616 | | OBu | OCH$_2$CH=C(Me)$_2$ |
| I-617 | | OBu | OCH$_2$CH=CH$_2$ |
| I-618 | | OBu | OCH$_2$CH=CHMe |
| I-619 | | OCH$_2$CF$_3$ | OCH$_2$C(Me)=CH$_2$ |
| I-620 | | OCH$_2$CF$_3$ | OCH$_2$C$_2$F$_5$ |
| I-621 | | OCH$_2$CF$_3$ | OCH$_2$CCH |
| I-622 | | OCH$_2$CF$_3$ | OCH$_2$CH$_2$C(Me)=CH$_2$ |
| I-623 | | OCH$_2$CF$_3$ | OCH$_2$CH=C(Me)$_2$ |
| I-624 | | OCH$_2$CF$_3$ | OCH$_2$CH=CH$_2$ |
| I-625 | | OCH$_2$CF$_3$ | OCH$_2$CH=CHMe |
| I-626 | | OCH$_2$CH=CH$_2$ | OCH$_2$C(Me)=CH$_2$ |
| I-627 | | OCH$_2$CH=CH$_2$ | OCH$_2$CCH |
| I-628 | | OCH$_2$CH=CH$_2$ | OCH$_2$CH$_2$C(Me)=CH$_2$ |
| I-629 | | OCH$_2$CH=CH$_2$ | OCH$_2$CH=C(Me)$_2$ |
| I-630 | | OCH$_2$CH=CH$_2$ | OCH$_2$CH=CHMe |
| I-631 | | OEt | O-i-Bu |
| I-632 | | OEt | OBu |
| I-633 | | OEt | OCH$_2$C(Me)=CH$_2$ |
| I-634 | | OEt | OCH$_2$CCH |
| I-635 | | OEt | OCH$_2$CH$_2$C(Me)=CH$_2$ |
| I-636 | | OEt | OCH$_2$CH=C(Me)$_2$ |
| I-637 | | OEt | OCH$_2$CH=CH$_2$ |
| I-638 | | OEt | OCH$_2$CH=CHMe |
| I-639 | | OEt | OPr |
| I-640 | | OMe | O-i-Bu |
| I-641 | | OMe | OBu |
| I-642 | | OMe | OCH$_2$C(Me)=CH$_2$ |
| I-643 | | OMe | OCH$_2$CCE |
| I-644 | | OMe | OCH$_2$CH$_2$C(Me)=CH$_2$ |
| I-645 | | OMe | OCH$_2$CH=C(Me)$_2$ |
| I-646 | | OMe | OCH$_2$CH=CH$_2$ |
| I-647 | | OMe | OCH$_2$CH=CHMe |
| I-648 | | OMe | OEt |
| I-649 | | OMe | OPr |
| I-650 | | OPr | O-i-Bu |
| I-651 | | OPr | OBu |
| I-652 | | OPr | OCH$_2$C(Me)=CH$_2$ |
| I-653 | | OPr | OCH$_2$CCH |
| I-654 | | OPr | OCH$_2$CH$_2$C(Me)=CH$_2$ |
| I-655 | | OPr | OCH$_2$CH=C(Me)$_2$ |
| I-656 | | OPr | OCH$_2$CH=CH$_2$ |
| I-657 | | OPr | OCH$_2$CH=CHMe |

TABLE 1

(6/15)

| No. | $X_n$ | $R^1$ | $R^1$ |
|---|---|---|---|
| I-658 | A bromine atom at 2-position (2-Br) for Compound I-658 through Compound I-767 | OCHF$_2$ | OCHF$_2$ |
| I-659 | | CF$_3$ | OCH$_2$C(Me)=CH$_2$ |
| I-660 | | CF$_3$ | OCH$_2$CCH |
| I-661 | | CF$_3$ | OCH$_2$CH$_2$C(Me)=CH$_2$ |
| I-662 | | CF$_3$ | OCH$_2$CH=C(Me)$_2$ |
| I-663 | | CF$_3$ | OCH$_2$CH=CH$_2$ |

TABLE 1-continued (6/15)

| No. | $X_n$ | $R^1$ | $R^1$ |
|---|---|---|---|
| I-664 | | CF$_3$ | OCH$_2$CH=CHMe |
| I-665 | | Cl | O-i-Bu |
| I-666 | | Cl | OBu |
| I-667 | | Cl | OCH$_2$C(Me)=CH$_2$ |
| I-668 | | Cl | OCH$_2$C$_2$F$_5$ |
| I-669 | | Cl | OCH$_2$CCH |
| I-670 | | Cl | OCH$_2$CF$_3$ |
| I-671 | | Cl | OCH$_2$CH$_2$C(Me)=CH$_2$ |
| I-672 | | Cl | OCH$_2$CH=C(Me)$_2$ |
| I-673 | | Cl | OCH$_2$CH=CH$_2$ |
| I-674 | | Cl | OCH$_2$CH=CHMe |
| I-675 | | Cl | OEt |
| I-676 | | Cl | OMe |
| I-677 | | Cl | OPr |
| I-678 | | Et | OCH$_2$C(Me)=CH$_2$ |
| I-679 | | Et | OCH$_2$CCH |
| I-680 | | Et | OCH$_2$CH$_2$C(Me)=CHi |
| I-681 | | Et | OCH$_2$CH=C(Me)$_2$ |
| I-682 | | Et | OCH$_2$CH=CH$_2$ |
| I-683 | | Et | OCH$_2$CH=CHMe |
| I-684 | | Me | O-i-Pr |
| I-685 | | Me | OCH$_2$C(Me)=CH$_2$ |
| I-686 | | Me | OCH$_2$CCH |
| I-687 | | Me | OCH$_2$CH$_2$C(Me)=CH$_2$ |
| I-688 | | Me | OCH$_2$CH=C(Me)$_2$ |
| I-689 | | Me | OCH$_2$CH=CH$_2$ |
| I-690 | | Me | OCH$_2$CH=CHMe |
| I-691 | | Me | OEt |
| I-692 | | Me | OMe |
| I-693 | | O-i-Bu | O-i-Bu |
| I-694 | | OBu | OBu |
| I-695 | | OCH$_2$C(Me)=CH$_2$ | OCH$_2$C(Me)=CH$_2$ |
| I-696 | | OCH$_2$CCH | OCH$_2$CCH |
| I-697 | | OCH$_2$CH$_2$C(Me)=CH$_2$ | OCH$_2$CH$_2$C(Me)=CH$_2$ |
| I-698 | | OCH$_2$CH=C(Me)$_2$ | OCH$_2$CH=C(Me)$_2$ |
| I-699 | | OCH$_2$CH=CH$_2$ | OCH$_2$CH=CH$_2$ |
| I-700 | | OCH$_2$CH=CHMe | OCH$_2$CH=CHMe |
| I-701 | | OEt | OEt |
| I-702 | | OMe | OMe |
| I-703 | | OPr | OPr |
| I-704 | | Pr | OCH$_2$C(Me)=CH$_2$ |
| I-705 | | Pr | OCH$_2$CCH |
| I-706 | | Pr | OCH$_2$CH$_2$C(Me)=CH$_2$ |
| I-707 | | Pr | OCH$_2$CH=C(Me)$_2$ |
| I-708 | | Pr | OCH$_2$CH=CH$_2$ |
| I-709 | | Pr | OCH$_2$CH=CHMe |
| I-710 | | i-Pr | OCH$_2$C(Me)=CH$_2$ |
| I-711 | | i-Pr | OCH$_2$CCH |
| I-712 | | i-Pr | OCH$_2$CH$_2$C(Me)=CH$_2$ |
| I-713 | | i-Pr | OCH$_2$CH=C(Me)$_2$ |
| I-714 | | i-Pr | OCH$_2$CH=CH$_2$ |
| I-715 | | i-Pr | OCH$_2$CH=CHMe |
| I-716 | | O-i-Bu | OCH$_2$C(Me)=CH$_2$ |
| I-717 | | O-i-Bu | OCH$_2$CCH |
| I-718 | | O-i-Bu | OCH$_2$CH$_2$C(Me)=CH$_2$ |
| I-719 | | O-i-Bu | OCH$_2$CH=C(Me)$_2$ |
| I-720 | | O-i-Bu | OCH$_2$CH=CH$_2$ |
| I-721 | | O-i-Bu | OCH$_2$CH=CHMe |
| I-722 | | OBu | O-i-Bu |
| I-723 | | OBu | OCH$_2$C(Me)=CH$_2$ |
| I-724 | | OBu | OCH$_2$CCH |
| I-725 | | OBu | OCH$_2$CH$_2$C(Me)=CH$_2$ |
| I-726 | | OBu | OCH$_2$CH=C(Me)$_2$ |
| I-727 | | OBu | OCH$_2$CH=CH$_2$ |
| I-728 | | OBu | OCH$_2$CH=CHMe |
| I-729 | | OCH$_2$CF$_3$ | OCH$_2$C(Me)=CH$_2$ |
| I-730 | | OCH$_2$CF$_3$ | OCH$_2$C$_2$F$_5$ |
| I-731 | | OCH$_2$CF$_3$ | OCH$_2$CCH |
| I-732 | | OCH$_2$CF$_3$ | OCH$_2$CH$_2$C(Me)=CH$_2$ |
| I-733 | | OCH$_2$CF$_3$ | OCH$_2$CH=C(Me)$_2$ |
| I-734 | | OCH$_2$CF$_3$ | OCH$_2$CH=CH$_2$ |
| I-735 | | OCH$_2$CF$_3$ | OCH$_2$CH=CHMe |
| I-736 | | OCH$_2$CH=CH$_2$ | OCH$_2$C(Me)=CH$_2$ |
| I-737 | | OCH$_2$CH=CH$_2$ | OCH$_2$CCH |
| I-738 | | OCH$_2$CH=CH$_2$ | OCH$_2$CH$_2$C(Me)=CH$_2$ |

TABLE 1-continued (6/15)

| No. | $X_n$ | $R^1$ | $R^1$ |
|---|---|---|---|
| I-739 | | OCH₂CH=CH₂ | OCH₂CH=C(Me)₂ |
| I-740 | | OCH₂CH=CH₂ | OCH₂CH=CHMe |
| I-741 | | OEt | O-i-Bu |
| I-742 | | OEt | OBu |
| I-743 | | OEt | OCH₂C(Me)=CH₂ |
| I-744 | | OEt | OCH₂CCH |
| I-745 | | OEt | OCH₂CH₂C(Me)=CH₂ |
| I-746 | | OEt | OCH₂CH=C(Me)₂ |
| I-747 | | OEt | OCH₂CH=CH₂ |
| I-748 | | OEt | OCH₂CH=CHMe |
| I-749 | | OEt | OPr |
| I-750 | | OMe | O-i-Bu |
| I-751 | | OMe | OBu |
| I-752 | | OMe | OCH₂C(Me)=CH₂ |
| I-753 | | OMe | OCH₂CCH |
| I-754 | | OMe | OCH₂CH₂C(Me)=CH₂ |
| I-755 | | OMe | OCH₂CH=C(Me)₂ |
| I-756 | | OMe | OCH₂CH=CH₂ |
| I-757 | | OMe | OCH₂CH=CHMe |
| I-758 | | OMe | OEt |
| I-759 | | OMe | OPr |
| I-760 | | OPr | O-i-Bu |
| I-761 | | OPr | OBu |
| I-762 | | OPr | OCH₂C(Me)=CH₂ |
| I-763 | | OPr | OCH₂CCH |
| I-764 | | OPr | OCH₂CH₂C(Me)=CH₂ |
| I-765 | | OPr | OCH₂CH=C(Me)₂ |
| I-766 | | OPr | OCH₂CH=CH₂ |
| I-767 | | OPr | OCH₂CH=CHMe |

(7/15)

| No. | $X_n$ | $R^1$ | $R^1$ |
|---|---|---|---|
| I-768 | A methyl group | OCHF₂ | OCHF₂ |
| I-769 | at 2-position | CF₃ | OCH₂C(Me)=CH₂ |
| I-770 | (2-Me) for | CF₃ | OCH₂CCH |
| I-771 | Compound I-768 | CF₃ | OCH₂CH₂C(Me)=CH₂ |
| I-772 | through | CF₃ | OCH₂CH=C(Me)₂ |
| I-773 | Compound I-877 | CF₃ | OCH₂CH=CH₂ |
| I-774 | | CF₃ | OCH₂CH=CHMe |
| I-775 | | Cl | O-i-Bu |
| I-776 | | Cl | OBu |
| I-777 | | Cl | OCH₂C(Me)=CH₂ |
| I-778 | | Cl | OCH₂C₂F₅ |
| I-779 | | Cl | OCH₂CCH |
| I-780 | | Cl | OCH₂CF₃ |
| I-781 | | Cl | OCH₂CH₂C(Me)=CH₂ |
| I-782 | | Cl | OCH₂CH=C(Me)₂ |
| I-783 | | Cl | OCH₂CH=CH₂ |
| I-784 | | Cl | OCH₂CH=CHMe |
| I-785 | | Cl | OEt |
| I-786 | | Cl | OMe |
| I-787 | | Cl | OPr |
| I-788 | | Et | OCH₂C(Me)=CH₂ |
| I-789 | | Et | OCH₂CCH |
| I-790 | | Et | OCH₂CH₂C(Me)=CH₂ |
| I-791 | | Et | OCH₂CH=C(Me)₂ |
| I-792 | | Et | OCH₂CH=CH₂ |
| I-793 | | Et | OCH₂CH=CHMe |
| I-794 | | Me | O-i-Pr |
| I-795 | | Me | OCH₂C(Me)=CH₂ |
| I-796 | | Me | OCH₂CCH |
| I-797 | | Me | OCH₂CH₂C(Me)=CH₂ |
| I-798 | | Me | OCH₂CH=C(Me)₂ |
| I-799 | | Me | OCH₂CH=CH₂ |
| I-800 | | Me | OCH₂CH=CHMe |
| I-801 | | Me | OEt |
| I-802 | | Me | OMe |
| I-803 | | O-i-Bu | O-i-Bu |
| I-804 | | OBu | OBu |
| I-805 | | OCH₂C(Me)=CH₂ | OCH₂C(Me)=CH₂ |

-continued (7/15)

| No. | $X_n$ | $R^1$ | $R^1$ |
|---|---|---|---|
| I-806 | | OCH$_2$CCH | OCH$_2$CCH |
| I-807 | | OCH$_2$CH$_2$C(Me)=CH$_2$ | OCH$_2$CH$_2$C(Me)=CH$_2$ |
| I-808 | | OCH$_2$CH=C(Me)$_2$ | OCH$_2$CH=C(Me)$_2$ |
| I-809 | | OCH$_2$CH=CH$_2$ | OCH$_2$CH=CH$_2$ |
| I-810 | | OCH$_2$CH=CHMe | OCH$_2$CH=CHMe |
| I-811 | | OEt | OEt |
| I-812 | | OMe | OMe |
| I-813 | | OPr | OPr |
| I-814 | | Pr | OCH$_2$C(Me)=CH$_2$ |
| I-815 | | Pr | OCH$_2$CCH |
| I-816 | | Pr | OCH$_2$CH$_2$C(Me)=CH$_2$ |
| I-817 | | Pr | OCH$_2$CH=C(Me)$_2$ |
| I-818 | | Pr | OCH$_2$CH=CH$_2$ |
| I-819 | | Pr | OCH$_2$CH=CHMe |
| I-820 | | i-Pr | OCH$_2$C(Me)=CH$_2$ |
| I-821 | | i-Pr | OCH$_2$CCH |
| I-822 | | i-Pr | OCH$_2$CH$_2$C(Me)=CH$_2$ |
| I-823 | | i-Pr | OCH$_2$CH=C(Me)$_2$ |
| I-824 | | i-Pr | OCH$_2$CH=CH$_2$ |
| I-825 | | i-Pr | OCH$_2$CH=CHMe |
| I-826 | | O-i-Bu | OCH$_2$C(Me)=CH$_2$ |
| I-827 | | O-i-Bu | OCH$_2$CCH |
| I-828 | | O-i-Bu | OCH$_2$CH$_2$C(Me)=CH$_2$ |
| I-829 | | O-i-Bu | OCH$_2$CH=C(Me)$_2$ |
| I-830 | | O-i-Bu | OCH$_2$CH=CH$_2$ |
| I-831 | | O-i-Bu | OCH$_2$CH=CHMe |
| I-832 | | OBu | O-i-Bu |
| I-833 | | OBu | OCH$_2$C(Me)=CH$_2$ |
| I-834 | | OBu | OCH$_2$CCH |
| I-835 | | OBu | OCH$_2$CH$_2$C(Me)=CH$_2$ |
| I-836 | | OBu | OCH$_2$CH=C(Me)$_2$ |
| I-837 | | OBu | OCH$_2$CH=CH$_2$ |
| I-838 | | OBu | OCH$_2$CH=CHMe |
| I-839 | | OCH$_2$CF$_3$ | OCH$_2$C(Me)=CH$_2$ |
| I-840 | | OCH$_2$CF$_3$ | OCH$_2$C$_2$F$_5$ |
| I-841 | | OCH$_2$CF$_3$ | OCH$_2$CCH |
| I-842 | | OCH$_2$CF$_3$ | OCH$_2$CH$_2$C(Me)=CH$_2$ |
| I-843 | | OCH$_2$CF$_3$ | OCH$_2$CH=C(Me)$_2$ |
| I-844 | | OCH$_2$CF$_3$ | OCH$_2$CH=CH$_2$ |
| I-845 | | OCH$_2$CF$_3$ | OCH$_2$CH=CHMe |
| I-846 | | OCH$_2$CH=CH$_2$ | OCH$_2$C(Me)=CH$_2$ |
| I-847 | | OCH$_2$CH=CH$_2$ | OCH$_2$CCH |
| I-848 | | OCH$_2$CH=CH$_2$ | OCH$_2$CH$_2$C(Me)=CH$_2$ |
| I-849 | | OCH$_2$CH=CH$_2$ | OCH$_2$CH=C(Me)$_2$ |
| I-850 | | OCH$_2$CH=CH$_2$ | OCH$_2$CH=CHMe |
| I-851 | | OEt | O-i-Bu |
| I-852 | | OEt | OBu |
| I-853 | | OEt | OCH$_2$C(Me)=CH$_2$ |
| I-854 | | OEt | OCH$_2$CCH |
| I-855 | | OEt | OCH$_2$CH$_2$C(Me)=CH$_2$ |
| I-856 | | OEt | OCH$_2$CH=C(Me)$_2$ |
| I-857 | | OEt | OCH$_2$CH=CH$_2$ |
| I-858 | | OEt | OCH$_2$CH=CHMe |
| I-859 | | OEt | OPr |
| I-860 | | OMe | O-i-Bu |
| I-861 | | OMe | OBu |
| I-862 | | OMe | OCH$_2$C(Me)=CH$_2$ |
| I-863 | | OMe | OCH$_2$CCH |
| I-864 | | OMe | OCH$_2$CH$_2$C(Me)=CH$_2$ |
| I-865 | | OMe | OCH$_2$CH=C(Me)$_2$ |
| I-866 | | OMe | OCH$_2$CH=CH$_2$ |
| I-867 | | OMe | OCH$_2$CH=CHMe |
| I-868 | | OMe | OEt |
| I-869 | | OMe | OPr |
| I-870 | | OPr | O-i-Bu |
| I-871 | | OPr | OBu |
| I-872 | | OPr | OCH$_2$C(Me)=CH$_2$ |
| I-873 | | OPr | OCH$_2$CCH |
| I-874 | | OPr | OCH$_2$CH$_2$C(Me)=CH$_2$ |
| I-875 | | OPr | OCH$_2$CH=C(Me)$_2$ |
| I-876 | | OPr | OCH$_2$CH=CH$_2$ |
| I-877 | | OPr | OCH$_2$CH=CHMe |

TABLE 1

(8/15)

| No. | $X_n$ | $R^1$ | $R^2$ |
|---|---|---|---|
| I-878 | A chlorine atom | OCHF$_2$ | OCHF$_2$ |
| I-879 | at 3-position | CF$_3$ | OCH$_2$C(Me)=CH$_2$ |
| I-880 | (3-Cl) for | CF$_3$ | OCH$_2$CCH |
| I-881 | Compound I-878 | CF$_3$ | OCH$_2$CH$_2$C(Me)=CH$_2$ |
| I-882 | through | CF$_3$ | OCH$_2$CH=C(Me)$_2$ |
| I-883 | Compound I-987 | CF$_3$ | OCH$_2$CH=CH$_2$ |
| I-884 | | CF$_3$ | OCH$_2$CH=CHMe |
| I-885 | | Cl | O-i-Bu |
| I-886 | | Cl | OBu |
| I-887 | | Cl | OCH$_2$C(Me)=CH$_2$ |
| I-888 | | Cl | OCH$_2$C$_2$F$_5$ |
| I-889 | | Cl | OCH$_2$CCH |
| I-890 | | Cl | OCH$_2$CF$_3$ |
| I-891 | | Cl | OCH$_2$CH$_2$C(Me)=CH$_2$ |
| I-892 | | Cl | OCH$_2$CH=C(Me)$_2$ |
| I-893 | | Cl | OCH$_2$CH=CH$_2$ |
| I-894 | | Cl | OCH$_2$CH=CHMe |
| I-895 | | Cl | OEt |
| I-896 | | Cl | OMe |
| I-897 | | Cl | OPr |
| I-898 | | Et | OCH$_2$C(Me)=CH$_2$ |
| I-899 | | Et | OCH$_2$CCH |
| I-900 | | Et | OCH$_2$CH$_2$C(Me)=CH$_2$ |
| I-901 | | Et | OCH$_2$CH=C(Me)$_2$ |
| I-902 | | Et | OCH$_2$CH=CH$_2$ |
| I-903 | | Et | OCH$_2$CH=CHMe |
| I-904 | | Me | O-i-Pr |
| I-905 | | Me | OCH$_2$C(Me)=CH$_2$ |
| I-906 | | Me | OCH$_2$CCH |
| I-907 | | Me | OCH$_2$CH$_2$C(Me)=CH$_2$ |
| I-908 | | Me | OCH$_2$CH=C(Me)$_2$ |
| I-909 | | Me | OCH$_2$CH=CH$_2$ |
| I-910 | | Me | OCH$_2$CH=CHMe |
| I-911 | | Me | OEt |
| I-912 | | Me | OMe |
| I-913 | | O-i-Bu | O-i-Bu |
| I-914 | | OBu | OBu |
| I-915 | | OCH$_2$C(Me)=CH$_2$ | OCH$_2$C(Me)=CH$_2$ |
| I-916 | | OCH$_2$CCH | OCH$_2$CCH |
| I-917 | | OCH$_2$CH$_2$C(Me)=CH$_2$ | OCH$_2$CH$_2$C(Me)=CH$_2$ |
| I-918 | | OCH$_2$CH=C(Me)$_2$ | OCH$_2$CH=C(Me)$_2$ |
| I-919 | | OCH$_2$CH=CH$_2$ | OCH$_2$CH=CH$_2$ |
| I-920 | | OCH$_2$CH=CHMe | OCH$_2$CH=CHMe |
| I-921 | | OEt | OEt |
| I-922 | | OMe | OMe |
| I-923 | | OPr | OPr |
| I-924 | | Pr | OCH$_2$C(Me)=CH$_2$ |
| I-925 | | Pr | OCH$_2$CCH |
| I-926 | | Pr | OCH$_2$CH$_2$C(Me)=CH$_2$ |
| I-927 | | Pr | OCH$_2$CH=C(Me)$_2$ |
| I-928 | | Pr | OCH$_2$CH=CH$_2$ |
| I-929 | | Pr | OCH$_2$CH=CHMe |
| I-930 | | i-Pr | OCH$_2$C(Me)=CH$_2$ |
| I-931 | | i-Pr | OCH$_2$CCH |
| I-932 | | i-Pr | OCH$_2$CH$_2$C(Me)=CH$_2$ |
| I-933 | | i-Pr | OCH$_2$CH=C(Me)$_2$ |
| I-934 | | i-Pr | OCH$_2$CH=CH$_2$ |
| I-935 | | i-Pr | OCH$_2$CH=CHMe |
| I-936 | | O-i-Bu | OCH$_2$C(Me)=CH$_2$ |
| I-937 | | O-i-Bu | OCH$_2$CCH |
| I-938 | | O-i-Bu | OCH$_2$CH$_2$C(Me)=CH$_2$ |
| I-939 | | O-i-Bu | OCH$_2$CH=C(Me)$_2$ |
| I-940 | | O-i-Bu | OCH$_2$CH=CH$_2$ |
| I-941 | | O-i-Bu | OCH$_2$CH=CHMe |
| I-942 | | OBu | O-i-Bu |
| I-943 | | OBu | OCH$_2$C(Me)=CH$_2$ |
| I-944 | | OBu | OCH$_2$CCH |
| I-945 | | OBu | OCH$_2$CH$_2$C(Me)=CH$_2$ |
| I-946 | | OBu | OCH$_2$CH=C(Me)$_2$ |
| I-947 | | OBu | OCH$_2$CH=CH$_2$ |
| I-948 | | OBu | OCH$_2$CH=CHMe |
| I-949 | | OCH$_2$CF$_3$ | OCH$_2$C(Me)=CH$_2$ |
| I-950 | | OCH$_2$CF$_3$ | OCH$_2$C$_2$F$_5$ |
| I-951 | | OCH$_2$CF$_3$ | OCH$_2$CCH |
| I-952 | | OCH$_2$CF$_3$ | OCH$_2$CH$_2$C(Me)=CH$_2$ |

TABLE 1-continued (8/15)

| No. | $X_n$ | $R^1$ | $R^2$ |
|---|---|---|---|
| I-953 | | OCH$_2$CF$_3$ | OCH$_2$CH=C(Me)$_2$ |
| I-954 | | OCH$_2$CF$_3$ | OCH$_2$CH=CH$_2$ |
| I-955 | | OCH$_2$CF$_3$ | OCH$_2$CH=CHMe |
| I-956 | | OCH$_2$CH=CH$_2$ | OCH$_2$C(Me)=CH$_2$ |
| I-957 | | OCH$_2$CH=CH$_2$ | OCH$_2$CCH |
| I-958 | | OCH$_2$CH=CH$_2$ | OCH$_2$CH$_2$C(Me)=CH$_2$ |
| I-959 | | OCH$_2$CH=CH$_2$ | OCH$_2$CH=C(Me)$_2$ |
| I-960 | | OCH$_2$CH=CH$_2$ | OCH$_2$CH=CHMe |
| I-961 | | OEt | O-i-Bu |
| I-962 | | OEt | OBu |
| I-963 | | OEt | OCH$_2$C(Me)=CH$_2$ |
| I-964 | | OEt | OCH$_2$CCH |
| I-965 | | OEt | OCH$_2$CH$_2$C(Me)=CH$_2$ |
| I-966 | | OEt | OCH$_2$CH=C(Me)$_2$ |
| I-967 | | OEt | OCH$_2$CH=CH$_2$ |
| I-968 | | OEt | OCH$_2$CH=CHMe |
| I-969 | | OEt | OPr |
| I-970 | | OMe | O-i-Bu |
| I-971 | | OMe | OBu |
| I-972 | | OMe | OCH$_2$C(Me)=CH$_2$ |
| I-973 | | OMe | OCH$_2$CCH |
| I-974 | | OMe | OCH$_2$CH$_2$C(Me)=CH$_2$ |
| I-975 | | OMe | OCH$_2$CH=C(Me)$_2$ |
| I-976 | | OMe | OCH$_2$CH=CH$_2$ |
| I-977 | | OMe | OCH$_2$CH=CHMe |
| I-978 | | OMe | OEt |
| I-979 | | OMe | OPr |
| I-980 | | OPr | O-i-Bu |
| I-981 | | OPr | OBu |
| I-982 | | OPr | OCH$_2$C(Me)=CH$_2$ |
| I-983 | | OPr | OCH$_2$CCH |
| I-984 | | OPr | OCH$_2$CH$_2$C(Me)=CH$_2$ |
| I-985 | | OPr | OCH$_2$CH=C(Me)$_2$ |
| I-986 | | OPr | OCH$_2$CH=CH$_2$ |
| I-987 | | OPr | OCH$_2$CH=CHMe |

TABLE 1

(9/15)

| No. | $X_n$ | $R^1$ | $R^2$ |
|---|---|---|---|
| I-988 | A fluorine atom | OCHF$_2$ | OCHF$_2$ |
| I-989 | at 3-position | CF$_3$ | OCH$_2$C(Me)=CH$_2$ |
| I-990 | (3-F) for | CF$_3$ | OCH$_2$CCH |
| I-991 | Compound I-988 | CF$_3$ | OCH$_2$CH$_2$C(Me)=CH$_2$ |
| I-992 | through | CF$_3$ | OCH$_2$CH=C(Me)$_2$ |
| I-993 | Compound I-1097 | CF$_3$ | OCH$_2$CH=CH$_2$ |
| I-994 | | CF$_3$ | OCH$_2$CH=CHMe |
| I-995 | | Cl | O-i-Bu |
| I-996 | | Cl | OBu |
| I-997 | | Cl | OCH$_2$C(Me)=CH$_2$ |
| I-998 | | Cl | OCH$_2$C$_2$F$_5$ |
| I-999 | | Cl | OCH$_2$CCH |
| I-1000 | | Cl | OCH$_2$CF$_3$ |
| I-1001 | | Cl | OCH$_2$CH$_2$C(Me)=CH$_2$ |
| I-1002 | | Cl | OCH$_2$CH=C(Me)$_2$ |
| I-1003 | | Cl | OCH$_2$CH=CH$_2$ |
| I-1004 | | Cl | OCH$_2$CH=CHMe |
| I-1005 | | Cl | OEt |
| I-1006 | | Cl | OMe |
| I-1007 | | Cl | OPr |
| I-1008 | | Et | OCH$_2$C(Me)=CH$_2$ |
| I-1009 | | Et | OCH$_2$CCH |
| I-1010 | | Et | OCH$_2$CH$_2$C(Me)=CH$_2$ |
| I-1011 | | Et | OCH$_2$CH=C(Me)2 |
| I-1012 | | Et | OCH$_2$CH=CH$_2$ |
| I-1013 | | Et | OCH$_2$CH=CHMe |
| I-1014 | | Me | O-i-Pr |
| I-1015 | | Me | OCH$_2$C(Me)=CH$_2$ |
| I-1016 | | Me | OCH$_2$CCH |
| I-1017 | | Me | OCH$_2$CH$_2$C(Me)=CH$_2$ |
| I-1018 | | Me | OCH$_2$CH=C(Me)$_2$ |

TABLE 1-continued (9/15)

| No. | $X_n$ | $R^1$ | $R^2$ |
|---|---|---|---|
| I-1019 | | Me | $OCH_2CH=CH_2$ |
| I-1020 | | Me | $OCH_2CH=CHMe$ |
| I-1021 | | Me | OEt |
| I-1022 | | Me | OMe |
| I-1023 | | O-i-Bu | O-i-Bu |
| I-1024 | | OBu | OBu |
| I-1025 | | $OCH_2C(Me)=CH_2$ | $OCH_2C(Me)=CH_2$ |
| I-1026 | | $OCH_2CCH$ | $OCH_2CCH$ |
| I-1027 | | $OCH_2CH_2C(Me)=CH_2$ | $OCH_2CH_2C(Me)=CH_2$ |
| I-1028 | | $OCH_2CH=C(Me)_2$ | $OCH_2CH=C(Me)_2$ |
| I-1029 | | $OCH_2CH=CH_2$ | $OCH_2CH=CH_2$ |
| I-1030 | | $OCH_2CH=CHMe$ | $OCH_2CH=CHMe$ |
| I-1031 | | OEt | OEt |
| I-1032 | | OMe | OMe |
| I-1033 | | OPr | OPr |
| I-1034 | | Pr | $OCH_2C(Me)=CH_2$ |
| I-1035 | | Pr | $OCH_2CCH$ |
| I-1036 | | Pr | $OCH_2CH_2C(Me)=CH_2$ |
| I-1037 | | Pr | $OCH_2CH=C(Me)_2$ |
| I-1038 | | Pr | $OCH_2CH=CH_2$ |
| I-1039 | | Pr | $OCH_2CH=CHMe$ |
| I-1040 | | i-Pr | $OCH_2C(Me)=CH_2$ |
| I-1041 | | i-Pr | $OCH_2CCH$ |
| I-1042 | | i-Pr | $OCH_2CH_2C(Me)=CH_2$ |
| I-1043 | | i-Pr | $OCH_2CH=C(Me)_2$ |
| I-1044 | | i-Pr | $OCH_2CH=CH_2$ |
| I-1045 | | i-Pr | $OCH_2CH=CHMe$ |
| I-1046 | | O-i-Bu | $OCH_2C(Me)=CH_2$ |
| I-1047 | | O-i-Bu | $OCH_2CCH$ |
| I-1048 | | O-i-Bu | $OCH_2CH_2C(Me)=CH_2$ |
| I-1049 | | O-i-Bu | $OCH_2CH=C(Me)_2$ |
| I-1050 | | O-i-Bu | $OCH_2CH=CH_2$ |
| I-1051 | | O-i-Bu | $OCH_2CH=CHMe$ |
| I-1052 | | OBu | O-i-Bu |
| I-1053 | | OBu | $OCH_2C(Me)=CH_2$ |
| I-1054 | | OBu | $OCH_2CCH$ |
| I-1055 | | OBu | $OCH_2CH_2C(Me)=CH_2$ |
| I-1056 | | OBu | $OCH_2CH=C(Me)_2$ |
| I-1057 | | OBu | $OCH_2CH=CH_2$ |
| I-1058 | | OBu | $OCH_2CH=CHMe$ |
| I-1059 | | $OCH_2CF_3$ | $OCH_2C(Me)=CH_2$ |
| I-1060 | | $OCH_2CF_3$ | $OCH_2C_2F_5$ |
| I-1061 | | $OCH_2CF_3$ | $OCH_2CCH$ |
| I-1062 | | $OCH_2CF_3$ | $OCH_2CH_2C(Me)=CH_2$ |
| I-1063 | | $OCH_2CF_3$ | $OCH_2CH=C(Me)_2$ |
| I-1064 | | $OCH_2CF_3$ | $OCH_2CH=CH_2$ |
| I-1065 | | $OCH_2CF_3$ | $OCH_2CH=CHMe$ |
| I-1066 | | $OCH_2CH=CH_2$ | $OCH_2C(Me)=CH_2$ |
| I-1067 | | $OCH_2CH=CH_2$ | $OCH_2CCH$ |
| I-1068 | | $OCH_2CH=CH_2$ | $OCH_2CH_2C(Me)=CH_2$ |
| I-1069 | | $OCH_2CH=CH_2$ | $OCH_2CH=C(Me)_2$ |
| I-1070 | | $OCH_2CH=CH_2$ | $OCH_2CH=CHMe$ |
| I-1071 | | OEt | O-i-Bu |
| I-1072 | | OEt | OBu |
| I-1073 | | OEt | $OCH_2C(Me)=CH_2$ |
| I-1074 | | OEt | $OCH_2CCH$ |
| I-1075 | | OEt | $OCH_2CH_2C(Me)=CH_2$ |
| I-1076 | | OEt | $OCH_2CH=C(Me)_2$ |
| I-1077 | | OEt | $OCH_2CH=CH_2$ |
| I-1078 | | OEt | $OCH_2CH=CHMe$ |
| I-1079 | | OEt | OPr |
| I-1080 | | OMe | O-i-Bu |
| I-1081 | | OMe | OBu |
| I-1082 | | OMe | $OCH_2C(Me)=CH_2$ |
| I-1083 | | OMe | $OCH_2CCH$ |
| I-1084 | | OMe | $OCH_2CH_2C(Me)=CH_2$ |
| I-1085 | | OMe | $OCH_2CH=C(Me)2$ |
| I-1086 | | OMe | $OCH_2CH=CH_2$ |
| I-1087 | | OMe | $OCH_2CH=CHMe$ |
| I-1088 | | OMe | OEt |
| I-1089 | | OMe | OPr |
| I-1090 | | OPr | O-i-Bu |
| I-1091 | | OPr | OBu |
| I-1092 | | OPr | $OCH_2C(Me)=CH_2$ |
| I-1093 | | OPr | $OCH_2CCH$ |

TABLE 1-continued (9/15)

| No. | $X_n$ | $R^1$ | $R^2$ |
|---|---|---|---|
| I-1094 | | OPr | $OCH_2CH_2C(Me)=CH_2$ |
| I-1095 | | OPr | $OCH_2CH=C(Me)_2$ |
| I-1096 | | OPr | $OCH_2CH=CH_2$ |
| I-1097 | | OPr | $OCH_2CH=CHMe$ |

TABLE 1

(10/15)

| No. | $X_n$ | $R^1$ | $R^2$ |
|---|---|---|---|
| I-1098 | A bromine atom | $OCHF_2$ | $OCHF_2$ |
| I-1099 | at 3-position | $CF_3$ | $OCH_2C(Me)=CH_2$ |
| I-1100 | (3-Br) for | $CF_3$ | $OCH_2CCH$ |
| I-1101 | Compound I-1098 | $CF_3$ | $OCH_2CH_2C(Me)=CH_2$ |
| I-1102 | through | $CF_3$ | $OCH_2CH=C(Me)_2$ |
| I-1103 | Compound I-1207 | $CF_3$ | $OCH_2CH=CH_2$ |
| I-1104 | | $CF_3$ | $OCH_2CH=CHMe$ |
| I-1105 | | Cl | O-i-Bu |
| I-1106 | | Cl | OBu |
| I-1107 | | Cl | $OCH_2C(Me)=CH_2$ |
| I-1108 | | Cl | $OCH_2C_2F_5$ |
| I-1109 | | Cl | $OCH_2CCH$ |
| I-1110 | | Cl | $OCH_2CF_3$ |
| I-1111 | | Cl | $OCH_2CH_2C(Me)=CH_2$ |
| I-1112 | | Cl | $OCH_2CH=C(Me)_2$ |
| I-1113 | | Cl | $OCH_2CH=CH_2$ |
| I-1114 | | Cl | $OCH_2CH=CHMe$ |
| I-1115 | | Cl | OEt |
| I-1116 | | Cl | OMe |
| I-1117 | | Cl | OPr |
| I-1118 | | Et | $OCH_2C(Me)=CH_2$ |
| I-1119 | | Et | $OCH_2CCH$ |
| I-1120 | | Et | $OCH_2CH_2C(Me)=CH_2$ |
| I-1121 | | Et | $OCH_2CH=C(Me)_2$ |
| I-1122 | | Et | $OCH_2CH=CH_2$ |
| I-1123 | | Et | $OCH_2CH=CHMe$ |
| I-1124 | | Me | O-i-Pr |
| I-1125 | | Me | $OCH_2C(Me)=CH_2$ |
| I-1126 | | Me | $OCH_2CCH$ |
| I-1127 | | Me | $OCH_2CH_2C(Me)=CH_2$ |
| I-1128 | | Me | $OCH_2CH=C(Me)_2$ |
| I-1129 | | Me | $OCH_2CH=CH_2$ |
| I-1130 | | Me | $OCH_2CH=CHMe$ |
| I-1131 | | Me | OEt |
| I-1132 | | Me | OMe |
| I-1133 | | O-i-Bu | O-i-Bu |
| I-1134 | | OBu | OBu |
| I-1135 | | $OCH_2C(Me)=CH_2$ | $OCH_2C(Me)=CH_2$ |
| I-1136 | | $OCH_2CCH$ | $OCH_2CCH$ |
| I-1137 | | $OCH_2CH_2C(Me)=CH_2$ | $OCH_2CH_2C(Me)=CH_2$ |
| I-1138 | | $OCH_2CH=C(Me)_2$ | $OCH_2CH=C(Me)2$ |
| I-1139 | | $OCH_2CH=CH_2$ | $OCH_2CH=CH_2$ |
| I-1140 | | $OCH_2CH=CHMe$ | $OCH_2CH=CHMe$ |
| I-1141 | | OEt | OEt |
| I-1142 | | OMe | OMe |
| I-1143 | | OPr | OPr |
| I-1144 | | Pr | $OCH_2C(Me)=CH_2$ |
| I-1145 | | Pr | $OCH_2CCH$ |
| I-1146 | | Pr | $OCH_2CH_2C(Me)=CH_2$ |
| I-1147 | | Pr | $OCH_2CH=C(Me)_2$ |
| I-1148 | | Pr | $OCH_2CH=CH_2$ |
| I-1149 | | Pr | $OCH_2CH=CHMe$ |
| I-1150 | | i-Pr | $OCH_2C(Me)=CH_2$ |
| I-1151 | | i-Pr | $OCH_2CCH$ |
| I-1152 | | i-Pr | $OCH_2CH_2C(Me)=CH_2$ |
| I-1153 | | i-Pr | $OCH_2CH=C(Me)_2$ |
| I-1154 | | i-Pr | $OCH_2CH=CH_2$ |
| I-1155 | | i-Pr | $OCH_2CH=CHMe$ |
| I-1156 | | O-i-Bu | $OCH_2C(Me)=CH_2$ |
| I-1157 | | O-i-Bu | $OCH_2CCH$ |
| I-1158 | | O-i-Bu | $OCH_2CH_2C(Me)=CH_2$ |
| I-1159 | | O-i-Bu | $OCH_2CH=C(Me)_2$ |

TABLE 1-continued (10/15)

| No. | $X_n$ | $R^1$ | $R^2$ |
|---|---|---|---|
| I-1160 | | O-i-Bu | OCH$_2$CH=CH$_2$ |
| I-1161 | | O-i-Bu | OCH$_2$CH=CHMe |
| I-1162 | | OBu | O-i-Bu |
| I-1163 | | OBu | OCH$_2$C(Me)=CH$_2$ |
| I-1164 | | OBu | OCH$_2$CCH |
| I-1165 | | OBu | OCH$_2$CH$_2$C(Me)=CH$_2$ |
| I-1166 | | OBu | OCH$_2$CH=C(Me)$_2$ |
| I-1167 | | OBu | OCH$_2$CH=CH$_2$ |
| I-1168 | | OBu | OCH$_2$CH=CHMe |
| I-1169 | | OCH$_2$CF$_3$ | OCH$_2$C(Me)=CH$_2$ |
| I-1170 | | OCH$_2$CF$_3$ | OCH$_2$C$_2$F$_5$ |
| I-1171 | | OCH$_2$CF$_3$ | OCH$_2$CCH |
| I-1172 | | OCH$_2$CF$_3$ | OCH$_2$CH$_2$C(Me)=CH$_2$ |
| I-1173 | | OCH$_2$CF$_3$ | OCH$_2$CH=C(Me)$_2$ |
| I-1174 | | OCH$_2$CF$_3$ | OCH$_2$CH=CH$_2$ |
| I-1175 | | OCH$_2$CF$_3$ | OCH$_2$CH=CHMe |
| I-1176 | | OCH$_2$CH=CH$_2$ | OCH$_2$C(Me)=CH$_2$ |
| I-1177 | | OCH$_2$CH=CH$_2$ | OCH$_2$CCH |
| I-1178 | | OCH$_2$CH=CH$_2$ | OCH$_2$CH$_2$C(Me)=CH$_2$ |
| I-1179 | | OCH$_2$CH=CH$_2$ | OCH$_2$CH=C(Me)$_2$ |
| I-1180 | | OCH$_2$CH=CH$_2$ | OCH$_2$CH=CHMe |
| I-1181 | | OEt | O-i-Bu |
| I-1182 | | OEt | OBu |
| I-1183 | | OEt | OCH$_2$C(Me)=CH$_2$ |
| I-1184 | | OEt | OCH$_2$CCH |
| I-1185 | | OEt | OCH$_2$CH$_2$C(Me)=CH$_2$ |
| I-1186 | | OEt | OCH$_2$CH=C(Me)$_2$ |
| I-1187 | | OEt | OCH$_2$CH=CH$_2$ |
| I-1188 | | OEt | OCH$_2$CH=CHMe |
| I-1189 | | OEt | OPr |
| I-1190 | | OMe | O-i-Bu |
| I-1191 | | OMe | OBu |
| I-1192 | | OMe | OCH$_2$C(Me)=CH$_2$ |
| I-1193 | | OMe | OCH$_2$CCH |
| I-1194 | | OMe | OCH$_2$CH$_2$C(Me)=CH$_2$ |
| I-1195 | | OMe | OCH$_2$CH=C(Me)$_2$ |
| I-1196 | | OMe | OCH$_2$CH=CH$_2$ |
| I-1197 | | OMe | OCH$_2$CH=CHMe |
| I-1198 | | OMe | OEt |
| I-1199 | | OMe | OPr |
| I-1200 | | OPr | O-i-Bu |
| I-1201 | | OPr | OBu |
| I-1202 | | OPr | OCH$_2$C(Me)=CH$_2$ |
| I-1203 | | OPr | OCH$_2$CCH |
| I-1204 | | OPr | OCH$_2$CH$_2$C(Me)=CH$_2$ |
| I-1205 | | OPr | OCH$_2$CH=C(Me)$_2$ |
| I-1206 | | OPr | OCH$_2$CH=CH$_2$ |
| I-1207 | | OPr | OCH$_2$CH=CHMe |

TABLE 1

(11/15)

| No. | $X_n$ | $R^1$ | $R^2$ |
|---|---|---|---|
| I-1208 | A methyl group | OCHF$_2$ | OCHF$_2$ |
| I-1209 | at 3-position | CF$_3$ | OCH$_2$C(Me)=CH$_2$ |
| I-1210 | (2-Me) for | CF$_3$ | OCH$_2$CCH |
| I-1211 | Compound I-1208 | CF$_3$ | OCH$_2$CH$_2$C(Me)=CH$_2$ |
| I-1212 | through | CF$_3$ | OCH$_2$CH=C(Me)$_2$ |
| I-1213 | Compound I-1317 | CF$_3$ | OCH$_2$CH=CH$_2$ |
| I-1214 | | CF$_3$ | OCH$_2$CH=CHMe |
| I-1215 | | Cl | O-i-Bu |
| I-1216 | | Cl | OBu |
| I-1217 | | Cl | OCH$_2$C(Me)=CH$_2$ |
| I-1218 | | Cl | OCH$_2$C$_2$F$_5$ |
| I-1219 | | Cl | OCH$_2$CCH |
| I-1220 | | Cl | OCH$_2$CF$_3$ |
| I-1221 | | Cl | OCH$_2$CH$_2$C(Me)=CH$_2$ |
| I-1222 | | Cl | OCH$_2$CH=C(Me)$_2$ |
| I-1223 | | Cl | OCH$_2$CH=CH$_2$ |
| I-1224 | | Cl | OCH$_2$CH=CHMe |
| I-1225 | | Cl | OEt |

TABLE 1-continued (11/15)

| No. | $X_n$ | $R^1$ | $R^2$ |
|---|---|---|---|
| I-1226 | | Cl | OMe |
| I-1227 | | Cl | OPr |
| I-1228 | | Et | $OCH_2C(Me)=CH_2$ |
| I-1229 | | Et | $OCH_2CCH$ |
| I-1230 | | Et | $OCH_2CH_2C(Me)=CH_2$ |
| I-1231 | | Et | $OCH_2CH=C(Me)_2$ |
| I-1232 | | Et | $OCH_2CH=CH_2$ |
| I-1233 | | Et | $OCH_2CH=CHMe$ |
| I-1234 | | Me | O-i-Pr |
| I-1235 | | Me | $OCH_2C(Me)=CH_2$ |
| I-1236 | | Me | $OCH_2CCH$ |
| I-1237 | | Me | $OCH_2CH_2C(Me)=CH_2$ |
| I-1238 | | Me | $OCH_2CH=C(Me)_2$ |
| I-1239 | | Me | $OCH_2CH=CH_2$ |
| I-1240 | | Me | $OCH_2CH=CHMe$ |
| I-1241 | | Me | OEt |
| I-1242 | | Me | OMe |
| I-1243 | | O-i-Bu | O-i-Bu |
| I-1244 | | OBu | OBu |
| I-1245 | | $OCH_2C(Me)=CH_2$ | $OCH_2C(Me)=CH_2$ |
| I-1246 | | $OCH_2CCH$ | $OCH_2CCH$ |
| I-1247 | | $OCH_2CH_2C(Me)=CH_2$ | $OCH_2CH_2C(Me)=CH_2$ |
| I-1248 | | $OCH_2CH=C(Me)_2$ | $OCH_2CH=C(Me)_2$ |
| I-1249 | | $OCH_2CH=CH_2$ | $OCH_2CH=CH_2$ |
| I-1250 | | $OCH_2CH=CHMe$ | $OCH_2CH=CHMe$ |
| I-1251 | | OEt | OEt |
| I-1252 | | OMe | OMe |
| I-1253 | | OPr | OPr |
| I-1254 | | Pr | $OCH_2C(Me)=CH_2$ |
| I-1255 | | Pr | $OCH_2CCH$ |
| I-1256 | | Pr | $OCH_2CH_2C(Me)=CH_2$ |
| I-1257 | | Pr | $OCH_2CH=C(Me)_2$ |
| I-1258 | | Pr | $OCH_2CH=CH_2$ |
| I-1259 | | Pr | $OCH_2CH=CHMe$ |
| I-1260 | | i-Pr | $OCH_2C(Me)=CH_2$ |
| I-1261 | | i-Pr | $OCH_2CCH$ |
| I-1262 | | i-Pr | $OCH_2CH_2C(Me)=CH_2$ |
| I-1263 | | i-Pr | $OCH_2CH=C(Me)_2$ |
| I-1264 | | i-Pr | $OCH_2CH=CH_2$ |
| I-1265 | | i-Pr | $OCH_2CH=CHMe$ |
| I-1266 | | O-i-Bu | $OCH_2C(Me)=CH_2$ |
| I-1267 | | O-i-Bu | $OCH_2CCH$ |
| I-1268 | | O-i-Bu | $OCH_2CH_2C(Me)=CH_2$ |
| I-1269 | | O-i-Bu | $OCH_2CH=C(Me)_2$ |
| I-1270 | | O-i-Bu | $OCH_2CH=CH_2$ |
| I-1271 | | O-i-Bu | $OCH_2CH=CHMe$ |
| I-1272 | | OBu | O-i-Bu |
| I-1273 | | OBu | $OCH_2C(Me)=CH_2$ |
| I-1274 | | OBu | $OCH_2CCH$ |
| I-1275 | | OBu | $OCH_2CH_2C(Me)=CH_2$ |
| I-1276 | | OBu | $OCH_2CH=C(Me)_2$ |
| I-1277 | | OBu | $OCH_2CH=CH_2$ |
| I-1278 | | OBu | $OCH_2CH=CHMe$ |
| I-1279 | | $OCH_2CF_3$ | $OCH_2C(Me)=CH_2$ |
| I-1280 | | $OCH_2CF_3$ | $OCH_2C_2F_5$ |
| I-1281 | | $OCH_2CF_3$ | $OCH_2CCH$ |
| I-1282 | | $OCH_2CF_3$ | $OCH_2CH_2C(Me)=CH_2$ |
| I-1283 | | $OCH_2CF_3$ | $OCH_2CH=C(Me)2$ |
| I-1284 | | $OCH_2CF_3$ | $OCH_2CH=CH_2$ |
| I-1285 | | $OCH_2CF_3$ | $OCH_2CH=CHMe$ |
| I-1286 | | $OCH_2CH=CH_2$ | $OCH_2C(Me)=CH_2$ |
| I-1287 | | $OCH_2CH=CH_2$ | $OCH_2CCH$ |
| I-1288 | | $OCH_2CH=CH_2$ | $OCH_2CH_2C(Me)=CH_2$ |
| I-1289 | | $OCH_2CH=CH_2$ | $OCH_2CH=C(Me)_2$ |
| I-1290 | | $OCH_2CH=CH_2$ | $OCH_2CH=CHMe$ |
| I-1291 | | OEt | O-i-Bu |
| I-1292 | | OEt | OBu |
| I-1293 | | OEt | $OCH_2C(Me)=CH_2$ |
| I-1294 | | OEt | $OCH_2CCH$ |
| I-1295 | | OEt | $OCH_2CH_2C(Me)=CH_2$ |
| I-1296 | | OEt | $OCH_2CH=C(Me)_2$ |
| I-1297 | | OEt | $OCH_2CH=CH_2$ |
| I-1298 | | OEt | $OCH_2CH=CHMe$ |
| I-1299 | | OEt | OPr |
| I-1300 | | OMe | O-i-Bu |

TABLE 1-continued (11/15)

| No. | $X_n$ | $R^1$ | $R^2$ |
|---|---|---|---|
| I-1301 | | OMe | OBu |
| I-1302 | | OMe | $OCH_2C(Me)=CH_2$ |
| I-1303 | | OMe | $OCH_2CCH$ |
| I-1304 | | OMe | $OCH_2CH_2C(Me)=CH_2$ |
| I-1305 | | OMe | $OCH_2CH=C(Me)_2$ |
| I-1306 | | OMe | $OCH_2CH=CH_2$ |
| I-1307 | | OMe | $OCH_2CH=CHMe$ |
| I-1308 | | OMe | OEt |
| I-1309 | | OMe | OPr |
| I-1310 | | OPr | O-i-Bu |
| I-1311 | | OPr | OBu |
| I-1312 | | OPr | $OCH_2C(Me)=CH_2$ |
| I-1313 | | OPr | $OCH_2CCH$ |
| I-1314 | | OPr | $OCH_2CH_2C(Me)=CH_2$ |
| I-1315 | | OPr | $OCH_2CH=C(Me)_2$ |
| I-1316 | | OPr | $OCH_2CH=CH_2$ |
| I-1317 | | OPr | $OCH_2CH=CHMe$ |

TABLE 1

(12/15)

| No. | $X_n$ | $R^1$ | $R^2$ |
|---|---|---|---|
| I-1318 | A chlorine atom | $OCHF_2$ | $OCHF_2$ |
| I-1319 | at 4-position | $CF_3$ | $OCH_2C(Me)=CH_2$ |
| I-1320 | (4-Cl) for | $CF_3$ | $OCH_2CCH$ |
| I-1321 | Compound I-768 | $CF_3$ | $OCH_2CH_2C(Me)=CH_2$ |
| I-1322 | through | $CF_3$ | $OCH_2CH=C(Me)2$ |
| I-1323 | Compound I-877 | $CF_3$ | $OCH_2CH=CH_2$ |
| I-1324 | | $CF_3$ | $OCH_2CH=CHMe$ |
| I-1325 | | Cl | O-i-Bu |
| I-1326 | | Cl | OBu |
| I-1327 | | Cl | $OCH_2C(Me)=CH_2$ |
| I-1328 | | Cl | $OCH_2C_2F_5$ |
| I-1329 | | Cl | $OCH_2CCH$ |
| I-1330 | | Cl | $OCH_2CF_3$ |
| I-1331 | | Cl | $OCH_2CH_2C(Me)=CH_2$ |
| I-1332 | | Cl | $OCH_2CH=C(Me)_2$ |
| I-1333 | | Cl | $OCH_2CH=CH_2$ |
| I-1334 | | Cl | $OCH_2CH=CHMe$ |
| I-1335 | | Cl | OEt |
| I-1336 | | Cl | OMe |
| I-1337 | | Cl | OPr |
| I-1338 | | Et | $OCH_2C(Me)=CH_2$ |
| I-1339 | | Et | $OCH_2CCH$ |
| I-1340 | | Et | $OCH_2CH_2C(Me)=CH_2$ |
| I-1341 | | Et | $OCH_2CH=C(Me)_2$ |
| I-1342 | | Et | $OCH_2CH=CH_2$ |
| I-1343 | | Et | $OCH_2CH=CHMe$ |
| I-1344 | | Me | O-i-Pr |
| I-1345 | | Me | $OCH_2C(Me)=CH_2$ |
| I-1346 | | Me | $OCH_2CCH$ |
| I-1347 | | Me | $OCH_2CH_2C(Me)=CH_2$ |
| I-1348 | | Me | $OCH_2CH=C(Me)_2$ |
| I-1349 | | Me | $OCH_2CH=CH_2$ |
| I-1350 | | Me | $OCH_2CH=CHMe$ |
| I-1351 | | Me | OEt |
| I-1352 | | Me | OMe |
| I-1353 | | O-i-Bu | O-i-Bu |
| I-1354 | | OBu | OBu |
| I-1355 | | $OCH_2C(Me)=CH_2$ | $OCH_2C(Me)=CH_2$ |
| I-1356 | | $OCH_2CCH$ | $OCH_2CCH$ |
| I-1357 | | $OCH_2CH_2C(Me)=CH_2$ | $OCH_2CH_2C(Me)=CH_2$ |
| I-1358 | | $OCH_2CH=C(Me)_2$ | $OCH_2CH=C(Me)_2$ |
| I-1359 | | $OCH_2CH=CH_2$ | $OCH_2CH=CH_2$ |
| I-1360 | | $OCH_2CH=CHMe$ | $OCH_2CH=CHMe$ |
| I-1361 | | OEt | OEt |
| I-1362 | | OMe | OMe |
| I-1363 | | OPr | OPr |
| I-1364 | | Pr | $OCH_2C(Me)=CH_2$ |
| I-1365 | | Pr | $OCH_2CCH$ |
| I-1366 | | Pr | $OCH_2CH_2C(Me)=CH_2$ |

TABLE 1-continued (12/15)

| No. | $X_n$ | $R^1$ | $R^2$ |
|---|---|---|---|
| I-1367 | | Pr | $OCH_2CH=C(Me)_2$ |
| I-1368 | | Pr | $OCH_2CH=CH_2$ |
| I-1369 | | Pr | $OCH_2CH=CHMe$ |
| I-1370 | | i-Pr | $OCH_2C(Me)=CH_2$ |
| I-1371 | | i-Pr | $OCH_2CCH$ |
| I-1372 | | i-Pr | $OCH_2CH_2C(Me)=CH_2$ |
| I-1373 | | i-Pr | $OCH_2CH=C(Me)_2$ |
| I-1374 | | i-Pr | $OCH_2CH=CH_2$ |
| I-1375 | | i-Pr | $OCH_2CH=CHMe$ |
| I-1376 | | O-i-Bu | $OCH_2C(Me)=CH_2$ |
| I-1377 | | O-i-Bu | $OCH_2CCH$ |
| I-1378 | | O-i-Bu | $OCH_2CH_2C(Me)=CH_2$ |
| I-1379 | | O-i-Bu | $OCH_2CH=C(Me)_2$ |
| I-1380 | | O-i-Bu | $OCH_2CH=CH_2$ |
| I-1381 | | O-i-Bu | $OCH_2CH=CHMe$ |
| I-1382 | | OBu | O-i-Bu |
| I-1383 | | OBu | $OCH_2C(Me)=CH_2$ |
| I-1384 | | OBu | $OCH_2CCH$ |
| I-1385 | | OBu | $OCH_2CH_2C(Me)=CH_2$ |
| I-1386 | | OBu | $OCH_2CH=C(Me)_2$ |
| I-1387 | | OBu | $OCH_2CH=CH_2$ |
| I-1388 | | OBu | $OCH_2CH=CHMe$ |
| I-1389 | | $OCH_2CF_3$ | $OCH_2C(Me)=CH_2$ |
| I-1390 | | $OCH_2CF_3$ | $OCH_2C_2F_5$ |
| I-1391 | | $OCH_2CF_3$ | $OCH_2CCH$ |
| I-1392 | | $OCH_2CF_3$ | $OCH_2CH_2C(Me)=CH_2$ |
| I-1393 | | $OCH_2CF_3$ | $OCH_2CH=C(Me)_2$ |
| I-1394 | | $OCH_2CF_3$ | $OCH_2CH=CH_2$ |
| I-1395 | | $OCH_2CF_3$ | $OCH_2CH=CHMe$ |
| I-1396 | | $OCH_2CH=CH_2$ | $OCH_2C(Me)=CH_2$ |
| I-1397 | | $OCH_2CH=CH_2$ | $OCH_2CCH$ |
| I-1398 | | $OCH_2CH=CH_2$ | $OCH_2CH_2C(Me)=CH_2$ |
| I-1399 | | $OCH_2CH=CH_2$ | $OCH_2CH=C(Me)_2$ |
| I-1400 | | $OCH_2CH=CH_2$ | $OCH_2CH=CHMe$ |
| I-1401 | | OEt | O-i-Bu |
| I-1402 | | OEt | OBu |
| I-1403 | | OEt | $OCH_2C(Me)=CH_2$ |
| I-1404 | | OEt | $OCH_2CCH$ |
| I-1405 | | OEt | $OCH_2CH_2C(Me)=CH_2$ |
| I-1406 | | OEt | $OCH_2CH=C(Me)_2$ |
| I-1407 | | OEt | $OCH_2CH=CH_2$ |
| I-1408 | | OEt | $OCH_2CH=CHMe$ |
| I-1409 | | OEt | OPr |
| I-1410 | | OMe | O-i-Bu |
| I-1411 | | OMe | OBu |
| I-1412 | | OMe | $OCH_2C(Me)=CH_2$ |
| I-1413 | | OMe | $OCH_2CCH$ |
| I-1414 | | OMe | $OCH_2CH_2C(Me)=CH_2$ |
| I-1415 | | OMe | $OCH_2CH=C(Me)_2$ |
| I-1416 | | OMe | $OCH_2CH=CH_2$ |
| I-1417 | | OMe | $OCH_2CH=CHMe$ |
| I-1418 | | OMe | OEt |
| I-1419 | | OMe | OPr |
| I-1420 | | OPr | O-i-Bu |
| I-1421 | | OPr | OBu |
| I-1422 | | OPr | $OCH_2C(Me)=CH_2$ |
| I-1423 | | OPr | $OCH_2CCH$ |
| I-1424 | | OPr | $OCH_2CH_2C(Me)=CH_2$ |
| I-1425 | | OPr | $OCH_2CH=C(Me)_2$ |
| I-1426 | | OPr | $OCH_2CH=CH_2$ |
| I-1427 | | OPr | $OCH_2CH=CHMe$ |
| I-2021 | A chlorine atom | Me | SMe |
| I-2022 | at 4-position | Me | SEt |
| I-2023 | (4-Cl) for | Me | SPr |
| I-2024 | Compound I-2021 | OMe | SMe |
| I-2025 | through | OMe | SEt |
| I-2026 | Compound I-2035 | OMe | SPr |
| I-2027 | | SMe | SMe |
| I-2028 | | SEt | SEt |
| I-2029 | | SPr | iSPr |
| I-2030 | | $OCH_2CH=CH_2$ | SMe |
| I-2031 | | $OCH_2CH=CH_2$ | SEt |
| I-2032 | | $OCH_2CH-CH_2$ | SPr |
| I-2033 | | Cl | SMe |

TABLE 1-continued (12/15)

| No. | $X_n$ | $R^1$ | $R^2$ |
|---|---|---|---|
| I-2034 | | Cl | SEt |
| I-2035 | | Cl | SPr |

TABLE 1

(13/15)

| No. | $X_n$ | $R^1$ | $R^2$ |
|---|---|---|---|
| I-1428 | A fluorine atom | OCHF$_2$ | OCHF$_2$ |
| I-1429 | at 4-position | CF$_3$ | OCH$_2$C(Me)=CH$_2$ |
| I-1430 | (4-F) for | CF$_3$ | OCH$_2$CCH |
| I-1431 | Compound I-1428 | CF$_3$ | OCH$_2$CH$_2$C(Me)=CH$_2$ |
| I-1432 | through | CF$_3$ | OCH$_2$CH=C(Me)$_2$ |
| I-1433 | Compound I-1537 | CF$_3$ | OCH$_2$CH=CH$_2$ |
| I-1434 | | CF$_3$ | OCH$_2$CH=CHMe |
| I-1435 | | Cl | O-i-Bu |
| I-1436 | | Cl | OBu |
| I-1437 | | Cl | OCH$_2$C(Me)=CH$_2$ |
| I-1438 | | Cl | OCH$_2$C$_2$F$_5$ |
| I-1439 | | Cl | OCH$_2$CCH |
| I-1440 | | Cl | OCH$_2$CF$_3$ |
| I-1441 | | Cl | OCH$_2$CH$_2$C(Me)=CH$_2$ |
| I-1442 | | Cl | OCH$_2$CH=C(Me)$_2$ |
| I-1443 | | Cl | OCH$_2$CH=CH$_2$ |
| I-1444 | | Cl | OCH$_2$CH=CHMe |
| I-1445 | | Cl | OEt |
| I-1446 | | Cl | OMe |
| I-1447 | | Cl | OPr |
| I-1448 | | Et | OCH$_2$C(Me)=CH$_2$ |
| I-1449 | | Et | OCH$_2$CCH |
| I-1450 | | Et | OCH$_2$CH$_2$C(Me)=CH$_2$ |
| I-1451 | | Et | OCH$_2$CH=C(Me)$_2$ |
| I-1452 | | Et | OCH$_2$CH=CH$_2$ |
| I-1453 | | Et | OCH$_2$CH=CHMe |
| I-1454 | | Me | O-i-Pr |
| I-1455 | | Me | OCH$_2$C(Me)=CH$_2$ |
| I-1456 | | Me | OCH$_2$CCH |
| I-1457 | | Me | OCH$_2$CH$_2$C(Me)=CH$_2$ |
| I-1458 | | Me | OCH$_2$CH=C(Me)$_2$ |
| I-1459 | | Me | OCH$_2$CH=CH$_2$ |
| I-1460 | | Me | OCH$_2$CH=CHMe |
| I-1461 | | Me | OEt |
| I-1462 | | Me | OMe |
| I-1463 | | O-i-Bu | O-i-Bu |
| I-1464 | | OBu | OBu |
| I-1465 | | OCH$_2$C(Me)=CH$_2$ | OCH$_2$C(Me)=CH$_2$ |
| I-1466 | | OCH$_2$CCH | OCH$_2$CCH |
| I-1467 | | OCH$_2$CH$_2$C(Me)=CH$_2$ | OCH$_2$CH$_2$C(Me)=CH$_2$ |
| I-1468 | | OCH$_2$CH=C(Me)$_2$ | OCH$_2$CH=C(Me)$_2$ |
| I-1469 | | OCH$_2$CH=CH$_2$ | OCH$_2$CH=CH$_2$ |
| I-1470 | | OCH$_2$CH=CHMe | OCH$_2$CH=CHMe |
| I-1471 | | OEt | OEt |
| I-1472 | | OMe | OMe |
| I-1473 | | OPr | OPr |
| I-1474 | | Pr | OCH$_2$C(Me)=CH$_2$ |
| I-1475 | | Pr | OCH$_2$CCH |
| I-1476 | | Pr | OCH$_2$CH$_2$C(Me)=CH$_2$ |
| I-1477 | | Pr | OCH$_2$CH=C(Me)$_2$ |
| I-1478 | | Pr | OCH$_2$CH=CH$_2$ |
| I-1479 | | Pr | OCH$_2$CH=CHMe |
| I-1480 | | i-Pr | OCH$_2$C(Me)=CH$_2$ |
| I-1481 | | i-Pr | OCH$_2$CCH |
| I-1482 | | i-Pr | OCH$_2$CH$_2$C(Me)=CH$_2$ |
| I-1483 | | i-Pr | OCH$_2$CH=C(Me)$_2$ |
| I-1484 | | i-Pr | OCH$_2$CH=CH$_2$ |
| I-1485 | | i-Pr | OCH$_2$CH=CHMe |
| I-1486 | | O-i-Bu | OCH$_2$C(Me)=CH$_2$ |
| I-1487 | | O-i-Bu | OCH$_2$CCH |
| I-1488 | | O-i-Bu | OCH$_2$CH$_2$C(Me)=CH$_2$ |
| I-1489 | | O-i-Bu | OCH$_2$CH=C(Me)$_2$ |
| I-1490 | | O-i-Bu | OCH$_2$CH=CH$_2$ |
| I-1491 | | O-i-Bu | OCH$_2$CH=CHMe |

TABLE 1-continued (13/15)

| No. | X$_n$ | R$^1$ | R$^2$ |
|---|---|---|---|
| I-1492 | | OBu | O-i-Bu |
| I-1493 | | OBu | OCH$_2$C(Me)=CH$_2$ |
| I-1494 | | OBu | OCH$_2$CCH |
| I-1495 | | OBu | OCH$_2$CH$_2$C(Me)=CH$_2$ |
| I-1496 | | OBu | OCH$_2$CH=C(Me)$_2$ |
| I-1497 | | OBu | OCH$_2$CH=CH$_2$ |
| I-1498 | | OBu | OCH$_2$CH=CHMe |
| I-1499 | | OCH$_2$CF$_3$ | OCH$_2$C(Me)=CH$_2$ |
| I-1500 | | OCH$_2$CF$_3$ | OCH$_2$C$_2$F$_5$ |
| I-1501 | | OCH$_2$CF$_3$ | OCH$_2$CCH |
| I-1502 | | OCH$_2$CF$_3$ | OCH$_2$CH$_2$C(Me)=CH$_2$ |
| I-1503 | | OCH$_2$CF$_3$ | OCH$_2$CH=C(Me)$_2$ |
| I-1504 | | OCH$_2$CF$_3$ | OCH$_2$CH=CH$_2$ |
| I-1505 | | OCH$_2$CF$_3$ | OCH$_2$CH=CHMe |
| I-1506 | | OCH$_2$CH=CH$_2$ | OCH$_2$C(Me)=CH$_2$ |
| I-1507 | | OCH$_2$CH=CH$_2$ | OCH$_2$CCH |
| I-1508 | | OCH$_2$CH=CH$_2$ | OCH$_2$CH$_2$C(Me)=CH$_2$ |
| I-1509 | | OCH$_2$CH=CH$_2$ | OCH$_2$CH=C(Me)$_2$ |
| I-1510 | | OCH$_2$CH=CH$_2$ | OCH$_2$CH=CHMe |
| I-1511 | | OEt | O-i-Bu |
| I-1512 | | OEt | OBu |
| I-1513 | | OEt | OCH$_2$C(Me)=CH$_2$ |
| I-1514 | | OEt | OCH$_2$CCH |
| I-1515 | | OEt | OCH$_2$CH$_2$C(Me)=CH$_2$ |
| I-1516 | | OEt | OCH$_2$CH=C(Me)$_2$ |
| I-1517 | | OEt | OCH$_2$CH=CH$_2$ |
| I-1518 | | OEt | OCH$_2$CH=CHMe |
| I-1519 | | OEt | OPr |
| I-1520 | | OMe | O-i-Bu |
| I-1521 | | OMe | OBu |
| I-1522 | | OMe | OCH$_2$C(Me)=CH$_2$ |
| I-1523 | | OMe | OCH$_2$CCH |
| I-1524 | | OMe | OCH$_2$CH$_2$C(me)=CH$_2$ |
| I-1525 | | OMe | OCH$_2$CH=C(Me)$_2$ |
| I-1526 | | OMe | OCH$_2$CH=CH$_2$ |
| I-1527 | | OMe | OCH$_2$CH=CHMe |
| I-1528 | | OMe | OEt |
| I-1529 | | OMe | OPr |
| I-1530 | | OPr | O-i-Bu |
| I-1531 | | OPr | OBu |
| I-1532 | | OPr | OCH$_2$C(Me)=CH$_2$ |
| I-1533 | | OPr | OCH$_2$CCH |
| I-1534 | | OPr | OCH$_2$CH$_2$C(Me)=CH$_2$ |
| I-1535 | | OPr | OCH$_2$CH=C(Me)$_2$ |
| I-1536 | | OPr | OCH$_2$CH=CH$_2$ |
| I-1537 | | OPr | OCH$_2$CH=CHMe |
| I-2041 | A fluorine atom | Me | SMe |
| I-2042 | at 4-position | Me | SEt |
| I-2043 | (4-F) for | Me | SPr |
| I-2044 | Compound I-2041 | OMe | SMe |
| I-2045 | through | OMe | SEt |
| I-2046 | Compound I-2055 | OMe | SPr |
| I-2047 | | SMe | SMe |
| I-2048 | | SEt | SEt |
| I-2049 | | SPr | SPr |
| I-2050 | | OCH$_2$CH=CH$_2$ | SMe |
| I-2051 | | OCH$_2$CH=CH$_2$ | SEt |
| I-2052 | | OCH$_2$CH=CH$_2$ | SPr |
| I-2053 | | Cl | SMe |
| I-2054 | | Cl | SEt |
| I-2055 | | Cl | SPr |

TABLE 1

(14/15)

| No. | X$_n$ | R$^1$ | R$^2$ |
|---|---|---|---|
| I-1538 | A bromine atom | OCHF2 | OCHF$_2$ |
| I-1539 | at 4-position | CF$_3$ | OCH$_2$C(Me)=CH$_2$ |
| I-1540 | (4-Br) for | CF$_3$ | OCH$_2$CCH |
| I-1541 | Compound I-1538 | CF$_3$ | OCH$_2$CH$_2$C(Me)=CH$_2$ |
| I-1542 | through | CF$_3$ | OCH$_2$CH=C(Me)$_2$ |

TABLE 1-continued (14/15)

| No. | $X_n$ | $R^1$ | $R^2$ |
|---|---|---|---|
| I-1543 | Compound I-1647 | $CF_3$ | $OCH_2CH=CH_2$ |
| I-1544 | | $CF_3$ | $OCH_2CH=CHMe$ |
| I-1545 | | Cl | O-i-Bu |
| I-1546 | | Cl | OBu |
| I-1547 | | Cl | $OCH_2C(Me)=CH_2$ |
| I-1548 | | Cl | $OCH_2C_2F_5$ |
| I-1549 | | Cl | $OCH_2CCH$ |
| I-1550 | | Cl | $OCH_2CF_3$ |
| I-1551 | | Cl | $OCH_2CH_2C(Me)=CH_2$ |
| I-1552 | | Cl | $OCH_2CH=C(Me)_2$ |
| I-1553 | | Cl | $OCH_2CH=CH_2$ |
| I-1554 | | Cl | $OCH_2CH=CHMe$ |
| I-1555 | | Cl | OEt |
| I-1556 | | Cl | OMe |
| I-1557 | | Cl | OPr |
| I-1558 | | Et | $OCH_2C(Me)=CH_2$ |
| I-1559 | | Et | $OCH_2CCH$ |
| I-1560 | | Et | $OCH_2CH_2C(Me)=CH_2$ |
| I-1561 | | Et | $OCH_2CH=C(Me)_2$ |
| I-1562 | | Et | $OCH_2CH=CH_2$ |
| I-1563 | | Et | $OCH_2CH=CHMe$ |
| I-1564 | | Me | O-i-Pr |
| I-1565 | | Me | $OCH_2C(Me)=CH_2$ |
| I-1566 | | Me | $OCH_2CCH$ |
| I-1567 | | Me | $OCH_2CH_2C(Me)=CH_2$ |
| I-1568 | | Me | $OCH_2CH=C(Me)_2$ |
| I-1569 | | Me | $OCH_2CH=CH_2$ |
| I-1570 | | Me | $OCH_2CH=CHMe$ |
| I-1571 | | Me | OEt |
| I-1572 | | Me | OMe |
| I-1573 | | O-i-Bu | O-i-Bu |
| I-1574 | | OBu | OBu |
| I-1575 | | $OCH_2C(Me)=CH_2$ | $OCH_2C(Me)=CH_2$ |
| I-1576 | | $OCH_2CCH$ | $OCH_2CCH$ |
| I-1577 | | $OCH_2CH_2C(Me)=CH_2$ | $OCH_2CH_2C(Me)=CH_2$ |
| I-1578 | | $OCH_2CH=C(Me)_2$ | $OCH_2CH=C(Me)_2$ |
| I-1579 | | $OCH_2CH=CH_2$ | $OCH_2CH=CH_2$ |
| I-1580 | | $OCH_2CH=CHMe$ | $OCH_2CH=CHMe$ |
| I-1581 | | OEt | OEt |
| I-1582 | | OMe | OMe |
| I-1583 | | OPr | OPr |
| I-1584 | | Pr | $OCH_2C(Me)=CH_2$ |
| I-1585 | | Pr | $OCH_2CCH$ |
| I-1586 | | Pr | $OCH_2CH_2C(Me)=CH_2$ |
| I-1587 | | Pr | $OCH_2CH=C(Me)_2$ |
| I-1588 | | Pr | $OCH_2CH=CH_2$ |
| I-1589 | | Pr | $OCH_2CH=CHMe$ |
| I-1590 | | i-Pr | $OCH_2C(Me)=CH_2$ |
| I-1591 | | i-Pr | $OCH_2CCH$ |
| I-1592 | | i-Pr | $OCH_2CH_2C(Me)=CH_2$ |
| I-1593 | | i-Pr | $OCH_2CH=C(Me)_2$ |
| I-1594 | | i-Pr | $OCH_2CH=CH_2$ |
| I-1595 | | i-Pr | $OCH_2CH=CHMe$ |
| I-1596 | | O-i-Bu | $OCH_2C(Me)=CH_2$ |
| I-1597 | | O-i-Bu | $OCH_2CCH$ |
| I-1598 | | O-i-Bu | $OCH_2CH_2C(Me)=CH_2$ |
| I-1599 | | O-i-Bu | $OCH_2CH=C(Me)_2$ |
| I-1600 | | O-i-Bu | $OCH_2CH=CH_2$ |
| I-1601 | | O-i-Bu | $OCH_2CH=CHMe$ |
| I-1602 | | OBu | O-i-Bu |
| I-1603 | | OBu | $OCH_2C(Me)=CH_2$ |
| I-1604 | | OBu | $OCH_2CCH$ |
| I-1605 | | OBu | $OCH_2CH_2C(Me)=CH_2$ |
| I-1606 | | OBu | $OCH_2CH=C(Me)_2$ |
| I-1607 | | OBU | $OCH_2CH=CH_2$ |
| I-1608 | | OBu | $OCH_2CH=CHMe$ |
| I-1609 | | $OCH_2CF_3$ | $OCH_2C(Me)=CH_2$ |
| I-1610 | | $OCH_2CF_3$ | $OCH_2C_2F_5$ |
| I-1611 | | $OCH_2CF_3$ | $OCH_2CCH$ |
| I-1612 | | $OCH_2CF_3$ | $OCH_2CH_2C(Me)=CH_2$ |
| I-1613 | | $OCH_2CF_3$ | $OCH_2CH=C(Me)_2$ |
| I-1614 | | $OCH_2CF_3$ | $OCH_2CH=CH_2$ |
| I-1615 | | $OCH_2CF_3$ | $OCH_2CH=CHMe$ |
| I-1616 | | $OCH_2CH=CH_2$ | $OCH_2C(Me)=CH_2$ |
| I-1617 | | $OCH_2CH=CH_2$ | $OCH_2CCH$ |

TABLE 1-continued (14/15)

| No. | X_n | R¹ | R² |
|---|---|---|---|
| I-1618 | | OCH$_2$CH=CH$_2$ | OCH$_2$CH$_2$C(Me)=CH$_2$ |
| I-1619 | | OCH$_2$CH=CH$_2$ | OCH$_2$CH=C(Me)$_2$ |
| I-1620 | | OCH$_2$CH=CH$_2$ | OCH$_2$CH=CHMe |
| I-1621 | | OEt | O-i-Bu |
| I-1622 | | OEt | OBu |
| I-1623 | | OEt | OCH$_2$C(Me)=CH$_2$ |
| I-1624 | | OEt | OCH$_2$CCH |
| I-1625 | | OEt | OCH$_2$CH$_2$C(Me)=CH$_2$ |
| I-1626 | | OEt | OCH$_2$CH=C(Me)$_2$ |
| I-1627 | | OEt | OCH$_2$CH=CH$_2$ |
| I-1628 | | OEt | OCH$_2$CH=CHMe |
| I-1629 | | OEt | OPr |
| I-1630 | | OMe | O-i-Bu |
| I-1631 | | OMe | OBu |
| I-1632 | | OMe | OCH$_2$C(Me)=CH$_2$ |
| I-1633 | | OMe | OCH$_2$CCH |
| I-1634 | | OMe | OCH$_2$CH$_2$C(Me)=CH$_2$ |
| I-1635 | | OMe | OCH$_2$CH=C(Me)$_2$ |
| I-1636 | | OMe | OCH$_2$CH=CH$_2$ |
| I-1637 | | OMe | OCH$_2$CH=CHMe |
| I-1638 | | OMe | OEt |
| I-1639 | | OMe | OPr |
| I-1640 | | OPr | O-i-Bu |
| I-1641 | | OPr | OBu |
| I-1642 | | OPr | OCH$_2$C(Me)=CH$_2$ |
| I-1643 | | OPr | OCH$_2$CCH |
| I-1644 | | OPr | OCH$_2$CH$_2$C(Me)=CH$_2$ |
| I-1645 | | OPr | OCH$_2$CH=C(Me)$_2$ |
| I-1646 | | OPr | OCH$_2$CH=CH$_2$ |
| I-1647 | | OPr | OCH$_2$CH=CHMe |

TABLE 1

(15/15)

| No. | X_n | R¹ | R² |
|---|---|---|---|
| I-1648 | A methyl group | OCHF$_2$ | OCHF$_2$ |
| I-1649 | at 4-position | CF$_3$ | OCH$_2$C(Me)=CH$_2$ |
| I-1650 | (4-Me) for | CF$_3$ | OCH$_2$CCH |
| I-1651 | Compound I-1648 | CF$_3$ | OCH$_2$CH$_2$C(Me)=CH$_2$ |
| I-1652 | through | CF$_3$ | OCH$_2$CH=C(Me)$_2$ |
| I-1653 | Compound I-1757 | CF$_3$ | OCH$_2$CH=CH$_2$ |
| I-1654 | | CF$_3$ | OCH$_2$CH=CHMe |
| I-1655 | | Cl | O-i-Bu |
| I-1656 | | Cl | OBu |
| I-1657 | | Cl | OCH$_2$C(Me)=CH$_2$ |
| I-1658 | | Cl | OCH$_2$C$_2$F$_5$ |
| I-1659 | | Cl | OCH$_2$CCH |
| I-1660 | | Cl | OCH$_2$CF$_3$ |
| I-1661 | | Cl | OCH$_2$CH$_2$C(Me)=CH$_2$ |
| I-1662 | | Cl | OCH$_2$CH=C(Me)$_2$ |
| I-1663 | | Cl | OCH$_2$CH=CH$_2$ |
| I-1664 | | Cl | OCH$_2$CH=CHMe |
| I-1665 | | Cl | OEt |
| I-1666 | | Cl | OMe |
| I-1667 | | Cl | OPr |
| I-1668 | | Et | OCH$_2$C(Me)=CH$_2$ |
| I-1669 | | Et | OCH$_2$CCH |
| I-1670 | | Et | OCH$_2$CH$_2$C(Me)=CH$_2$ |
| I-1671 | | Et | OCH$_2$CH=C(Me)$_2$ |
| I-1672 | | Et | OCH$_2$CH=CH$_2$ |
| I-1673 | | Et | OCH$_2$CH=CHMe |
| I-1674 | | Me | O-i-Pr |
| I-1675 | | Me | OCH$_2$C(Me)=CH$_2$ |
| I-1676 | | Me | H |
| I-1677 | | Me | OCH$_2$CH$_2$C(Me)=CH$_2$ |
| I-1678 | | Me | OCH$_2$CH=C(Me)$_2$ |
| I-1679 | | Me | OCH$_2$CH=CH$_2$ |
| I-1680 | | Me | OCH$_2$CH=CHMe |
| I-1681 | | Me | OEt |
| I-1682 | | Me | OMe |
| I-1683 | | O-i-Bu | O-i-Bu |

TABLE 1-continued (15/15)

| No. | X$_n$ | R$^1$ | R$^2$ |
|---|---|---|---|
| I-1684 | | OBu | OBu |
| I-1685 | | OCH$_2$C(Me)=CH$_2$ | OCH$_2$C(Me)=CH$_2$ |
| I-1686 | | OCH$_2$CCH | OCH$_2$CCH |
| I-1687 | | OCH$_2$CH$_2$C(Me)=CH$_2$ | OCH$_2$CH$_2$C(Me)=CH$_2$ |
| I-1688 | | OCH$_2$CH=C(Me)$_2$ | OCH$_2$CH=C(Me)$_2$ |
| I-1689 | | OCH$_2$CH=CH$_2$ | OCH$_2$CH=CH$_2$ |
| I-1690 | | OCH$_2$CH=CHMe | OCH$_2$CH=CHMe |
| I-1691 | | OEt | OEt |
| I-1692 | | OMe | OMe |
| I-1693 | | OPr | OPr |
| I-1694 | | Pr | OCH$_2$C(Me)=CH$_2$ |
| I-1695 | | Pr | OCH$_2$CCH |
| I-1696 | | Pr | OCH$_2$CH$_2$C(Me)=CH$_2$ |
| I-1697 | | Pr | OCH$_2$CH=C(Me)$_2$ |
| I-1698 | | Pr | OCH$_2$CH=CH$_2$ |
| I-1699 | | Pr | OCH$_2$CH=CHMe |
| I-1700 | | i-Pr | OCH$_2$C(Me)=CH$_2$ |
| I-1701 | | i-Pr | OCH$_2$CCH |
| I-1702 | | i-Pr | OCH$_2$CH$_2$C(Me)=CH$_2$ |
| I-1703 | | i-Pr | OCH$_2$CH=C(Me)$_2$ |
| I-1704 | | i-Pr | OCH$_2$CH=CH$_2$ |
| I-1705 | | i-Pr | OCH$_2$CH=CHMe |
| I-1706 | | O-i-Bu | OCH$_2$C(Me)=CH$_2$ |
| I-1707 | | O-i-Bu | OCH$_2$CCH |
| I-1708 | | O-i-Bu | OCH$_2$CH$_2$C(Me)=CH$_2$ |
| I-1709 | | O-i-Bu | OCH$_2$CH=C(Me)$_2$ |
| I-1710 | | O-i-Bu | OCH$_2$CH=CH$_2$ |
| I-1711 | | O-i-Bu | OCH$_2$CH=CHMe |
| I-1712 | | OBu | O-i-Bu |
| I-1713 | | OBu | OCH$_2$C(Me)=CH$_2$ |
| I-1714 | | OBu | OCH$_2$CCH |
| I-1715 | | OBu | OCH$_2$CH$_2$C(Me)=CH$_2$ |
| I-1716 | | OBu | OCH$_2$CH=C(Me)$_2$ |
| I-1717 | | OBu | OCH$_2$CH=CH$_2$ |
| I-1718 | | OBu | OCH$_2$CH=CHMe |
| I-1719 | | OCH$_2$CF$_3$ | OCH$_2$C(Me)=CH$_2$ |
| I-1720 | | OCH$_2$CF$_3$ | OCH$_2$C$_2$F$_5$ |
| I-1721 | | OCH$_2$CF$_3$ | OCH$_2$CCH |
| I-1722 | | OCH$_2$CF$_3$ | OCH$_2$CH$_2$C(Me)=CH$_2$ |
| I-1723 | | OCH$_2$CF$_3$ | OCH$_2$CH=C(Me)$_2$ |
| I-1724 | | OCH$_2$CF$_3$ | OCH$_2$CH=CH$_2$ |
| I-1725 | | OCH$_2$CF$_3$ | OCH$_2$CH=CHMe |
| I-1726 | | OCH$_2$CH=CH$_2$ | OCH$_2$C(Me)=CH$_2$ |
| I-1727 | | OCH$_2$CH=CH$_2$ | OCH$_2$CCH |
| I-1728 | | OCH$_2$CH=CH$_2$ | OCH$_2$CH$_2$C(Me)=CH$_2$ |
| I-1729 | | OCH$_2$CH=CH$_2$ | OCH$_2$CH=C(Me)$_2$ |
| I-1730 | | OCH$_2$CH=CH$_2$ | OCH$_2$CH=CHMe |
| I-1731 | | OEt | O-i-Bu |
| I-1732 | | OEt | OBu |
| I-1733 | | OEt | OCH$_2$C(Me)=CH$_2$ |
| I-1734 | | OEt | OCH$_2$CCH |
| I-1735 | | OEt | OCH$_2$CH$_2$C(Me)=CH$_2$ |
| I-1736 | | OEt | OCH$_2$CH=C(Me)$_2$ |
| I-1737 | | OEt | OCH$_2$CH=CH$_2$ |
| I-1738 | | OEt | OCH$_2$CH=CHMe |
| I-1739 | | OEt | OPr |
| I-1740 | | OMe | O-i-Bu |
| I-1741 | | OMe | OBu |
| I-1742 | | OMe | OCH$_2$C(Me)=CH$_2$ |
| I-1743 | | OMe | OCH$_2$CCH |
| I-1744 | | OMe | OCH$_2$CH$_2$C(Me)=CH$_2$ |
| I-1745 | | OMe | OCH$_2$CH=C(Me)$_2$ |
| I-1746 | | OMe | OCH$_2$CH=CH$_2$ |
| I-1747 | | OMe | OCH$_2$CH=CHMe |
| I-1748 | | OMe | OEt |
| I-1749 | | OMe | OPr |
| I-1750 | | OPr | O-i-Bu |
| I-1751 | | OPr | OBu |
| I-1752 | | OPr | OCH$_2$C(Me)=CH$_2$ |
| I-1753 | | OPr | OCH$_2$CCH |
| I-1754 | | OPr | OCH$_2$CH$_2$C(Me)=CH$_2$ |
| I-1755 | | OPr | OCH$_2$CH=C(Me)$_2$ |
| I-1756 | | OPr | OCH$_2$CH=CH$_2$ |
| I-1757 | | OPr | OCH$_2$CH=CHMe |
| I-2061 | A methyl group | Me | SMe |

TABLE 1-continued (15/15)

| No. | $X_n$ | $R^1$ | $R^2$ |
|---|---|---|---|
| I-2062 | at 4-position | Me | SEt |
| I-2063 | (4-Me) for | Me | SPr |
| I-2064 | Compound I-2061 | OMe | SMe |
| I-2065 | through | OMe | SEt |
| I-2066 | Compound I-2075 | OMe | SPr |
| I-2067 | | SMe | SMe |
| I-2068 | | SEt | SEt |
| I-2069 | | SPr | SPr |
| I-2070 | | OCH$_2$CH=CH$_2$ | SMe |
| I-2071 | | OCH$_2$CH=CH$_2$ | SEt |
| I-2072 | | OCH$_2$CH=CH$_2$ | SPr |
| I-2073 | | Cl | SMe |
| I-2074 | | Cl | SEt |
| I-2075 | | Cl | SPr |

2-Benzyloxypyrimidine derivatives of the formula (I) shown in Table 1 (1/15 to 15/15) can be synthesized in accordance with the following scheme:

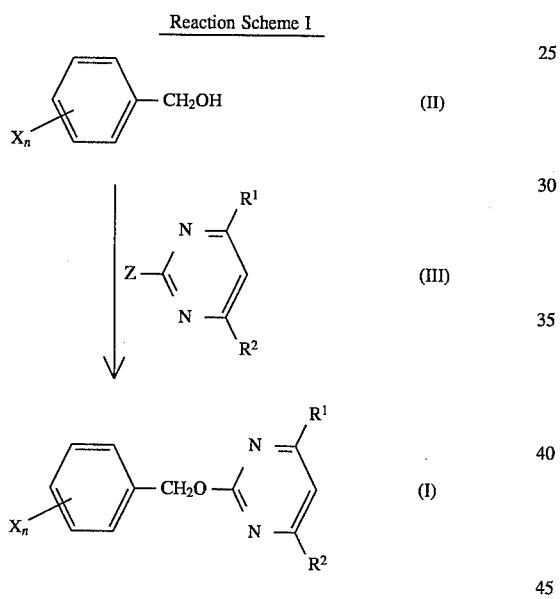

Reaction Scheme I

As shown in the above Reaction scheme I, the compound of the formula (I) may be produced by reacting the compound of the formula (II) with a substantially equal molar amount of the compound of the formula (III) in the presence of a basic compound, preferably in a solvent such as amides (e.g., dimethylformamide, dimethylacetamide, and N-methyl-2-pyrrolidinone), ethers (e.g., diethyl ether, dimethoxyethane, diisopropyl ether, tetrahydrofuran, diglyme, and dioxane), and aromatic hydrocarbons (e.g., benzene, toluene, xylene, and methylnaphthalene), preferably at a temperature in the range of −20° C. to 150° C. for a period of about 0.5 hour to one night (about 12 hours).

An iodide such as sodium iodide and potassium iodide or a crown ether such as 18-crown-6 and dibenzo-18-crown-6 may be added to the reaction as a reaction accelerator.

Examples of the compounds (II) which can be used for the production of the compounds (I) are shown in Table 2.

TABLE 2

| No. | Compound |
|---|---|
| II-1 | 2,3-Difluorobenzylalcohol |
| II-2 | 2,3-Dimethyl-4-methoxybenzylalcohol |
| II-3 | 2,3-Dimethoxybenzylalcohol |
| II-4 | 2,4-Dichlorobenzylalcohol |
| II-5 | 2,4-Difluorobenzylalcohol |
| II-6 | 2,4-Dimethylbenzylalcohol |
| II-7 | 2,4-Dimethoxy-3-methylbenzylalcohol |
| II-8 | 2,4-Dimethoxybenzylalcohol |
| II-9 | 2,5-Dichlorobenzylalcohol |
| II-10 | 2,5-Difluorobenzylalcohol |
| II-11 | 2,5-Dimethylbenzylalcohol |
| II-12 | 2,5-Dimethoxybenzylalcohol |
| II-13 | 2,6-Dichlorobenzylalcohol |
| II-14 | 2,6-Difluorobenzylalcohol |
| II-15 | 2-(Ethoxycarbonyl)benzylalcohol |
| II-16 | 2-(Trifluoromethyl)benzylalcohol |
| II-17 | 2-(Hydroxycarbonyl)benzylalcohol |
| II-18 | 2-(Hydroxymethyl)benzylalcohol |
| II-19 | 2-(Methoxycarbonyl)benzylalcohol |
| II-20 | 2-Ethylbenzylalcohol |
| II-21 | 2-Ethoxybenzylalcohol |
| II-22 | 2-Chloro-6-fluorobenzylalcohol |
| II-23 | 2-Chlorobenzylalcohol |
| II-24 | 2-Fluorobenzylalcohol |
| II-25 | 2-Bromobenzylalcohol |
| II-26 | 2-Methylbenzylalcohol |
| II-27 | 2-Methoxybenzylalcohol |
| II-28 | 2-Iodobenzylalcohol |
| II-29 | 3,4,5-Trimethoxybenzylalcohol |
| II-30 | 3,4-Dichlorobenzylalcohol |
| II-31 | 3,4-Difluorobenzylalcohol |
| II-32 | 3,4-Dimethylbenzylalcohol |
| II-33 | 3,5-Dichlorobenzylalcohol |
| II-34 | 3,5-Difluorobenzylalcohol |
| II-35 | 3,5-Dimethylbenzylalcohol |
| II-36 | 3,5-Dimethoxybenzylalcohol |
| II-37 | 3,5-Bis(triluoromethyl)benzylalcohol |
| II-38 | 3-(Trifluoromethyl)benzylalcohol |
| II-39 | 3-Ethoxy-4-methylbenzylalcohol |
| II-40 | 3-Ethoxy-4-methoxybenzylalcohol |
| II-41 | 3-Chlorobenzylalcohol |
| II-42 | 3-Nitrobenzylalcohol |
| II-43 | 3-Fluorobenzylalcohol |
| II-44 | 3-Bromobenzylalcohol |
| II-45 | 3-Benzyloxybenzylalcohol |
| II-46 | 3-Methylbenzylalcohol |
| II-47 | 3-Methoxybenzylalcohol |
| II-48 | 3-Iodobenzylalcohol |
| II-49 | 4-(1-Methylethyl)benzylalcohol |

TABLE 2-continued

| No. | Compound |
| --- | --- |
| II-50 | 4-(Trifluoromethyl)benzylalcohol |
| II-51 | 4-(Methylthio)benzylalcohol |
| II-52 | 4-(Methoxycarbonyl)benzylalcohol |
| II-53 | 4-Ethoxy-3-methoxybenzylalcohol |
| II-54 | 4-Chlorobenzylalcohol |
| II-55 | 4-Phenylbenzylalcohol |
| II-56 | 4-Fluorobenzylalcohol |
| II-57 | 4-Bromo-2-methoxybenzylalcohol |
| II-58 | 4-Bromobenzylalcohol |
| II-59 | 4-Benzyloxy-3-methoxybenzylalcohol |
| II-60 | 4-Benzyloxybenzylalcohol |
| II-61 | 4-Methylbenzylalcohol |
| II-62 | 4-Methoxybenzylalcohol |
| II-63 | 4-Iodobenzylalcohol |
| II-64 | Benzylalcohol |

The compounds of the formula (III) which may be used as starting materials in the Reaction scheme I can be either commercially available or easily synthesized.

As those in which Z represents a halogen among substituted pyrimidine derivatives of the formula (III) to be used as starting materials in the Reaction scheme I, commercially available reagents such as 2-chloropyrimidine, 2,4-dichloro-6-methylpyrimidine, and 2,4,6-trichloropyrimidine may be used. Alternatively, they may be synthesized by the process described in J. Chem. Soc. (C), 2031, (1966).

Among substituted pyrimidine derivatives of the formula (III), those of the formula (III-e) in which Z is linked to the pyrimidine ring through the sulfonyl thereof can be synthesized by oxidizing sulfur of 2-(alkylthio, aralkylthio, or arylthio)pyrimidine derivatives of the formula (IV-e), as shown in Reaction scheme II:

Reaction Scheme II

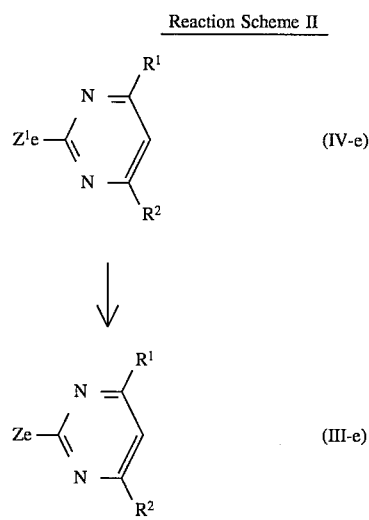

(IV-e)

↓

(III-e)

wherein $R^1$ and $R^2$ each independently represents hydrogen, a halogen, hydroxyl, $C_1$–$C_4$ alkyl, $C_1$–$C_4$ haloalkyl, C3–$C_5$ alkenyl, $C_3$–$C_5$ alkynyl, $C_1$–$C_4$ alkoxy, $C_1$–$C_4$ haloalkoxy, $C_3$–$C_5$ alkenyloxy, $C_3$–$C_5$ alkynyloxy, $C_1$–$C_4$ alkylthio, or phenyl;

$Z^1e$ represents $C_1$–$C_4$ alkylthio, $C_7$–$C_9$ aralkylthio, or arylthio (usually $C_6$–$C_8$); and Ze represents $C_1$–$C_4$ alkylsulfonyl, $C_7$–$C_9$ aralkylsulfonyl or arylsulfonyl (usually $C_6$–$C_8$).

Ze preferably includes the following groups:

$C_1$–$C_4$ alkylsulfonyl such as methylsulfonyl and ethylsulfonyl;

$C_7$–$C_9$ aralkylsulfonyl such as benzylsulfonyl; and arylsulfonyl (usually $C_6$–$C_8$) such as phenylsulfonyl and p-tolylsulfonyl.

$Z^1e$ preferably includes the following groups:

$C_1$–$C_4$ alkylthio such as methylthio and ethylthio;

$C_7$–$C_9$ aralkylthio such as benzylthio; and arylthio (usually $C_6$–$C_8$) such as phenylthio and p-tolylthio.

Examples of oxidants which may be used in the above oxidation reaction are peracids, sodium hypochloride, chlorine, potassium permanganate, and sodium tungstate.

Peracids are preferably selected from peracetic acid, perbenzoic acid, m-chloroperbenzoic acid, and perphthalic acid.

Peracetic acid may optionally be in situ produced in a reaction vessel by adding hydrogen peroxide to an acetic acid solution of the compound (IV-e).

Solvents which may be used in the oxidation reaction are halogenated alkyls (e.g., dichloromethane and chloroform), esters, aromatic hydrocarbons, lower fatty acids and water. Depending on the oxidants (e.g., chlorine), water should be used as solvent.

This oxidation reaction may be conducted at a temperature from under ice to the reflux point of the solvent (when a solvent is used).

Compounds (III-e) may be produced by oxidizing sulfur of commercially available reagents such as 4,6-dichloro-2-(methylthio)pyrimidine. They may also be produced by oxidizing sulfur contained in methylthio of 2-(methylthio)pyrimidine derivatives which can be prepared according to the process described in J. Chem. Soc., 1957, 1830 or in Grand Organic Chemistry, vol.17, p.94 (1959, published by Asakura Shoten).

Among substituted pyrimidine derivatives of the formula (III-e), examples of those in which Ze represents methylsulfonyl are shown in Table 3. These compounds may be used as starting materials for the production of the compounds (I) shown in Table 1 (1/15 to 15/15). In Table 3, $R^1$ and $R^2$ are identified by the same abbreviations as used in Table 1 (1/15 to 15/15).

TABLE 3

| No. | $R^1$ | $R^2$ |
| --- | --- | --- |
| III-1 | Me | H |
| III-2 | Me | Me |
| III-3 | Br | Br |
| III-4 | Cl | $CF_3$ |
| III-5 | Cl | Cl |
| III-6 | Cl | Et |
| III-7 | Cl | Me |
| III-8 | Cl | Ph |
| III-9 | Cl | Pr |
| III-10 | Cl | i-Pr |
| III-11 | $OCHF_2$ | $OCHF_2$ |
| III-12 | $CF_3$ | $OCH_2C(Me)=CH_2$ |
| III-13 | $CF_3$ | $OCH_2CCH$ |
| III-14 | $CF_3$ | $OCH_2CH_2C(Me)=CH_2$ |
| III-15 | $CF_3$ | $OCH_2CH=C(Me)_2$ |
| III-16 | $CF_3$ | $OCH_2CH=CH_2$ |
| III-17 | $CF_3$ | $OCH_2CH=CHMe$ |
| III-18 | Cl | O-i-Bu |
| III-19 | Cl | OBu |
| III-20 | Cl | $OCH_2C(Me)=CH_2$ |
| III-21 | Cl | $OCH_2C_2F_5$ |
| III-22 | Cl | $OCH_2CCH$ |
| III-23 | Cl | $OCH_2CF_3$ |
| III-24 | Cl | $OCH_2CH_2C(Me)=CH_2$ |
| III-25 | Cl | $OCH_2CH=C(Me)_2$ |
| III-26 | Cl | $OCH_2CH=CH_2$ |

TABLE 3-continued

| No. | R¹ | R² |
|---|---|---|
| III-27 | Cl | OCH$_2$CH=CHMe |
| III-28 | Cl | OEt |
| III-29 | Cl | OMe |
| III-30 | Cl | OPr |
| III-31 | Et | OCH$_2$C(Me)=CH$_2$ |
| III-32 | Et | OCH$_2$CCH |
| III-33 | Et | OCH$_2$CH$_2$C(Me)=CH$_2$ |
| III-34 | Et | OCH$_2$CH=C(Me)$_2$ |
| III-35 | Et | OCH$_2$CH=CH$_2$ |
| III-36 | Et | OCH$_2$CH=CHMe |
| III-37 | Me | O-i-Pr |
| III-38 | Me | OCH$_2$C(Me)=CH$_2$ |
| III-39 | Me | OCH$_2$CCH |
| III-40 | Me | OCH$_2$CH$_2$C(Me)=CH$_2$ |
| III-41 | Me | OCH$_2$CH=C(Me)$_2$ |
| III-42 | Me | OCH$_2$CH=CH$_2$ |
| III-43 | Me | OCH$_2$CH=CHMe |
| III-44 | Me | OEt |
| III-45 | Me | OMe |
| III-46 | O-i-Bu | O-i-Bu |
| III-47 | OBu | OBu |
| III-48 | OCH$_2$C(Me)=CH$_2$ | OCH$_2$C(Me)=CH$_2$ |
| III-49 | OCH$_2$CCH | OCH$_2$CCH |
| III-50 | OCH$_2$CH$_2$C(Me)=CH$_2$ | OCH$_2$CH$_2$C(Me)=CH$_2$ |
| III-51 | OCH$_2$CH=C(Me)$_2$ | OCH$_2$CH=C(Me)$_2$ |
| III-52 | OCH$_2$CH=CH$_2$ | OCH$_2$CH=CH$_2$ |
| III-53 | OCH$_2$CH=CHMe | OCH$_2$CH=CHMe |
| III-54 | OEt | OEt |
| III-55 | OMe | OMe |
| III-56 | OPr | OPr |
| III-57 | Pr | OCH$_2$C(Me)=CH$_2$ |
| III-58 | Pr | OCH$_2$CCH |
| III-59 | Pr | OCH$_2$CH$_2$C(Me)=CH$_2$ |
| III-60 | Pr | OCH$_2$CH=C(Me)$_2$ |
| III-61 | Pr | OCH$_2$CH=CH$_2$ |
| III-62 | Pr | OCH$_2$CH=CHMe |
| III-63 | i-Pr | OCH$_2$C(Me)=CH$_2$ |
| III-64 | i-Pr | OCH$_2$CCH |
| III-65 | i-Pr | OCH$_2$CH$_2$C(Me)=CH$_2$ |
| III-66 | i-Pr | OCH$_2$CH=C(Me)$_2$ |
| III-67 | i-Pr | OCH$_2$CH=CH$_2$ |
| III-68 | i-Pr | OCH$_2$CH=CHMe |
| III-69 | O-i-Bu | OCH$_2$C(Me)=CH$_2$ |
| III-70 | O-i-Bu | OCH$_2$CCH |
| III-71 | O-i-Bu | C(Me)=CH$_2$ |
| III-72 | O-i-Bu | OCH$_2$CH=C(Me)$_2$ |
| III-73 | O-i-Bu | OCH$_2$CH=CH$_2$ |
| III-74 | O-i-Bu | OCH$_2$CH=CHMe |
| III-75 | OBu | O-i-Bu |
| III-76 | OBu | OCH$_2$C(Me)=CH$_2$ |
| III-77 | OBu | OCH$_2$CCH |
| III-78 | OBu | OCH$_2$CH$_2$C(Me)=CH$_2$ |
| III-79 | OBu | OCH$_2$CH=C(Me)$_2$ |
| III-80 | OBu | OCH$_2$CH=CH$_2$ |
| III-81 | OBu | OCH$_2$CH=CHMe |
| III-82 | OCH$_2$CF$_3$ | OCH$_2$C(Me)=CH$_2$ |
| III-83 | OCH$_2$CF$_3$ | OCH$_2$C$_2$F$_5$ |
| III-84 | OCH$_2$CF$_3$ | OCH$_2$CCH |
| III-85 | OCH$_2$CF$_3$ | OCH$_2$CH$_2$C(Me)=CH$_2$ |
| III-86 | OCH$_2$CF$_3$ | OCH$_2$CH=C(Me)$_2$ |
| III-87 | OCH$_2$CF$_3$ | OCH$_2$CH=CH$_2$ |
| III-88 | OCH$_2$CF$_3$ | OCH$_2$CH=CHMe |
| III-89 | OCH$_2$CH=CH$_2$ | OCH$_2$C(Me)=CH$_2$ |
| III-90 | OCH$_2$CH=CH$_2$ | OCH$_2$CCH |
| III-91 | OCH$_2$CH=CH$_2$ | OCH$_2$CH$_2$C(Me)=CH$_2$ |
| III-92 | OCH$_2$CH=CH$_2$ | OCH$_2$CH=C(Me)$_2$ |
| III-93 | OCH$_2$CH=CH$_2$ | OCH$_2$CH=CHMe |
| III-94 | OEt | O-i-Bu |
| III-95 | OEt | OBu |
| III-96 | OEt | OCH$_2$C(Me)=CH$_2$ |
| III-97 | OEt | OCH$_2$CCH |
| III-98 | OEt | OCH$_2$CH$_2$C(Me)=CH$_2$ |
| III-99 | OEt | OCH$_2$CH=C(Me)$_2$ |
| III-100 | OEt | OCH$_2$CH=CH$_2$ |
| III-101 | OEt | OCH$_2$CH=CHMe |
| III-102 | OEt | OPr |
| III-103 | OMe | O-i-Bu |
| III-104 | OMe | OBu |
| III-105 | OMe | OCH$_2$C(Me)=CH$_2$ |
| III-106 | OMe | OCH$_2$CCH |
| III-107 | OMe | OCH$_2$CH$_2$C(Me)=CH$_2$ |
| III-108 | OMe | OCH$_2$CH=C(Me)$_2$ |
| III-109 | OMe | OCH$_2$CH=CH$_2$ |
| III-110 | OMe | OCH$_2$CH=CHMe |
| III-111 | OMe | OEt |
| III-112 | OMe | OPr |
| III-113 | OPr | O-i-Bu |
| III-114 | OPr | OBu |
| III-115 | OPr | OCH$_2$C(Me)=CH$_2$ |
| III-116 | OPr | OCH$_2$CCH |
| III-117 | OPr | OCH$_2$CH$_2$C(Me)=CH$_2$ |
| III-118 | OPr | OCH$_2$CH=C(Me)$_2$ |
| III-119 | OPr | OCH$_2$CH=CH$_2$ |
| III-120 | OPr | OCH$_2$CH=CHMe |

Compounds of the formula (III) including Compounds III-1 to III-120 of Table 3 each may be produced as follows.

In chloroform, to each 1 mol of Compounds IV-1 to IV-120 of Table 4 below, about twice molar amount of m-chloroperbenzoic acid is added and then stirred for a period of from 1 hour to one night at room temperature. The reaction mixture is partitioned by using saturated aqueous sodium hydrogen carbonate. An organic phase is washed with saturated aqueous sodium chloride and then dried over anhydrous sodium sulfate. Thereafter, the solvent is distilled off to afford a crude product, which is then purified on column chromatography to obtain the compound of the formula (III) (Compounds III-1 to III-120).

Alternatively, Compound III-1 to III-120 may be produced through oxidation by adding hydrogen peroxide to an acetic acid solution of Compounds IV-1 to IV-120 while producing in situ peracetic acid in a reaction vessel. In this case, the reaction may be performed at a temperature in the range of from room temperature to 100° C. for a period of from 2 hours to one night.

Other compounds of the formula (III) can be obtained in a similar manner.

Among the above 2-(alkylthio, aralkylthio, or arylthio)pyrimidine derivatives, 2-(alkylthio or aralkylthio)pyrimidine derivatives can be synthesized by using the following processes.

Process (a): A compound having a 1,3-dicarbonyl group is cyclo-condensed with S-alkyl(or aralkyl)isothiourea.

This process (a) is suitable for the synthesis of the compounds in which a hydroxyl group is bonded to the positions 4 and/or 6 of 2-(alkylthio or aralkylthio)pyrimidine derivatives.

Process (b): A compound having a 1,3-dicarbonyl group is cyclo-condensed with thiourea to afford a 2-mercaptopyrimidine derivative, which is then alkylated or aralkylated at the 2-mercapto group thereof.

This process (b) is suitable for the synthesis of the compounds in which substituents are bonded to the positions 4 and 6 of the pyrimidine ring by a carbon-carbon bond, the compounds in which a hydrogen atom is bonded to either one of the positions 4 and 6 of the pyrimidine ring and a substituent is bonded to the other position by a carbon-carbon bond as well as the compounds in which a hydrogen atom is bonded to each of the positions 4 and 6 of the pyrimidine ring.

Compounds in which a halogen atom is bonded to the positions 4 and/or 6 of the pyrimidine ring can be derived from the compounds obtained by the process (a) or (b) as follows:

Process (c1), process (c2): A hydroxyl group is converted to a halogen atom by using phosphorus oxychloride (identical with phosphoryl chloride), phosphorus pentachloride, phosphorus oxybromide (identical with phosphoryl bromide or phosphoryl tribromide).

For convenience of explanation, dihalogenation and monohalogenation are designated as (c1) and (c2), respectively.

Further, a chlorine atom at the position 4 or 6 may be converted to an iodine atom through nucleophilic displacement by using potassium iodide or concentrated aqueous hydroiodic acid. Compounds in which a halogen atom and a hydroxyl group is bonded thereto can be synthesized as follows:

Process (d): Either one of the halogen atoms at the positions 4 and 6 obtained by (c1) or (c2) is converted to a hydroxyl group.

Compounds in which a substituent is ether-linked to the position 4 and/or 6 of the pyrimidine ring can be synthesized as follows:

Process (e): An oxygen atom of the hydroxyl group at the position 4 or 6 of the pyrimidine ring of the compound which was obtained from (a) or (b) is etherified in the presence of a basic compound.

Process (f): A halogen atom at the position 4 or 6 of the pyrimidine ring of the compound which was obtained from (c1) or (c2) is etherified through nucleophilic displacement in the presence of a basic compound.

Among the compounds in which a substituent is ether-linked to each of the positions 4 and 6 of the pyrimidine ring, those in which the substituent of the position 4 is different from that of the position 6 can be synthesized as follows:

Process (g): A halogen atom at the position 4 (or the position 6) of the compound obtained by (c1) is etherified through nucleophilic displacement, and then, a halogen atom at the position 6 (or 4) is etherified through nucleophilic displacement.

Process (h): A hydroxyl group of the compound obtained by (d) is etherified, and then, a halogen atom at the position 4 (or 6) is etherified.

Compounds having both an ether-linked substituent and a halogen atom, besides the above described process (f), can be synthesized as follows:

Process (i): A halogen atom at the position 4 (or 6) of the compounds obtained by (c1) is converted to a hydroxyl group, which is then etherified.

Compounds having both an ether-linked substituent and a hydroxyl group can be synthesized as follows:

Process (j): An oxygen atom of the hydroxyl group at either position 4 or position 6 of the pyrimidine ring of the compounds obtained by the process (a) or (b) is etherified in the presence of a basic compound.

Process (k): A halogen atom at the position 4 (or 6) of the compounds obtained by the process (c1) is converted to a hydroxyl group, an oxygen atom of which is then etherified. Then, a halogen atom at the position 6 (or 4) is converted to a hydroxyl group.

Examples compounds (IV-e) usable as starting materials for the production of compounds shown in Table 3 are listed in Table 4.

$R^1$ and $R^2$ in Table 4 are represented in a similar manner as in Table 1 (1/15 to 15/15). In the column of "$Z^1e$", SMe represents methylthio.

In the column of "process" in Table 4, symbols a, b, c1, c2, e, f and g corresponds to the processes (a), (b), (c1), (c2), (e), (f) and (g) above, respectively.

TABLE 4

| No. | $R^1$ | $R^2$ | $Z^1e$ | Process |
|---|---|---|---|---|
| IV-1 | Me | H | SMe | b |
| IV-2 | Me | Me | SMe | b |
| IV-3 | Br | Br | SMe | c1 |
| IV-4 | Cl | $CF_3$ | SMe | c2 |
| IV-5 | Cl | Cl | SMe | c1 |
| IV-6 | Cl | Et | SMe | c2 |
| IV-7 | Cl | Me | SMe | c2 |
| IV-8 | Cl | Ph | SMe | c2 |
| IV-9 | Cl | Pr | SMe | c2 |
| IV-10 | Cl | i-Pr | SMe | c2 |
| IV-11 | $OCHF_2$ | $OCHF_2$ | SMe | e |
| IV-12 | $CF_3$ | $OCH_2C(Me)=CH_2$ | SMe | f |
| IV-13 | $CF_3$ | $OCH_2CCH$ | SMe | f |
| IV-14 | $CF_3$ | $OCH_2CH_2C(Me)=CH_2$ | SMe | f |
| IV-15 | $CF_3$ | $OCH_2CH=C(Me)_2$ | SMe | f |
| IV-16 | $CF_3$ | $OCH_2CH=CH_2$ | SMe | f |
| IV-17 | $CF_3$ | $OCH_2CH=CHMe$ | SMe | f |
| IV-18 | Cl | O-i-Bu | SMe | f |
| IV-19 | Cl | OBu | SMe | f |
| IV-20 | Cl | $OCH_2C(Me)=CH_2$ | SMe | f |
| IV-21 | Cl | $OCH_2C_2F_5$ | SMe | f |
| IV-22 | Cl | $OCH_2CCH$ | SMe | f |
| IV-23 | Cl | $OCH_2CF_3$ | SMe | f |
| IV-24 | Cl | $OCH_2CH_2C(Me)=CH_2$ | SMe | f |
| IV-25 | Cl | $OCH_2CH=C(Me)_2$ | SMe | f |
| IV-26 | Cl | $OCH_2CH=CH_2$ | SMe | f |
| IV-27 | Cl | $OCH_2CH=CHMe$ | SMe | f |
| IV-28 | Cl | OEt | SMe | f |
| IV-29 | Cl | OMe | SMe | f |
| IV-30 | Cl | OPr | SMe | f |
| IV-31 | Et | $OCH_2C(Me)=CH_2$ | SMe | f |
| IV-32 | Et | $OCH_2CCH$ | SMe | f |
| IV-33 | Et | $OCH_2CH_2C(Me)=CH_2$ | SMe | f |

TABLE 4-continued

| No. | R¹ | R² | Z¹e | Process |
|---|---|---|---|---|
| IV-34 | Et | OCH₂CH=C(Me)₂ | SMe | f |
| IV-35 | Et | OCH₂CH=CH₂ | SMe | f |
| IV-36 | Et | OCH₂CH=CHMe | SMe | f |
| IV-37 | Me | O-i-Pr | SMe | f |
| IV-38 | Me | OCH₂C(Me)=CH₂ | SMe | f |
| IV-39 | Me | OCH₂CCH | SMe | f |
| IV-40 | Me | OCH₂CH₂C(Me)=CH₂ | SMe | f |
| IV-41 | Me | OCH₂CH=C(Me)₂ | SMe | f |
| IV-42 | Me | OCH₂CH=CH₂ | SMe | f |
| IV-43 | Me | OCH₂CH=CHMe | SMe | f |
| IV-44 | Me | OEt | SMe | f |
| IV-45 | Me | OMe | SMe | f |
| IV-46 | O-i-Bu | O-i-Bu | SMe | f |
| IV-47 | OBu | OBu | SMe | f |
| IV-48 | OCH₂C(Me)=CH₂ | OCH₂C(Me)=CH₂ | SMe | f |
| IV-49 | OCH₂CCH | OCH₂CCH | SMe | f |
| IV-50 | OCH₂CH₂C(Me)=CH₂ | OCH₂CH₂C(Me)=CH₂ | SMe | f |
| IV-51 | OCH₂CH=C(Me)₂ | OCH₂CH=C(Me)₂ | SMe | f |
| IV-52 | OCH₂CH=CH₂ | OCH₂CH=CH₂ | SMe | f |
| IV-53 | OCH₂CH=CHMe | OCH₂CH=CHMe | SMe | f |
| IV-54 | OEt | OEt | SMe | f |
| IV-55 | OMe | OMe | SMe | f |
| IV-56 | OPr | OPr | SMe | f |
| IV-57 | Pr | OCH₂C(Me)=CH₂ | SMe | f |
| IV-58 | Pr | OCH₂CCH | SMe | f |
| IV-59 | Pr | OCH₂CH₂C(Me)=CH₂ | SMe | f |
| IV-60 | Pr | OCH₂CH=C(Me)₂ | SMe | f |
| IV-61 | Pr | OCH₂CH=CH₂ | SMe | f |
| IV-62 | Pr | OCH₂CH=CHMe | SMe | f |
| IV-63 | i-Pr | OCH₂C(Me)=CH₂ | SMe | f |
| IV-64 | i-Pr | OCH₂CCH | SMe | f |
| IV-65 | i-Pr | OCH₂CH₂C(Me)=CH₂ | SMe | f |
| IV-66 | i-Pr | OCH₂CH=C(Me)₂ | SMe | f |
| IV-67 | i-Pr | OCH₂CH=CH₂ | SMe | f |
| IV-68 | i-Pr | OCH₂CH=CHMe | SMe | f |
| IV-69 | O-i-Bu | OCH₂C(Me)=CH₂ | SMe | g |
| IV-70 | O-i-Bu | OCH₂CCH | SMe | g |
| IV-71 | O-i-Bu | OCH₂CH₂C(Me)=CH₂ | SMe | g |
| IV-72 | O-i-Bu | OCH₂CH=C(Me)₂ | SMe | g |
| IV-73 | O-i-Bu | OCH₂CH=CH₂ | SMe | g |
| IV-74 | O-i-Bu | OCH₂CH=CHMe | SMe | g |
| IV-75 | OBu | O-i-Bu | SMe | g |
| IV-76 | OBu | OCH₂C(Me)=CH₂ | SMe | g |
| IV-77 | OBu | OCH₂CCH | SMe | g |
| IV-78 | OBu | OCH₂CH₂C(Me)=CH₂ | SMe | g |
| IV-79 | OBu | OCH₂CH=C(Me)₂ | SMe | g |
| IV-80 | OBu | OCH₂CH=CH₂ | SMe | g |
| IV-81 | OBu | OCH₂CH=CHMe | SMe | g |
| IV-82 | OCH₂CF₃ | OCH₂C(Me)=CH₂ | SMe | g |
| IV-83 | OCH₂CF₃ | OCH₂C₂F₅ | SMe | g |
| IV-84 | OCH₂CF₃ | OCH₂CCH | SMe | g |
| IV-85 | OCH₂CF₃ | OCH₂CH₂C(Me)=CH₂ | SMe | g |
| IV-86 | OCH₂CF₃ | OCH₂CH=C(Me)₂ | SMe | g |
| IV-87 | OCH₂CF₃ | OCH₂CH=CH₂ | SMe | g |
| IV-88 | OCH₂CF₃ | OCH₂CH=CHMe | SMe | g |
| IV-89 | OCH₂CH=CH₂ | OCH₂C(Me)=CH₂ | SMe | g |
| IV-90 | OCH₂CH=CH₂ | OCH₂CCH | SMe | g |
| IV-91 | OCH₂CH=CH₂ | OCH₂CH₂C(Me)=CH₂ | SMe | g |
| IV-92 | OCH₂CH=CH₂ | OCH₂CH=C(Me)₂ | SMe | g |
| IV-93 | OCH₂CH=CH₂ | OCH₂CH=CHMe | SMe | g |
| IV-94 | OEt | O-i-Bu | SMe | g |
| IV-95 | OEt | OBu | SMe | g |
| IV-96 | OEt | OCH₂C(Me)=CH₂ | SMe | g |
| IV-97 | OEt | OCH₂CCH | SMe | g |
| IV-98 | OEt | OCH₂CH₂C(Me)=CH₂ | SMe | g |
| IV-99 | OEt | OCH₂CH=C(Me)₂ | SMe | g |
| IV-100 | OEt | OCH₂CH=CH₂ | SMe | g |
| IV-101 | OEt | OCH₂CH=CHMe | SMe | g |
| IV-102 | OEt | OPr | SMe | g |
| IV-103 | OMe | O-i-Bu | SMe | g |
| IV-104 | OMe | OBu | SMe | g |
| IV-105 | OMe | OCH₂C(Me)=CH₂ | SMe | g |
| IV-106 | OMe | OCH₂CCH | SMe | g |
| IV-107 | OMe | OCH₂CH₂C(Me)=CH₂ | SMe | g |
| IV-108 | OMe | OCH₂CH=C(Me)₂ | SMe | g |
| IV-109 | OMe | OCH₂CH=CH₂ | SMe | g |
| IV-110 | OMe | OCH₂CH=CHMe | SMe | g |

TABLE 4-continued

| No. | $R^1$ | $R^2$ | $Z^1e$ | Process |
|---|---|---|---|---|
| IV-111 | OMe | OEt | SMe | g |
| IV-112 | OMe | OPr | SMe | g |
| IV-113 | OPr | O-i-Bu | SMe | g |
| IV-114 | OPr | OBu | SMe | g |
| IV-115 | OPr | $OCH_2C(Me)=CH_2$ | SMe | g |
| IV-116 | OPr | $OCH_2CCH$ | SMe | g |
| IV-117 | OPr | $OCH_2CH_2C(Me)=CH_2$ | SMe | g |
| IV-118 | OPr | $OCH_2CH=C(Me)_2$ | SMe | g |
| IV-119 | OPr | $OCH_2CH=CH_2$ | SMe | g |
| IV-120 | OPr | $OCH_2CH=CHMe$ | SMe | g |
| IV-121 | $CF_3$ | OH | SMe | a |
| IV-122 | Et | OH | SMe | a |
| IV-123 | Me | OH | SMe | a |
| IV-124 | OH | OH | SMe | a |
| IV-125 | Ph | OH | SMe | a |
| IV-126 | Pr | OH | SMe | a |
| IV-127 | i-Pr | OH | SMe | a |

Compounds represented in Table 4 can be synthesized as follows:

Each of Compounds IV-121 to IV-127 can be synthesized by using the process (a) in a manner as described in either (1) or (2) below.

(1) 0.1 mol of methyl trifluoroacetoacetate or methyl acetoacetate, about 0.05 mol of methylisothiourea sulfate (2-methyl-2-thiopseudourea sulfate) (i.e., about 1 chemical equivalent of methylisothiourea) and 0.1 mol of sodium methoxide are reacted in 500 ml of methyl alcohol at a temperature of from room temperature to a reflux point for a period of from 4 hours to one night. Then, the reaction mixture is cooled with iced water and 0.1 mol of hydrochloric acid is added thereto. After insoluble matter is filtered off, the solvent is distilled off from the filtrate to afford a crude product, which is then recrystallized to obtain a purified product.

(2) 0.1 mol of ethyl trifluoroacetacetate, ethyl propionylacetate, ethyl acetoacetate, diethyl malonate, ethyl benzoylacetate, ethyl butyrylacetate, or ethyl isobutyrylacetate, about 0.05 mol of methylisothiourea sulfate (2-methyl-2-thiopseudourea sulfate) (i.e., about 1 chemical equivalent of methylisothiourea), and 0.1 mol of sodium ethoxide are reacted in 500 ml of ethyl alcohol at a temperature of from room temperature to a reflux point for a period of from 4 hours to one night. The reaction mixture is allowed to cool to room temperature, and then, while further cooling with iced water, 0.1 mol of hydrochloric acid is added thereto. After insoluble matter is filtered off, the solvent is distilled off from the filtrate to afford a crude product, which is then recrystallized to obtain a purified product.

Each of Compounds IV-1 and IV-2 can be synthesized by the process (b).

0.1 mol of acetylacetone or acetylacetaldehyde dimethylacetal is reacted with 0.1 mol of thiourea in 300 ml of ethyl alcohol containing 10 ml of 35% hydrochloric acid for 5 hours at room temperature. The reaction mixture is allowed to cool to room temperature, and then, while further water-cooling, sodium hydrogen carbonate is added thereto. After stirring for 2 hours, insoluble matter is filtered off. Additional sodium hydrogen carbonate is added to the filtrate, and then, while stirring at room temperature, 0.1 mol of dimethyl sulfate is added and the mixture is stirred for another 3 hours. The solvent is distilled off from the reaction mixture, and thereafter, the residue is redissolved in chloroform and washed with water. After dried over sodium sulfate, the solvent is distilled off to afford a crude product, which is then purified on column chromatography to obtain a purified product.

Each of Compounds IV-3 and IV-5 can be synthesized by the process (c1).

To 1 mol of 4,6-dihydroxy-2-methylthiopyrimidine (Compound IV-124), about 2 to 3 mol of phosphorus oxychloride (identical with phosphoryl chloride) or phosphorus oxybromide (identical with phosphoryl bromide) is added to react at a temperature of 70° C. to 100° C. for a period of about 0.5 hours to about 2 hours while stirring. The reaction mixture is post-treated by using ethyl acetate and water. Ethyl acetate layer is washed successively with aqueous sodium hydrogen carbonate and water, and then, dried over sodium sulfate. The solvent is distilled off to afford an end product, which may be purified on column chromatography as desired.

Each of Compounds IV-4 and IV-6 to IV-10 can be synthesized by the process (c2).

These compounds can be synthesized by using a similar reaction procedure for the synthesis of Compound IV-5, starting from each of Compounds IV-121 to IV-123 and Compounds IV-125 to IV-127 and phosphorus oxychloride employed at a molar ratio of about 1:1 to 1:2. The obtained product may be purified on column chromatography as desired.

Compound IV-11 can be synthesized by the process (e).

0.1 mol of Compound IV-124, 100 ml of dioxane, 20 ml of 40% aqueous sodium hydroxide, and 15 ml of water are stirred at a temperature of 60° C. to 70° C. 0.65 mol of chlorodifluoromethane and 80 ml of aqueous 40% sodium hydroxide are added thereto over a period of 4 hours. At 30 minutes after addition, 30% sulfuric acid is added to adjust pH to about 6. Precipitate is filtered off from the reaction mixture, an organic phase is separated from the filtrate, an aqueous phase is extracted with 75 ml of dioxane to separate another organic phase, which is combined with the previously obtained organic phase. To the combined organic phase, 20 ml of 40% aqueous sodium hydroxide is added, and then, 0.15 mol of chlorodifluoromethane is added thereto over a period of 1 hour at a temperature of 60° C. to 70° C. Precipitate is filtered off from the reaction mixture, an organic phase is separated from the filtrate and the obtained organic phase is washed with 20 ml of 50° C. warm water. Dioxane is distilled off from the organic phase and the residue is distilled under reduced pressure to obtain a purified product.

Each of Compounds IV-12 to IV-17 can be synthesized by the process (f).

Substantially equal molar amounts of Compound IV-4 and sodium hydride are mixed with an excessive amount of 2-methyl-2-propen-1-ol (identical with methallyl alcohol), propargyl alcohol (identical with 2-propyn-1-ol), 3-methyl-3-buten-1-ol, 3-methyl-2-buten-1-ol, allyl alcohol or crotyl alcohol serving also as solvent while removing heat as desired, and stirred for 1 hour at room temperature. The reaction mixture is post-treated by using ethyl acetate and saturated aqueous sodium hydrogen carbonate solution. Organic phase is washed with saturated aqueous sodium chloride and then dried over anhydrous sodium sulfate. Organic solvent is distilled off to obtain an end product, which can then be purified on column chromatography as desired.

Compounds IV-31 to IV-36 can be synthesized by a similar reaction procedure as above, starting from Compound IV-6 in place of Compound IV-4.

Compounds IV-57 to IV-62 can be synthesized by a similar reaction procedure as above, starting from Compound IV-9 in place of Compound IV-4.

Compounds IV-63 to IV-68 can be synthesized by a similar reaction procedure as above, starting from Compound IV-10 in place of Compound IV-4.

Each of Compounds IV-18 to IV-30 can be synthesized by the process (f).

In dimethylformamide or tetrahydrofuran, Compound IV-5 and any one of 2-methyl-1-propanol, butanol, 2-methyl-2-propen-1-ol (identical with methallyl alcohol), 2,2,3,3,3-pentafluoro-1-propanol, propargyl alcohol (identical with 2-propyn-1-ol), 3,3,3-trifuoroethanol, 3-methyl-3-buten-1-ol, 3-methyl-2-buten-1-ol, allyl alcohol, crotyl alcohol, ethanol, methanol and propanol are mixed at a molar ratio of about 1:1 and stirred while cooling with iced water. About 1 to 1.1 molar equivalents of 60% sodium hydride is added thereto and the mixture is stirred for a period of from 3 hours to one night at room temperature. Then, the reaction mixture is post-treated by using ethyl acetate and iced water. An organic phase is washed with aqueous sodium chloride, dried over anhydrous sodium sulfate, and thereafter, organic solvent is distilled off to obtain an end product, which can then be purified on column chromatography as desired.

Each of Compounds IV-37 to IV-45 can be synthesized by the process (f).

Substantially equal molar amounts of the Compound IV-7 and sodium hydride are mixed with an excessive amount of 1-methylethylalcohol, 2-methyl-2-propen-1-ol (identical with methallyl alcohol), propargyl alcohol (identical with 2-propyn-1-ol), 3-methyl-3-buten-1-ol, 3-methyl-2-buten-1-ol, allyl alcohol, crotyl alcohol, ethanol, or methanol serving also as solvent while removing heat as desired, and then stirred about 1 hour at room temperature. The reaction mixture is post-treated by using ethyl acetate and saturated aqueous sodium hydrogen carbonate. An organic phase is washed with saturated aqueous sodium chloride and then dried over anhydrous sodium sulfate. An organic solvent is distilled off to obtain an end product, which can then be purified on column chromatography as desired.

Each of Compounds IV-46 to IV-56 can be synthesized by the process (f).

50 ml of 2-methyl-1-propanol, butanol, 2-methyl-2-propen-1-ol (identical with methallyl alcohol), propargyl alcohol (identical with 2-propyn-1-ol), 3-methyl-3-buten-1-ol, 3-methyl-2-buten-1-ol, allyl alcohol, crotyl alcohol, ethanol, methanol, or propanol is stirred while cooling with iced water. 0.2 mol of 60% sodium hydride is added thereto and the mixture is stirred for 1 hour. Then, 0.1 mol of Compound IV-5 is added thereto to react at a temperature of 35° C. to 45° C. for 4 hours. Alcohol is distilled off from the reaction mixture, then the residue is redissolved in ether, washed with water and dried over sodium sulfate. Ether is distilled off to afford a crude product, which can then be purified on column chromatography to obtain a purified product.

Each of Compounds IV-69 to IV-74 can be synthesized by the process (g).

0.1 mol of 2-methyl-2-propen-1-ol (identical with methallyl alcohol), propargyl alcohol (identical with 2-propyn-1-ol), 3-methyl-3-buten-1-ol, 3-methyl-2-buten-1-ol, allyl alcohol or crotyl alcohol and 50 ml of dimethylacetamide are stirred while cooling with iced water. 0.1 mol of 60% sodium hydride is added thereto and stirred for 0.5 hour to prepare sodium alkoxide.

0.1 mol of Compound IV-18 and 50 ml of dimethylacetamide are stirred while cooling with iced water, then the previously prepared sodium alkoxide is added thereto over a period of 2 hours. After the addition and another 2 hours of stirring, dimethylacetamide is distilled off under reduced pressure from the reaction mixture. Thereafter, the residue is redissolved in ether, washed with water and dried over sodium sulfate. Ether is distilled off to afford a crude product, which can then be purified on column chromatography to obtain a purified product.

Each of Compounds IV-75 to IV-81 can be synthesized by the process (g).

0.1 mol of 2-methyl-1-propanol, 2-methyl-2-propen-1-ol (identical with methallyl alcohol), propargyl alcohol (identical with 2-propyn-1-ol), 3-methyl-3-buten-1-ol, 3-methyl-2-buten-1-ol, allyl alcohol, or crotyl alcohol and 50 ml of dimethylacetamide are stirred while cooling with iced water. 0.1 mol of 60% sodium hydride is added thereto and the mixture is stirred for 0.5 hour to prepare sodium alkoxide.

0.1 mol of Compound IV-19 and 50 ml of dimethylacetamide are stirred while cooling with iced water, then the previously prepared sodium alkoxide is added thereto over a period of 2 hours. After the addition and another 2 hours of stirring, dimethylacetamide is distilled off under reduced pressure from the reaction mixture. Thereafter, the residue is redissolved in ether, washed with water and dried over sodium sulfate. Ether is distilled off to afford a crude product, which can then be purified on column chromatography to obtain a purified product.

Each of Compounds IV-82 to IV-88 can be synthesized by the process (g).

0.1 mol of 2-methyl-2-propen-1-ol (identical with methallyl alcohol), 2,2,3,3,3-pentafluoro-1-propanol, propargyl alcohol (identical with 2-propyn-1-ol), 3-methyl-3-buten-1-ol, 3-methyl-2-buten-1-ol, allyl alcohol, or crotyl alcohol and 50 ml of dimethylacetamide are stirred while cooling with iced water. 0.1 mol of 60% sodium hydride is added thereto and the mixture is stirred for 0.5 hour to prepare sodium alkoxide.

0.1 mol of Compound IV-23 and 50 ml of dimethylacetamide are stirred while cooling with iced water, then the previously prepared sodium alkoxide is added thereto over a period of 2 hours. After the addition and another 2 hours of stirring, dimethylacetamide is distilled off under reduced pressure from the reaction mixture. Thereafter, the residue is redissolved in ether, washed with water and dried over sodium sulfate. Ether is distilled off to afford a crude product, which can then be purified on column chromatography to obtain a purified product.

Each of Compounds IV-89 to IV-93 can be synthesized by the process (g).

0.1 mol of 2-methyl-2-propen-1-ol (identical with methallyl alcohol), propargyl alcohol (identical with 2-propyn- 1-ol), 3-methyl-3-buten-1-ol, 3-methyl-2-buten-1-ol, or crotyl alcohol and 50 ml of dimethylacetamide are stirred while cooling with iced water. 0.1 mol of 60% sodium hydride is added thereto and the mixture is stirred for 0.5 hour to prepare sodium alkoxide.

0.1 mol of Compound IV-26 and 50 ml of dimethylacetamide are stirred while cooling with iced water, then the previously prepared sodium alkoxide is added thereto over a period of 2 hours. After the addition and another 2 hours of stirring, dimethylacetamide is distilled off under reduced pressure from the reaction mixture. Thereafter, the residue is redissolved in ether, washed with water and dried over sodium sulfate. Ether is distilled off to afford a crude product, which can then be purified on column chromatography to obtain a purified product.

Each of Compounds IV-94 to IV-102 can be synthesized by the process (g).

0.1 mol of 2-methyl-1-propanol, butanol, 2-methyl-2-propen-1-ol (identical with methallyl alcohol), propargyl alcohol (identical with 2-propyn-1-ol), 3-methyl-3-buten-1-ol, 3-methyl-2-buten-1-ol, allyl alcohol, crotyl alcohol, or propanol and 50 ml of dimethylacetamide are stirred while cooling with iced water. 0.1 mol of 60% sodium hydride is added thereto and the mixture is stirred for 0.5 hour to prepare sodium alkoxide.

0.1 mol of Compound IV-28 and 50 ml of dimethylacetamide are stirred while cooling with iced water, then the previously prepared sodium alkoxide is added thereto over a period of 2 hours. After the addition and another 2 hours of stirring, dimethylacetamide is distilled off under reduced pressure from the reaction mixture. Thereafter, the residue is redissolved in ether, washed with water and dried over sodium sulfate. Ether is distilled off to afford a crude product, which can then be purified on column chromatography to obtain a purified product.

Each of Compounds IV-103 to IV-112 can be synthesized by the process (g).

0.1 mol of 2-methyl-1-propanol, butanol, 2-methyl-2-propen-1-ol (identical with methallyl alcohol), propargyl alcohol (identical with 2-propyn-1-ol), 3-methyl-3-buten-1-ol, 3-methyl-2-buten-1-ol, allyl alcohol, crotyl alcohol, ethanol or propanol and 50 ml of dimethylacetamide are stirred while cooling with iced water. 0.1 mol of 60% sodium hydride is added thereto and the mixture is stirred for 0.5 hour to prepare sodium alkoxide.

0.1 mol of Compound IV-29 and 50 ml of dimethylacetamide are stirred while cooling with iced water, then the previously prepared sodium alkoxide is added thereto over a period of 2 hours. After the addition and another 2 hours of stirring, dimethylacetamide is distilled off under reduced pressure from the reaction mixture. Thereafter, the residue is redissolved in ether, washed with water and dried over sodium sulfate. Ether is distilled off to afford a crude product, which can then be purified on column chromatography to obtain a purified product.

Each of Compounds IV-113 to IV-120 can be synthesized by the process (g).

0.1 mol of 2-methyl-1-propanol, butanol, 2-methyl-2-propen-1-ol (identical with methallyl alcohol), propargyl alcohol (identical with 2-propyn-1-ol), 3-methyl-3-buten-1-ol, 3-methyl-2-buten-1-ol, allyl alcohol, or crotyl alcohol and 50 ml of dimethylacetamide are stirred while cooling with iced water. 0.1 mol of 60% sodium hydride is added thereto and the mixture is stirred for 0.5 hour to prepare sodium alkoxide.

0.1 mol of Compound IV-30 and 50 ml of dimethylacetamide are stirred while cooling with iced water, then the previously prepared sodium alkoxide is added thereto over a period of 2 hours. After the addition and another 2 hours of stirring, dimethylacetamide is distilled off under reduced pressure from the reaction mixture. Thereafter, the residue is redissolved in ether, washed with water and dried over sodium sulfate. Ether is distilled off to afford a crude product, which can then be purified on column chromatography to obtain a purified product.

Other compounds of the formula (IV) can also be obtained in the same way.

Among 2-benzyloxypyrimidine derivatives of the above formula (I), 2-benzyloxypyrimidine derivatives of the formula (I-b) may be prepared by an process in accordance with Reaction scheme III, starting from 2-benzyloxypyrimidine derivatives of the formula (I-a), which are also included in the formula (I).

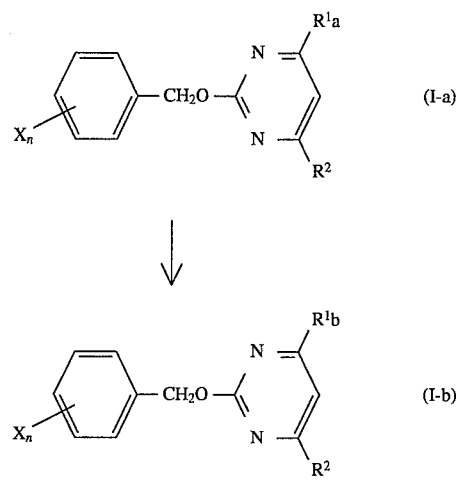

Reaction Scheme III wherein, $R^2$, X, and n are as defined above;

$R^{1a}$ represents a halogen such as chlorine and bromine; and $R^{1b}$ represents:

- $C_1$–$C_4$ haloalkyl such as trifluoromethyl ($CF_3$), fluoromethyl, difluoromethyl, and 2,2,2-trifluoroethyl;
- $C_1$–$C_4$ haloalkoxy such as difluoromethoxy ($OCHF_2$), 1,1,2,2-tetrafluoroethoxy, 2,2,2-trifluoroethoxy ($OCH_2CF_3$), 2-fluoroethoxy, difluoromethoxy, 2-bromo-1,1,2-trifluoroethoxy, 2,2,3,3,3-pentafluoropropoxy ($OCH_2C_2F_5$), 1,1,2,3,3,3-hexafluoropropoxy, and 2-chloro-1,1,2-trifluoroethoxy;
- $C_3$–$C_5$ alkenyloxy such as allyloxy ($OCH_2CH=CH_2$), (2-methyl-2-propenyl)oxy ($OCH_2C(Me)=CH_2$), crotyloxy ($OCH_2CH=CHMe$), (3-methyl-2-butenyl)oxy ($OCH_2CH=C(Me)_2$), and (3-methyl-3-butenyl)oxy ($OCH_2CH_2C(Me)=CH_2$);
- $C_1$–$C_4$ alkylthio such as methylthio (SMe), ethylthio (SEt), and propylthio (SPr); and
- $C_3$–$C_5$ alkynyloxy such as (2-propynyl)oxy ($OCH_2CCH$).

When compounds (I-b) are produced from compounds (I-a) in accordance with the above Reaction scheme III, the reaction conditions are usually as follows.

A compound (I-a) having a halogen atom at the position 4 or 6 is reacted with an alcohol which can induce the nucleophilic substitution of the above halogen atom with $C_1$–$C_4$ alkoxy, $C_1$–$C_4$ haloalkoxy, $C_3$–$C_5$ alkenyloxy, or $C_3$–$C_5$ alkynyloxy, or an alkanethiol which can induce the nucleophilic substitution of the above halogen atom with $C_1$–$C_4$ alkylthio, preferably in an amide such as dimethylformamide, dimethylaCetamide, and N-methyl-2-pyrrolidinone, or an ether such as diethyl ether, dimethoxyethane, diisopropyl ether, tetrahydrofuran, diglyme, and dioxane, in the presence of a basic compound, preferably at a temperature of −20° C. to 150° C. for from about 0.5 to several hours (about 3 hours) to obtain a compound (I-b).

When conducting the above reaction, iodides such as sodium iodide and potassium iodide or crown ethers such as 18-crown-6 and dibenzo-18-crown-6 may be added as a reaction accelerator.

Examples of the alcohols are 2-methyl-1-propanol, butanol, 2-methyl-2-propen-1-ol (identical with methallyl alcohol), 2,2,3,3,3-pentafluoro-1-propanol, propargyl alcohol (identical with 2-propyn-1-ol), 3,3,3-trifluoroethanol, 3-methyl-3-buten-1-ol, 3-methyl-2-buten-1-ol, allyl alcohol, crotyl alcohol, ethanol, methanol, and propanol, etc.

Examples of the alkanethiols are methanethiol, ethanethiol, and propanethiol.

The method of application of 2-benzyloxypyrimidine derivatives of the formula (I) will now be described.

Although the derivatives of the formula (I) may be applied as it is, they are generally applied after formulated with adjuvants into various forms of compositions such as powders, wettable powders, granules, or emulsifiable concentrates.

The composition is usually formulated in such a way that it contains one or more of the derivatives of the formula (I) in an amount of 0.1 to 95% by weight, preferably 0.5 to 90% by weight, more preferably 2 to 70% by weight.

Among adjuvants including carriers, diluents, and surface active agents, suitable solid carriers include talc, kaolin, bentonite, diatomaceous earth, white carbon, clay, and the like. Suitable liquid diluents include water, xylene, toluene, chlorobenzene, cyclohexane, cyclohexanone, dimethylsulfoxide, dimethylformamide, alcohol, and the like.

Surface active agents may be properly selected depending upon their effects, and suitable emulsifying agents include polyoxyethylene alkyl aryl ether, polyoxyethylene solbitan monolaurate, and the like. Suitable dispersing agents include lignin sulfonate, dibutylnaphthalene sulfonate, and the like. Suitable wetting agents are alkyl sulfonates, alkylphenyl sulfonates and the like.

The above mentioned compositions include those which are to be applied as it is and those which are to be applied after diluted to a proper concentration by using a diluent such as water. When applied in diluted form, the concentration of the derivatives of the formula (I) are preferably 0.001 to 1.0% by weight. Application dose of the compounds of the present invention is usually 0.01 to 10 kg/ha, preferably 0.05 to 5 kg/ha.

The concentrations and application doses defined above are varied depending on dosage forms, time of application, way of application, application sites, plants to be treated and the like. Thus modifications thereof are possible without limited to the above defined range. Further, the derivatives of the formula (I) may be used in combination with other active ingredients such as fungicides, insecticides, acaricides, and herbicides.

EXAMPLES

2-Benzyloxypyrimidine derivatives of the present invention, production processes and use thereof will now be described in more detail by way of synthesis examples, formulation examples and test examples. "%" means percent by weight unless otherwise noted.

Synthesis Example 1

Synthesis of
4,6-dibromo-2-(phenylmethoxy)pyrimidine
(Compound I-81)

4,6-dibromo-2-(methysulfonyl)pyrimidine (Compound III-3) (1.5 g, 0.00476 mol) was dissolved in toluene, and benzyl alcohol (Compound II-64) (0.515 g, 0.00476×1.0 mol) was added thereto. While cooling with ice, 60% sodium hydride (0.21 g, 0.00476×1.1 mol) was added while stirring. After stirred for 6 hours, the reaction solution was poured into water and extracted with toluene. The organic phase was washed with saturated aqueous sodium chloride, dried over anhydrous sodium sulfate and filtered, and thereafter, the solvent was distilled off. The residue was purified on silica gel column chromatography (Wakogel C300, 100 ml, ethyl acetate/hexane=20 ml/400 ml) to obtain the compound (I-81) as an oily product from the fraction of 100 ml to 120 ml.

Yield: 0.5 g.

Synthesis Example 2

Synthesis of
4,6-dichloro-2-(phenylmethoxy)pyrimidine
(Compound I-173)

4, 6-Dichloro-2-(methysulfonyl)pyrimidine (Compound III-5) (21.3 g, 93.8 mmol) and benzyl alcohol (Compound II-64) (10.1 g, 93.8×1.0 mmol) were introduced into a 500 ml eggplant type flask, to which dimethylformamide (150 ml) was added to form a solution. While stirring in ice bath, 60% sodium hydride (3.94 g, 93.8×1.05 mmol) which had been washed with hexane was added. After bubbling was ceased, ice bath was removed and the reaction solution was stirred for 2 hours at room temperature. The reaction mixture was poured onto ice and the separated organic matter was extracted with ethyl acetate. The organic phase was washed successively with diluted hydrochloric acid and saturated aqueous sodium chloride, dried over anhydrous sodium sulfate, and thereafter, the solvent was distilled off. The residue was purified on silica gel column chromatography (Wakogel C300, ethyl acetate/hexane=1/50(v/v)) to obtain the compound (I-173) as an oily product.

Yield: 6.5 g (27%).

Synthesis Example 3

Synthesis of
4-chloro-6-methyl-2-(phenylmethoxy)pyrimidine
(Compound I-240)

In tetrahydrofuran, benzyl alcohol (Compound II-64) (1.65 g, 0.010×1.5 mol) and sodium hydride (ca. 0.43 g, (60% in mineral oil), 0.010×1.05 mol) were mixed to form an alkoxide. 4-Chloro-6-methyl-2-(methylsulfonyl)pyrimidine (Compound III-7) (2.10 g, 0.010 mol) was added thereto and was allowed to react for 2 hours at room temperature. The reaction solution was partitioned between ethyl acetate and saturated aqueous sodium hydrogen carbonate, the organic phase was separated and washed with saturated aqueous sodium chloride, dried over anhydrous sodium sulfate and concentrated, and thereafter, purified on silica gel column to obtain the compound (I-240) as an oily product.

Yield: 1.31 g (56%).

$^1$H-NMR (60 MHz, CDCl$_3$, δ): 2.37(3H,s), 5.33(2H,s), 6.73(1H,s), 7.1–7.6(5H,m).

Synthesis Example 4

Synthesis of 4-chloro-6-(3-methyl-2-butenyloxy)-2-(phenylmethoxy)pyrimidine (Compound I-342)

4-Chloro-6-(3-methyl-2-butenyloxy)-2-(methysulfonyl)pyrimidine (Compound III-25) (0.50 g, 1.8 mmol) and benzyl alcohol (Compound II-64) (0.195 g, 1.8×1.0 mmol) were introduced into a 50 ml eggplant type flask, to which dimethyl formamide (10 ml) was added to form a solution. While cooling with ice, 60% sodium hydride (79.5 mg, 1.8×1.1 mmol) which had been washed with hexane was added. After stirred for one night at room temperature, the reaction solution was poured into iced water and extracted with toluene (20 ml). The organic phase was washed with saturated aqueous sodium chloride, dried over anhydrous sodium sulfate, and thereafter, the solvent was distilled off to afford an oily product (0.6 g), which was then purified on silica gel column chromatography (Wakogel C300, 100 ml, hexane/ethyl acetate=300 ml/30 ml) to obtain the compound (I-342).

Yield: 0.3 g (54.7%).

Purity: 91.9% (Rt=10.7 min: ODSF$_{411}$A, acetonitrile/water=70/30 (v/v), 1 ml/min, 250 nm).

Synthesis Example 5

Synthesis of 6-chloro-2-phenylmethoxy-4-(2-propenyloxy)pyrimidine (compound I-343)

4,6-Dichloro-2-(phenylmethoxy)pyrimidine (Compound I-173) (1.5 g, 5.9 mmol) and allyl alcohol (0.342 g, 5.9×1.0 mmol) were introduced into a 50 ml eggplant type flask, to which dimethylformamide (20 ml) was added to form a solution. While cooling with ice, 60% sodium hydride (0.247 g, 5.9×1.05 mmol) which had been washed with hexane was added. After stirred for one night at room temperature, the reaction solution was poured into iced water and extracted with toluene (40 ml). The organic phase was washed with saturated aqueous sodium chloride, dried over anhydrous sodium sulfate, and thereafter, the solvent was distilled off to afford an oily product, which was then purified on silica gel column chromatography (Wakogel C300, 300 ml, hexane/ethyl acetate=25/1000(v/v)) to obtain the compound (I-343).

Yield: 0.7 g (42.9%).

Synthesis Example 6

Synthesis of 4-chloro-6-methoxy-2-(phenylmethoxy)pyrimidine (Compound I-346)

4-Chloro-6-methoxy-2-(methylsulfonyl)pyrimidine (Compound III-29) (0.80 g, 0.0036 mol) and benzyl alcohol (Compound II-64) (0.39 g, 0.0036 mol) were dissolved in toluene (10 ml), and then 60% sodium hydride (0.16 g, 0.0036×1.1 mol) was added while cooling with ice. After stirred for one night at room temperature, the reaction solution was poured into water and extracted with ethyl acetate. The organic phase was washed with saturated aqueous sodium chloride, dried over anhydrous sodium sulfate and filtered, and thereafter, the solvent was distilled off to afford a crude product (0.92 g), which was then purified on silica gel column chromatography to obtain the compound (I-346) as an oily product.

Yield: 0.5 g.

Synthesis Example 7

Synthesis of 4-ethoxy-6-methyl-2-(phenylmethyl)pyrimidine (Compound I-361)

To benzyl alcohol (Compound II-64) (0.35 g, 0.0016×2.0 mol) in tetrahydrofuran, sodium hydride (0.085 g, (60% in mineral oil), 0.0016×1.3 mol) and 4-ethoxy-6-methyl-2-(methylsulfonyl)pyrimidine (Compound III-44) (0.35 g, 0.0016 mol) prepared as described in Reference synthesis example 1 below were successively added and the solution was allowed to react for about 1 hour at room temperature.

Then, the reaction solution was partitioned between ethyl acetate and saturated aqueous sodium hydrogen carbonate, organic phase was washed with saturated aqueous sodium chloride, and thereafter, dried over anhydrous sodium sulfate. The dried organic phase was concentrated with a rotary evaporator, then, in a tubular oven, unreacted starting materials were distilled off under reduced pressure with a vacuum pump, and thereafter, purified on silica gel column to obtain the compound (I-361).

Yield: 0.32 g (81%).

Synthesis Example 8

Synthesis of 4,6-dimethoxy-2-(phenylmethoxy)pyrimidine (Compound I-372)

Benzyl alcohol (Compound II-64) (0.434 g, 4.0 mmol) and 2-chloro-4,6-dimethoxypyrimidine were dissolved in dimethylformamide (10 ml) and cooled with ice. Sodium hydride (168 mg, 4.0×1.05 mmol) which had been washed with hexane (1 ml×2) was added thereto. After allowed to react for 2 hours, the reaction solution was poured onto ice and extracted with toluene. The organic phase was concentrated and thereafter purified on silica gel column chromatography (Wakogel C300, 100 ml, ethyl acetate/hexane=30 ml/300 ml) to obtain the compound (I-372).

Yield: 600 mg (61%).

Synthesis Example 9

Synthesis of 4,6-dimethylthio-2-(phenylmethoxy)pyrimidine (Compound I-2007)

To 15% aqueous sodium thiomethoxide (11 g, 0.0118×2.0 mol) dissolved in dimethylformaldehyde, 4,6-dichloro-2-(phenylmethoxy)pyrimidine (Compound I-173) (3 g, 0.0118×1.0 mol) was added and the solution was stirred for about 3 hours at room temperature.

The reaction solution was partitioned between ethyl acetate and saturated aqueous sodium hydrogen carbonate, then the organic phase was separated and washed with saturated aqueous sodium chloride, and thereafter, dried, concentrated and purified on silica gel column to obtain the compound (I-2007) as an oily product.

Yield: 3.2 g (98%).

Synthesis Example 10

Synthesis of 4-chloro-6-(ethylthio)-2-(phenylmethoxy)pyrimidine (Compound I-2014)

Ethanethiol (0.366 g, 0.0059×1.0 mol) was dissolved in tetrahydrofuran and sodium hydride (0.24 g, (ca. 60% in mineral oil), 0.0059×1.0 mol) was added thereto. The resulting solution was added dropwise to 4,6-dichloro-2-(phenylmethoxy)pyrimidine (Compound I-173) (1.5 g, 0.0059 mol) dissolved in tetrahydrofuran and then the solution was stirred for about 3 hours at room temperature.

In order to completely remove the unreacted starting materials (Compound I-173), 40% aqueous methylamine (0.23 g, 0.0059×0.5 mol) was added and stirred for about 1 hour at room temperature. The reaction solution was poured into water and extracted with ethyl acetate. The organic phase was separated and washed with saturated aqueous sodium chloride, and thereafter, dried, concentrated and purified on silica gel column to obtain the compound (I-2014).

Yield: 1.55 g (94%).
m.p. 55° to 57° C.

Reference Synthesis Example 1

Synthesis of 4,6-dibromo-2-(methylsulfonyl)pyrimidine (Compound III-3)

(1) Synthesis of an intermediate, 4,6-dibromo-2-(methylthio)pyrimidine (Compound IV-3)

Into a 300 ml eggplant type flask, 4,6-dihydroxy-2-(methylthio)pyrimidine (Compound IV-124) (12.5 g, 0.079 mol) and phosphoryl tribromide (49.8 g, 0.079×2.1 mol) were introduced, and the flask was immersed in 80° C. oil bath and the solution was stirred for 30 minutes. The reaction mixture was cooled to room temperature, then ethyl acetate was added thereto and dissolved. The resulting solution was poured onto ice and an organic phase was separated. The separated organic phase was washed with saturated aqueous sodium chloride, dried over anhydrous sodium sulfate and filtered, and thereafter, the solvent was distilled off. The residue was purified on silica gel column chromatography (Wakogel C300, 300 ml, ethyl acetate/hexane=35 ml/700 ml) to obtain the compound (IV-3) as a white crystalline product from the fraction of 20 ml to 480 ml.

Yield: 14.6 g.
m.p. 90° to 92° C.

(2) Synthesis of Compound III-3 from the intermediate

Into a 100 ml eggplant type flask, the compound (IV-3) (5.7 g, 20.1 mmol) which was the intermediate obtained in the step (1) above was introduced and acetic acid (50 ml) was added and dissolved. 31% aqueous hydrogen peroxide (4.5 g, 20.1×2.1 mmol) was added thereto and allowed to react at 100° C. for 3 hours.

Since HPLC monitoring showed the presence of 13.2% of unreacted starting materials (Rt=5.1 min, acetonitrile/water= 70/30 (v/v), 1 ml/min, 250 nm), 31% aqueous hydrogen peroxide (1.0 g, 20.1×0.47 mmol) was further added thereto and allowed to react for 1 hour. After cooled to room temperature, the reaction solution was poured into iced water and extracted with toluene. After washed with saturated aqueous sodium chloride, the organic phase was dried over anhydrous sodium sulfate and the solvent was distilled off to obtain the compound (III-3) as a white crystalline product.

Yield: 4.5 g (72.5%).
Purity: 97.5% (Rt=2.3 min: ODS411A, acetonitrile/water= 70/30(v/v), 1 ml/min, 250 nm).
m.p. 121° to 124° C.

Reference Synthesis Example 2

Synthesis of 4,6-dichloro-2-(methylsulfonyl)pyrimidine (Compound III-5)

(1) Synthesis of an intermediate, 4,6-dichloro-2-(methylthio)pyrimidine (Compound IV-5)

Into a 500 ml eggplant type flask, 4,6-dihydroxy-2-(methylthio)pyrimidine (Compound IV-124) (75.0 g, 474 mmol) and phosphorus oxychloride (250 g, 474×3.44 mmol) were introduced. After stirred for 2 hours at 100° C., HPLC monitoring showed the presence of 96.8% of the end product (Rt=4.5 min, acetonitrile/water=70/30 (v/v), 1 ml/min, 250 nm). After allowed to cool to room temperature, the reaction solution was carefully poured into iced water, extracted with ethyl acetate (500 ml). The organic phase was washed successively with saturated aqueous sodium hydrogen carbonate and saturated aqueous sodium chloride, then dried over anhydrous sodium sulfate, and thereafter, the solvent was distilled off to obtain the compound (IV-5).

Yield: 92.3 g (99.8%).
Purity 96.8%. (Rt=4.5 min: ODS411A, acetonitrile/water=70/30 (v/v), 1 ml/min, 250 nm).

(2) Synthesis of Compound III-5 from the intermediate

Into a 500 ml eggplant type flask, the compound (IV-5) (25.0 g, 128 mmol) obtained in the above step (1) was introduced, and dissolved by the addition of acetic acid (100 ml). While stirring, 31% aqueous hydrogen peroxide (30.9 g, 128×2.2 mmol) was added thereto. After stirred for one night at room temperature, HPLC monitoring showed the presence of 75% of remaining unreacted starting material (Rt=4.6 min, acetonitrile/water=70/30 (v/v), 1 ml/min, 250 nm). Thus, the reaction solution was heated to 80° C. and allowed to react for another 3 hours.

HPLC monitoring showed the presence of 95.1% of the end product (Rt=2.3 min). After cooled to room temperature, the reaction solution was poured into iced water and extracted with ethyl acetate (200 ml). After washed with saturated aqueous sodium chloride, the organic phase was dried over anhydrous sodium sulfate, and thereafter, the solvent was distilled off to obtain the compound (III-5) as a white crystalline product.

Yield: 22.4 g (77.0%).
Purity: 99.4% (Rt=2.3 min: ODS411A, acetonitrile/water=70/30(v/v), 1 ml/min, 250 nm).
m.p. 115° to 121° C.

Reference Synthesis Example 3

Synthesis of 4-chloro-6-methyl-2-(methylsulfonyl)pyrimidine (Compound III-7)

4-Chloro-6-methyl-2-(methylthio)pyrimidine (Compound IV-7) (2.0 g, 0.0114 mol) was dissolved in chloroform, m-chloroperbenzoic acid (5.64 g, (purity ca. 70%), 0.0114×2.0 mol) was added thereto and the solution was stirred for about 2 hours at room temperature. The reaction solution was partitioned between chloroform and saturated aqueous sodium hydrogen carbonate to separate an organic phase, which was then washed with saturated aqueous sodium chloride, dried over anhydrous sodium sulfate, concentrated, and thereafter, purified on silica gel column to obtain the compound (III-7).

Yield: 2.25 g (95%).

m.p. 67° to 70° C.

$^1$H-NMR (60 MHz, CDCl$_3$, δ): 2.63(3H,s), 3.30(3H,s), 7.38 (1H,s).

Reference Synthesis Example 4

Synthesis of
4-chloro-6-methoxy-2-(methylsulfonyl)pyrimidine
(Compound III-29)

(1) Synthesis of an intermediate, 4-chloro-6-methoxy-2-(methylthio)pyrimidine (Compound IV-29)

4,6-dichloro-2-(methylthio)pyrimidine (Compound IV-5) (19.5 g, 0.100 mol) was dissolved in tetrahydrofuran (200 ml) just after distilled, then methyl alcohol (3.2 g, 0.100×1.0 mol) was added thereto. While cooling with ice, 60% sodium hydride (4.4 g, 0.100×1.1 mol) was added thereto while stirring. After stirred for 3 hours, the reaction solution was poured into water and extracted with toluene. The organic phase was washed with saturated aqueous sodium chloride, dried over anhydrous sodium sulfate and filtered, and thereafter, the solvent was distilled off to obtain the compound (IV-29).

Yield: 19.0 g.

$^1$H-NMR (60 MHz, CDCl$_3$, δ): 2.47(3H,s), 3.85(3H,s), 6.27 (1H,s)

(2) Synthesis of Compound III-29 from the intermediate

The compound (IV-29) (19.0 g, 0.100 mol) which was the intermediate obtained in the step (1) above, was dissolved in acetic acid (200 ml), then 31% aqueous hydrogen peroxide (25.2 g, 0.100×2.3 mol) was added, and the solution was heated to 100° C. while stirring. After stirred for 2 hours, the reaction solution was poured into water and extracted with ethyl acetate. The organic phase was washed with saturated aqueous sodium chloride, dried over anhydrous sodium sulfate and filtered, and thereafter, the solvent was distilled off to obtain a crude product (20.0 g), which was then purified on silica gel column chromatography (Wakogel C300, 300 ml, ethyl acetate/hexane=400 ml/400 ml) to obtain the compound (III-29) as a white crystalline product from the fraction of 300 ml to 600 ml.

Yield: 11.5 g.

m.p. 68° to 74° C.

$^1$H-NMR (60 MHz, CDCl$_3$, δ): 3.30(3H,s), 4.07(3H,s), 6.87 (1H,s).

Reference Synthesis Example 5

Synthesis of 4-chloro-6-(3-methyl-2-butenyloxy)-2-(methylsulfonyl)pyrimidine (Compound III-25)

(1) Synthesis of an intermediate, 4-chloro-6-(3-methyl-2-butenyloxy)-2-(methylthio)pyrimidine (Compound IV-25)

Into a 100 ml eggplant type flask, 4,6-dichloro-2-(methylthio)pyrimidine (Compound IV-5) (7.4 g, 37.9 mmol) and 3-methyl-2-buten-1-ol (3.27 g, 37.9×1.0 mmol) were introduced, then dimethyl formaldehyde (20 ml) was added thereto to form a solution. 60% sodium hydride (1.59 g, 7.9×1.05 mmol) which had been washed with hexane was added thereto while cooling with ice.

After stirred for one night at room temperature, the reaction solution was poured into iced water and extracted with toluene (50 ml). The organic phase was washed with saturated aqueous sodium chloride and dried over anhydrous sodium sulfate, and thereafter, the solvent was distilled off to obtain an oily product, which was then purified on silica gel column chromatography (Wakogel C300, 300 ml, hexane= 1000 ml) to obtain the compound (IV-25).

Yield: 7.3 g (78.5%).

Purity: 91.2%. (Rt=8.9 min: ODSF$_{411}$A, acetonitrile/water=70/30(v/v), 1 ml/min, 250 nm)

$^1$H-NMR (60 MHz, CDCl$_3$, δ): 1.70(6H,s), 2.48(3H,s), 4.6–4.9(2H,m), 5.2–5.6(1H, m), 6.27(1H,s)

(2) Synthesis of Compound III-25 from the intermediate

Into a 100 ml eggplant type flask, the compound (IV-25) (2.45 g, 10.0 mmol) which was the intermediate obtained in the above step was introduced, then dichloromethane (40 ml) was added thereto to form a solution. While cooling with ice, m-chloroperbenzoic acid (3.45 g, 10.0×2.0 mmol) was added by small portions. 1 hour later from the end of addition, ice bath was removed, and the reaction solution was stirred one night at room temperature. Saturated aqueous sodium hydrogen carbonate was added to the reaction solution and shaken to separate an organic phase. The obtained organic phase was then washed with saturated aqueous sodium chloride and dried over anhydrous sodium sulfate, thereafter, the solvent was distilled off to obtain an oily product (2.5 g), which was purified on silica gel column chromatography (Wakogel C300, 300 ml, hexane/ethyl acetate=300 ml/150 ml) to obtain the compound (III-25) from the fraction of 300 ml to 380 ml.

Yield: 0.7 g (2.53%).

Oily product.

$^1$H-NMR (60 MHz, CDCl$_3$, δ): 1.77(6H,s), 3.30(3H,s), 4.9–5.1(2H, d,7Hz), 5.3–5.6(1H,m), 6.90(1H,s)

Reference Synthesis Example 6

Synthesis of
4-ethoxy-6-methyl-2-methylsulfonylpyrimidine
(Compound III-44)

(1) Synthesis of an intermediate, 4-ethoxy-6-methyl-2-(methylthio)pyrimidine (Compound IV-44)

To sodium hydride (2.75 g (60% in mineral oil), 0.046× 1.5 mmol) dissolved in ethanol (20 ml), 4-chloro-6-methyl-2-methylmercaptopyrimidine (Compound IV-7) (8.0 g, 0.046 mmol) was added and the solution was stirred for about 1 hour at room temperature.

Then, the reaction solution was partitioned between ethyl acetate and saturated aqueous sodium hydrogen carbonate. The organic phase was washed with saturated aqueous sodium chloride and dried over anhydrous sodium sulfate. After dried, the residue was concentrated and purified on silica gel column to obtain the compound (IV-44).

Yield: 6.02 g (71%).

(2) Synthesis of Compound III-44 from the intermediate

The compound (IV-44) (5.82 g, 0.0316 mol) which was the intermediate obtained by the above step (1), was dissolved in chloroform, then m-chloroperbenzoic acid (15.6 g, 0.0316×2.0 mol) was added thereto and the solution was allowed to react for about 2 hours at room temperature. The reaction solution was partitioned between chloroform and saturated aqueous sodium hydrogen carbonate, organic layer was washed with saturated aqueous sodium chloride, and then dried over anhydrous sodium sulfate. After dried, the residue was concentrated and purified on silica gel column to obtain the compound (III-44).

Yield: 3.87 g (57%).

Physico-chemical properties of the compounds produced in the Synthesis examples 1 to 10 and those produced in accordance with the Synthesis examples 1 to 10 are shown in Table 5.

TABLE 5

| No. | property or m.p. (°C.) | NMR (60 MHz, CDCl$_3$, δ) |
|---|---|---|
| I-1 | oily | 5.44(2H, s), 6.83(1H, t, J=4.8Hz), 7.0–7.8(4H, m), 8.43(2H, d, J=4.8Hz) |
| I-2 | 101–102 | 5.49(2H, s), 6.83(1H, t, J=4.8Hz), 7.0–7.6(4H, m), 8.42(2H, d, J=4.8Hz) |
| I-3 | 65–67 | 5.36(2H, s), 6.87(1H, t, J=4.8Hz), 7.33(4H, s), 8.46(2H, d, J=4.8Hz) |
| I-4 | oily | 2.44(3H, s), 5.50(2H, s), 6.76(1H, d, J=5.0Hz), 6.9–7.8(4H, m), 8.31(1H, d, J=5.0Hz) |
| I-5 | 61–63 | 2.42(3H, s), 5.34(2H, s), 6.74(1H, d, J=5.0Hz), 7.0–7.6(4H, m), 8.28(1H, d, J=5.0Hz) |
| I-6 | 54–57 | 2.41(3H, s), 5.35(2H, s), 6.74(1H, d, J=5.0Hz), 7.1–7.7(4H, m), 8.30(1H, d, J=5.0Hz) |
| I-7 | 66–67 | 2.42(3H, s), 5.36(2H, s), 6.90(1H, d, J=5.0Hz), 7.0–7.7(5H, m), 8.25(1H, d, J=5.0Hz) |
| I-8 | 48–53 | 2.33(6H, s), 5.43(2H, s), 6.58(1H, s), 7.0–7.7(4H, m) |
| I-9 | oily | 2.36(6H, s), 5.30(2H, s), 6.59(1H, s), 7.1–7.8(4H, m) |
| I-10 | oily | 2.34(6H, s), 5.41(2H, s), 6.56(1H, s), 6.6–7.7(4H, m) |
| I-11 | 39–40 | 2.36(6H, s), 5.41(2H, s), 6.58(1H, s), 6.8–7.7(4H, m) |
| I-12 | 50–54 | 2.34(6H, s), 3.76(3H, s), 5.37(2H, s), 6.55(1H, s), 6.6–7.6(4H, m) |
| I-13 | oily | 2.34(6H, s), 5.34(2H, s), 6.56(1H, s), 6.6–7.5(4H, m) |
| I-14 | oily | 2.35(6H, s), 5.30(2H, s), 6.58(1H, s), 7.1–7.8(4H, m) |
| I-15 | oily | 2.36(6H, s), 3.73(3H, s), 5.32(2H, s), 6.57(1H, s), 6.5–7.4(4H, m) |
| I-16 | oily | 2.33(6H, s), 5.30(2H, s), 6.57(1H, s), 7.1–7.5(4H, m) |
| I-17 | oily | 2.36(6H, s), 5.30(2H, s), 6.59(1H, s), 6.7–7.7(4H, m) |
| I-18 | oily | 2.34(6H, s), 5.27(2H, s), 6.56(1H, s), 7.0–7.6(4H, m) |
| I-19 | oily | 2.38(6H, s), 3.42(3H, s), 5.24(2H, s), 6.55(1H, s), 6.80(2H, d, J=8.3Hz), 7.37(2H, d, J=8.3Hz) |
| I-20 | oily | 2.33(6H, s), 5.16(2H, s), 6.47(1H, s), 7.1–7.7(5H, m) |
| I-21 | oily | 1.26(6H, d, J=6.3Hz), 2.27(3H, s), 5.14(1H, sept., J=6.3Hz), 5.30(2H, s), 6.06(1H, s), 6.4–7.7(3H, m) |
| I-22 | oily | 1.28(6H, d, J=6.3Hz), 1.33(3H, t, J=6.3Hz), 2.29(3H, s), 3.98(2H, q, J=6.3Hz), 5.28(1H, sept., J=6.3Hz), 5.39(2H, s), 6.05(1H, s), 6.6–7.6(4H, m) |
| I-23 | oily | 1.30(6H, d, J=6.3Hz), 2.30(3H, s), 5.29(1H, sept., J=6.3Hz), 5.27(2H, s), 6.11(1H, s), 6.8–7.5(3H, m) |
| I-24 | oily | 2.36(3H, s), 4.67(2H, q, J=8.3Hz), 5.35(2H, s), 6.29(1H, s), 7.1–7.7(5H, m) |
| I-25 | 70–72 | 3.83(6H, s), 5.33(2H, bs), 5.63(1H, s), 6.9–7.3(3H, m) |
| I-26 | 81–84 | 2.13(3H, s), 2.27(3H, s), 3.73(3H, s), 3.86(6H, s), 5.33(2H, bs), 5.67(1H, s), 6.60(1H, d, J=8Hz), 7.20(1H, d, J=8Hz) |
| I-27 | 68–70 | 3.77(3H, s), 3.80(3H, s), 3.83(6H, s), 5.40(2H, s), 5.60(1H, s), 6.8–7.1(3H, m) |
| I-28 | 125–127 | 3.83(6H, s), 5.40(2H, s), 5.65(1H, s), 7.1–7.5(3H, m) |
| I-29 | 66–68 | 3.83(6H, s), 5.33(2H, s), 5.60(1H, s), 6.6–7.5(3H, m) |
| I-30 | 88–90 | 2.30(3H, s), 2.33(3H, s), 3.83(6H, s), 5.30(2H, s), 5.63(1H, s), 6.8–7.4(4H, m) |
| I-31 | 82–84 | 2.13(3H, s), 3.73(3H, s), 3.76(3H, s), 3.83(6H, s), 5.33(2H, s), 5.63(1H, s), 6.57(1H, d, J=8Hz), 7.23(1H, d, J=8Hz) |
| I-32 | 86–88 | 3.73(6H, s), 3.83(6H, s), 5.30(2H, s), 5.60(1H, s), 6.3–6.5(2H, m), 7.27(1H, d, J=8Hz) |
| I-33 | 74–76 | 3.83(6H, s), 5.43(2H, s), 5.67(1H, s), 7.1–7.6(3H, m) |
| I-34 | 68–70 | 3.76(6H, s), 5.30(2H, bs), 5.57(1H, s), 6.7–7.3(3H, m) |
| I-35 | 35–39 | 2.27(3H, s), 2.33(3H, s), 3.83(6H, s), 5.33(2H, s), 5.63(1H, s), 6.9–7.3(3H, m) |
| I-36 | 82–84 | 3.67(3H, s), 3.70(3H, s), 3.83(6H, s), 5.37(2H, s), 5.63(1H, s), 6.7–7.5(3H, m) |
| I-37 | 94–96 | 3.87(6H, s), 5.57(2H, s), 5.67(1H, s), 7.2–7.3(3H, m) |
| I-38 | 88–90 | 3.83(6H, s), 5.40(2H, bs), 5.63(1H, s), 6.6–7.4(3H, m) |
| I-39 | 38–40 | 1.33(3H, t, J=7Hz), 3.83(6H, s), 4.00(2H, q, J=7Hz), 5.40(2H, s), 5.63(1H, s), 6.7–7.5(3H, m) |
| I-40 | 88–91 | 3.83(6H, s), 5.43(2H, d, J=2Hz), 5.63(1H, s), 6.7–7.3(3H, m) |
| I-41 | 66–68 | 3.83(6H, s), 5.30(2H, s), 5.60(1H, s), 7.0–7.3(3H, m) |
| I-42 | oily | 3.73(3H, s), 3.83(6H, s), 5.37(2H, s) 5.60(1H, s), 6.7–7.5(4H, m) |
| I-43 | 81–83 | 3.83(6H, s), 5.33(2H, s), 5.63(1H, s) 6.7–7.9(4H, m) |
| I-44 | 75–77 | 3.80(9H, s), 3.87(6H, s), 5.27(2H, s), 5.63(1H, s), 6.67(2H, s) |
| I-45 | 93–95 | 3.83(6H, s), 5.27(2H, s), 5.63(1H, s), 7.1–7.6(3H, m) |
| I-46 | 72–74 | 3.83(6H, s), 5.27(2H, s), 5.63(1H, s), 6.9–7.4(3H, m) |
| I-47 | 37–39 | 2.20(6H, s), 3.83(6H, s), 5.27(2H, s), 5.60(1H, s), 7.0–7.2(3H, m) |
| I-48 | 115–117 | 3.83(6H, s), 5.27(2H, s), 5.63(1H, s), 7.2–7.4(3H, m) |
| I-49 | 94–95 | 3.83(6H, s), 5.30(2H, s), 5.67(1H, s), 6.5–7.1(3H, m) |
| I-50 | 58–61 | 2.23(6H, s), 3.83(6H, s), 5.23(2H, s), 5.60(1H, s), 6.83(1H, bs), 7.00(2H, bs) |
| I-51 | 60–62 | 3.70(6H, s), 3.83(6H, s), 5.27(2H, s), 5.63(1H, s), 6.30(1H, t, J=3Hz), 6.57(2H, d, J=3Hz) |
| I-52 | 123–125 | 3.83(6H, s), 5.40(2H, s), 5.63(1H, s), 7.73(1H, bs), 7.83(2H, bs) |
| I-53 | 80–82 | 3.83(6H, s), 5.37(2H, s), 5.63(1H, s), 7.3–7.7(4H, m) |
| I-55 | 60–62 | 1.40(3H, t, J=7Hz), 3.77(3H, s), 3.83(6H, s), 4.03(2H, q, J=7Hz), 5.23(2H, s), 5.60(1H, s), 6.7–7.2(3H, m) |
| I-56 | 144–146 | 3.87(6H, s), 5.43(2H, bs), 5.67(1H, s), 7.2–8.3(4H, m) |
| I-57 | oily | 3.80(6H, s), 4.63(2H, s), 5.27(2H, s), 5.60(1H, s), 6.7–7.4(9H, m) |
| I-58 | oily | 3.67(3H, s), 3.80(6H, s), 5.27(2H, s), 5.60(1H, s), 6.8–7.3(4H, m) |
| I-59 | oily | 3.83(6H, s), 5.27(2H, s), 5.63(1H, s), 6.8–7.8(4H, m) |
| I-60 | oily | 1.20(6H, d, J=7Hz), 2.87(1H, sept., J=7Hz), 3.83(6H, s), 5.30(2H, s), 5.60(1H, s), 7.0–7.3(4H, m) |
| I-61 | oily | 3.83(6H, s), 5.37(2H, s), 5.63(1H, s), 7.50(4H, s) |
| I-62 | 80–82 | 1.40(3H, t, J=7Hz), 3.80(3H, s), 3.87(6H, s), 4.00(2H, q, J=7Hz), 5.23(2H, s), 5.60(1H, s), 6.7–7.2(3H, m) |
| I-63 | 79–81 | 3.83(6H, s) , 5.37(2H, s), 5.63(1H, s), 7.1–7.6(9H, m) |
| I-64 | 126–128 | 3.73(3H, s), 3.83(6H, s), 5.30(2H, s), |

TABLE 5-continued

| No. | property or m.p. (°C.) | NMR (60 MHz, CDCl₃, δ) |
|---|---|---|
| I-65 | 95–98 | 5.63(1H, s), 6.67(1H, d, J=8Hz), 7.20(1H, d, J=3Hz), 7.43(1H, dd, J=8Hz, J=3Hz) 3.77(3H, s), 3.83(6H, s), 5.03(2H, s), 5.23(2H, s), 5.60(1H, s), 6.7–7.4(8H, m) |
| I-66 | 73–75 | 3.80(6H, s), 4.93(2H, s), 5.23(2H, s), 5.60(1H, s), 6.7–7.4(9H, m) |
| I-67 | oily | 2.40(3H, s), 3.83(6H, s), 5.23(2H, s), 5.60(1H, s), 7.0–7.6(4H, m) |
| I-68 | oily | 3.63(3H, s), 3.80(6H, s), 5.23(2H, s), 5.60(1H, s), 6.77(2H, d, J=8Hz), 7.30(2H, d, J=8Hz) |
| I-81 | oily | 5.20(2H, s), 7.10(1H, s), 7.1–7.8(5H, m) |
| I-173 | oily | 5.33(2H, s), 6.90(1H, s), 7.2–7.5(5H, m) |
| I-240 | oily | 2.37(3H, s), 5.33(2H, s), 6.73(1H, s), 7.1–7.6(5H, m) |
| I-342 | oily | 1.70(6H, s), 4.75(2H, d, 7Hz), 5.2–5.5(1H, m), 5.33(2H, s), 6.27(1H, s), 7.1–7.5(5H, m) |
| I-343 | oily | 4.7–4.9(2H, m), 5.0–6.3(3H, m), 5.27(2H, s), 6.23(1H, s), 7.1–7.47(5H, m) |
| I-346 | oily | 3.80(3H, s), 5.30(2H, s), 6.20(1H, s), 7.1–7.5(5H, m) |
| I-354 | oily | 1.25(6H, d, J=6.3Hz), 2.29(3H, s), 5.24(1H, sept., J=6.3Hz), 5.30(2H, s), 6.56(1H, s), 7.1–7.6(5H, m) |
| I-359 | oily | 2.31(3H, s), 4.5–4.9(2H, m), 4.9–5.6(2H, m), 5.32(2H, s), 5.6–6.2(1H, m), 6.15(1H, s), 6.9–7.6(5H, m) |
| I-361 | oily | 1.30(3H, t, J=6.9Hz), 2.29(3H, s), 4.29(2H, q, J=6.9Hz), 5.31(2H, s), 6.09(1H, s), 7.1–7.7(5H, m) |
| I-362 | oily | 2.30(3H, s), 3.85(3H, s), 5.33(2H, s), 6.12(1H, s), 7.1–7.6(5H, m) |
| I-371 | 39–41 | 1.30(6H, t, J=6.9Hz), 4.26(4H, q, J=6.9Hz), 5.30(2H, s), 5.57(1H, s), 7.1–7.6(5H, m) |
| I-372 | 64–66 | 3.80(6H, s), 5.30(2H, s), 5.60(1H, s), 7.1–7.5(5H, m) |
| I-464 | oily | 1.24(6H, d, J=6.3Hz), 2.28(3H, s), 5.24(1H, sept., J=6.3Hz), 5.41(2H, s), 6.06(1H, s), 6.9–7.7(4H, m) |
| I-471 | oily | 1.29(3H, t, J=6.9Hz), 2.31(3H, s), 4.30(2H, q, J=6.9Hz), 5.44(2H, s), 6.12(1H, s), 7.0–7.7(4H, m) |
| I-472 | oily | 2.30(3H, s), 3.85(3H, s), 5.44(2H, s), 6.14(1H, s), 7.0–7.8(4H, m) |
| I-482 | 80–82 | 3.83(6H, s), 5.47(2H, s), 5.63(1H, s), 7.1–7.6(4H, m) |
| I-574 | oily | 1.25(6H, d, J=6.3Hz), 2.28(3H, s), 5.27(1H, sept., J=6.3Hz), 5.37(2H, s), 6.06(1H, s), 6.7–7.6(4H, m) |
| I-581 | oily | 1.30(3H, t, J=6.9Hz), 2.30(3H, s), 4.32(2H, q, J=6.9Hz), 5.40(2H, s), 6.13(1H, s), 6.6–7.8(4H, m) |
| I-582 | 48–49.5 | 2.30(3H, s), 3.86(3H, s), 5.43(2H, s), 6.14(1H, s), 6.7–7.7(4H, m) |
| I-592 | 67–69 | 3.83(6H, s), 5.40(2H, s), 5.60(1H, s), 6.8–7.6(4H, m) |
| I-692 | oily | 2.32(3H, s), 3.85(3H, s), 5.45(2H, s), 6.16(1H, s), 6.8~7.8(4H, m) |
| I-702 | 67–69 | 3.83(6H, s), 5.43(2H, s), 5.63(1H, s), 7.0–7.6(4H, m) |
| I-812 | 68–70 | 2.37(3H, s), 3.83(6H, s), 5.33(2H, s), 5.63(1H, s), 7.1–7.5(4H, m) |
| I-904 | oily | 1.26(6H, d, J=6.3Hz), 2.29(3H, s), 5.26(1H, sept., J=6.3Hz), 5.28(2H, s), 6.08(1H, s), 7.1–7.6(4H, m) |
| I-911 | oily | 1.32(3H, t, J=6.3Hz), 2.32(3H, s), 4.28(2H, q, J=6.3Hz), 5.34(2H, s), 6.16(1H, s), 7.0–7.6(4H, m) |
| I-912 | oily | 2.30(3H, s), 3.85(3H, s), 5.29(2H, s), 6.13(1H, s), 7.0–7.6(4H, m) |
| I-922 | 78–80 | 3.83(6H, s), 5.27(2H, s), 5.63(1H, s), 7.1–7.5(4H, m) |
| I-1014 | oily | 1.27(6H, d, J=6.3Hz), 2.29(3H, s), 5.25(1H, sept., J=6.3Hz), 5.29(2H, s), 6.07(1H, s), 6.6–7.4(4H, m) |
| I-1021 | oily | 1.31(3H, t, J=6.9Hz), 2.31(3H, s), 4.30(2H, q, J=6.9Hz), 5.31(2H, s), 6.11(1H, s), 6.6–7.6(4H, m) |
| I-1022 | oily | 2.30(3H, s), 3.84(3H, s), 5.32(2H, s), 6.14(1H, s), 6.6–7.5(4H, m) |
| I-1032 | 35–37 | 3.83(6H, s), 5.30(2H, s), 5.63(1H, s), 6.8–7.3(4H, m) |
| I-1132 | oily | 2.30(3H, s), 3.85(3H, s), 5.29(2H, s), 6.14(1H, s), 6.9–7.9(4H, m) |
| I-1142 | 58–60 | 3.87(6H, s), 5.30(2H, s), 5.63(1H, s), 7.0–7.7(4H, m) |
| I-1252 | 48–50 | 2.30(3H, s), 3.80(6H, s), 5.30(2H, s), 5.60(1H, s), 7.0–7.3(4H, m) |
| I-1344 | oily | 1.26(6H, d, J=6.3Hz), 2.27(3H, s), 5.24(1H, sept., J=6.3Hz), 5.25(2H, s) 6.05(1H, s), 7.26(4H, s) |
| I-1351 | oily | 1.31(3H, t, J=6.9Hz), 2.29(3H, s), 4.29(2H, q, J=6.9Hz), 5.27(2H, s), 6.11(1H, s), 7.28(4H, m) |
| I-1352 | oily | 2.30(3H, s), 3.84(3H, s), 5.29(2H, s), 6.14(1H, s), 7.2–7.5(4H, m) |
| I-1362 | 58–60 | 3.83(6H, s), 5.27(2H, s), 5.63(1H, s), 7.30(4H, s) |
| I-1454 | oily | 1.27(6H, d, J=6.3Hz), 2.28(3H, s), 5.27(1H, sept., J=6.3Hz), 5.28(2H, s), 6.08(1H, s), 6.7–7.6(4H, m) |
| I-1461 | 61–62 | 1.34(3H, t, J=6.9Hz), 2.32(3H, s), 4.32(2H, q, J=6.9Hz), 5.29(2H, s), 6.12(1H, s), 6.7–7.7(4H,m) |
| I-1462 | oily | 2.30(3H, s), 3.85(3H, s), 5.29(2H, s), 6.14(1H, s), 6.7–7.7(4H, m) |
| I-1472 | oily | 3.83(6H, s), 5.30(2H, s), 5.63(1H, s), 6.8–7.5(4H, m) |
| I-1572 | oily | 2.28(3H, s), 3.83(3H, s), 5.27(2H, s), 6.13(1H, s), 7.1–7.6(4H, m) |
| I-1582 | oily | 3.83(6H, s), 5.30(2H, s), 5.67(1H, s), 7.2–7.6(4H, m) |
| I-1692 | oily | 2.27(3H, s), 3.80(6H, s), 5.27(2H, s), 5.60(1H, s), 7.03(2H, d, J=8Hz), 7.30(2H, d, J=8Hz) |
| I-2007 | oily | 2.44(6H, s), 5.33(2H, s), 6.54(1H, s), 7.0–7.5(5H, m) |
| I-2014 | 55–57 | 1.30(3H, t, J=6.9Hz), 3.08(2H, q, J=6.9Hz), 5.34(2H, s), 6.70(1H, s), 7.0–7.6(5H, m) |

Formulation examples and test examples will now be described. Kinds of carriers (diluents) and additives to be used, as well as mixing ratios thereof and active ingredient contents therein may be modified in a broad range.

In each of the formulation examples, the term "parts" denotes "parts by weight" unless otherwise noted.

| Formulation Example 1 (wettable powder) | |
|---|---|
| Compound (I-372) | 50 parts |
| Lignin sulfonate | 5 parts |
| Alkyl sulfonate | 3 parts |
| Diatomaceous earth | 42 parts |

The above ingredients were mixed together and ground finely to form a wettable powder, which may be applied after diluted with water.

| Formulation Example 2 (emulsifiable concentrate) | |
|---|---|
| Compound (I-912) | 25 parts |
| Xylene | 65 parts |
| Polyoxyethylene alkyl aryl ether | 10 parts |

The above ingredients were homogeneously mixed to form an emulsifiable concentrate, which may be applied after diluted with water.

| Formulation Example 3 (granule) | |
|---|---|
| Compound (I-1362) | 8 parts |
| Bentonite | 40 parts |
| Clay | 45 parts |
| Lignin sulfonate | 7 parts |

The above ingredients were homogeneously mixed, blended with the addition of water and processed into granular form with an extrusion granulator to give granules.

Test Example 1 (Weed control test by foliage treatment)

Wettable powders were formulated as described in Formulation example 1 and diluted to a predetermined concentration. Each of the formulated test compound was applied at a rate of 500 g/10 a onto the foliage of each plant grown to the 1 to 2 leaf stage. The tested plants were pot-cultured redroot pigweed (*Amaranthus retroflexus*, AR), wild mustard (*Sinapis arvensis*, SA), sicklepod (*Cassia obtusifolia*, CO), black nightshade (*Solanum nigrum*, SN), velvetleaf (*Abutilon theophrasti*, AT), cleavers (*Galium aparine*, GA) and ivyleafspeedwell (*Veronica hederaefolia*, VH).

On the 14th day after the application, weed control effects were evaluated by the following criterion. Evaluation rating:
 1: less than 30%
 2: 30% to less than 70%
 3: 70% or more
The results are shown in Table 6.

TABLE 6

| No. | Dosage g/10a | AR | SA | CO | SN | AT | GA | VH |
|---|---|---|---|---|---|---|---|---|
| I-1 | 500 | 3 | 2 | 3 | 2 | 3 | 2 | 2 |
| I-3 | 500 | 3 | 2 | 3 | 2 | 2 | 3 | 3 |
| I-4 | 500 | 3 | 2 | 3 | 3 | 2 | 2 | 2 |
| I-5 | 500 | 2 | 2 | 2 | 2 | 2 | 2 | 3 |
| I-6 | 500 | 2 | 2 | 3 | 3 | 2 | 2 | 2 |
| I-7 | 500 | 3 | 2 | 2 | 2 | 2 | 2 | 2 |
| I-8 | 500 | 3 | 3 | 3 | 3 | 3 | 3 | 2 |
| I-9 | 500 | 3 | 3 | 3 | 3 | 2 | 3 | 2 |
| I-12 | 500 | 2 | 2 | 3 | 3 | 3 | 2 | 2 |
| I-15 | 500 | 2 | 2 | 3 | 3 | 3 | 2 | 2 |
| I-16 | 500 | 3 | 3 | 3 | 3 | 3 | 3 | 3 |
| I-20 | 500 | 3 | 3 | 3 | 3 | 2 | 3 | 2 |
| I-24 | 500 | 2 | 2 | 2 | 3 | 2 | 2 | 2 |
| I-25 | 500 | 2 | 2 | 3 | 2 | 2 | 2 | 2 |
| I-27 | 500 | 2 | 3 | 2 | 3 | 2 | 2 | 2 |
| I-29 | 500 | 3 | 3 | 3 | 3 | 3 | 3 | 3 |
| I-32 | 500 | 3 | 2 | 2 | 2 | 2 | 2 | 2 |
| I-34 | 500 | 2 | 2 | 2 | 3 | 2 | 2 | 2 |
| I-35 | 500 | 2 | 2 | 2 | 3 | 2 | 2 | 2 |
| I-36 | 500 | 3 | 2 | 2 | 2 | 3 | 2 | 2 |
| I-37 | 500 | 2 | 3 | 2 | 2 | 2 | 2 | 3 |
| I-38 | 500 | 2 | 3 | 2 | 3 | 2 | 2 | 2 |
| I-39 | 500 | 3 | 2 | 3 | 3 | 2 | 2 | 2 |
| I-41 | 500 | 3 | 3 | 2 | 2 | 2 | 2 | 2 |

TABLE 6-continued

| No. | Dosage g/10a | AR | SA | CO | SN | AT | GA | VH |
|---|---|---|---|---|---|---|---|---|
| I-43 | 500 | 2 | 2 | 3 | 3 | 2 | 2 | 2 |
| I-44 | 500 | 3 | 3 | 2 | 2 | 2 | 2 | 2 |
| I-45 | 500 | 2 | 3 | 2 | 2 | 3 | 2 | 2 |
| I-46 | 500 | 3 | 3 | 3 | 3 | 3 | 3 | 3 |
| I-47 | 500 | 3 | 3 | 2 | 3 | 3 | 3 | 3 |
| I-49 | 500 | 3 | 3 | 3 | 3 | 2 | 2 | 2 |
| I-50 | 500 | 3 | 2 | 2 | 3 | 2 | 3 | 2 |
| I-51 | 500 | 2 | 3 | 2 | 2 | 2 | 2 | 2 |
| I-53 | 500 | 3 | 3 | 2 | 2 | 2 | 3 | 2 |
| I-57 | 500 | 3 | 3 | 3 | 3 | 3 | 3 | 3 |
| I-58 | 500 | 3 | 3 | 3 | 3 | 3 | 2 | 2 |
| I-59 | 500 | 3 | 2 | 3 | 3 | 3 | 3 | 2 |
| I-60 | 500 | 3 | 3 | 2 | 2 | 2 | 3 | 2 |
| I-61 | 500 | 3 | 3 | 3 | 3 | 2 | 2 | 2 |
| I-62 | 500 | 2 | 3 | 2 | 2 | 2 | 2 | 2 |
| I-66 | 500 | 2 | 3 | 2 | 2 | 2 | 2 | 2 |
| I-67 | 500 | 2 | 2 | 2 | 3 | 2 | 2 | 2 |
| I-68 | 500 | 3 | 3 | 3 | 3 | 2 | 3 | 2 |
| I-173 | 500 | 1 | 3 | 3 | 3 | 3 | 2 | 3 |
| I-342 | 500 | 1 | 3 | 3 | 3 | 2 | 2 | 3 |
| I-343 | 500 | 1 | 3 | 2 | 2 | 2 | 2 | 2 |
| I-359 | 500 | 3 | 3 | 3 | 3 | 3 | 3 | 3 |
| I-361 | 500 | 3 | 3 | 3 | 3 | 3 | 2 | 2 |
| I-362 | 500 | 2 | 3 | 3 | 3 | 3 | 2 | 3 |
| I-371 | 500 | 3 | 3 | 3 | 3 | 3 | 3 | 3 |
| I-372 | 500 | 3 | 2 | 3 | 3 | 3 | 3 | 3 |
| I-464 | 500 | 2 | 3 | 2 | 2 | 2 | 2 | 2 |
| I-471 | 500 | 3 | 3 | 3 | 3 | 2 | 2 | 2 |
| I-472 | 500 | 2 | 3 | 3 | 3 | 2 | 3 | 3 |
| I-482 | 500 | 3 | 3 | 3 | 3 | 2 | 2 | 2 |
| I-581 | 500 | 3 | 2 | 3 | 3 | 2 | 2 | 2 |
| I-582 | 500 | 2 | 2 | 3 | 2 | 2 | 3 | 2 |
| I-592 | 500 | 3 | 3 | 3 | 3 | 3 | 3 | 3 |
| I-692 | 500 | 2 | 2 | 3 | 3 | 2 | 3 | 3 |
| I-702 | 500 | 3 | 3 | 3 | 3 | 3 | 2 | 3 |
| I-812 | 500 | 2 | 3 | 3 | 3 | 2 | 3 | 2 |
| I-911 | 500 | 3 | 3 | 3 | 3 | 3 | 2 | 2 |
| I-912 | 500 | 2 | 3 | 3 | 3 | 3 | 2 | 2 |
| I-922 | 500 | 3 | 3 | 3 | 3 | 3 | 3 | 3 |
| I-1021 | 500 | 2 | 2 | 3 | 3 | 2 | 2 | 2 |
| I-1022 | 500 | 2 | 2 | 3 | 2 | 2 | 2 | 2 |
| I-1032 | 500 | 3 | 3 | 3 | 3 | 3 | 3 | 3 |
| I-1132 | 500 | 3 | 2 | 3 | 3 | 2 | 3 | 2 |
| I-1142 | 500 | 3 | 3 | 3 | 3 | 3 | 3 | 3 |
| I-1252 | 500 | 2 | 3 | 3 | 3 | 2 | 3 | 2 |
| I-1351 | 500 | 3 | 3 | 3 | 3 | 2 | 2 | 2 |
| I-1352 | 500 | 3 | 3 | 3 | 3 | 3 | 3 | 3 |
| I-1362 | 500 | 3 | 3 | 3 | 3 | 3 | 3 | 3 |
| I-1454 | 500 | 2 | 3 | 3 | 3 | 3 | 2 | 2 |
| I-1461 | 500 | 3 | 3 | 3 | 2 | 2 | 2 | 2 |
| I-1462 | 500 | 2 | 2 | 3 | 2 | 2 | 2 | 2 |
| I-1472 | 500 | 3 | 3 | 3 | 3 | 3 | 3 | 3 |
| I-1572 | 500 | 2 | 2 | 3 | 2 | 2 | 2 | 2 |
| I-1582 | 500 | 3 | 3 | 3 | 3 | 3 | 3 | 3 |
| I-1692 | 500 | 3 | 3 | 3 | 3 | 3 | 3 | 2 |

AR: *Amaranthus retroflexus*
SA: *Sinapis arvensis*
CO: *Cassia obtusifolia*
SN: *Solanum nigrum*
AT: *Abutilon theophrasti*
GA: *Galium aparine*
VH: *Veronica hederaefolia*

Test Example 2 (Germination test)

In a 9 cm diameter Petri dish having the bottom covered with double sheets of filter paper, 6 ml of aqueous suspension of a test compound (containing 50 ppm of active ingredient) was poured and ten seeds of each weed were placed. The tested weeds were redroot pigweed (*Amaranthus retroflexus*, AR), black nightshade (*Solanum nigrum*, SN), wild chamomile (*Matricaria chamomilla*, MC), green foxtail (*Setaria viridis*, SV) and rice flatsedge (*Cyperus iria*, CI).

The seeds was allowed to germinate in a greenhouse at 28° C., and on the 14th day after the sowing, the inhibition of germination and the retarding of growth were visually observed and evaluated by the following 3-grade criterion.
Evaluation rating:
 1: less than 30%
 2: 30% to less than 70%
 3: 70% or more
The results are shown in Table 7.

TABLE 7

| No. | Dosage ppm | Herbage species | | | | |
|---|---|---|---|---|---|---|
| | | AR | SN | MC | SV | CI |
| I-3 | 50 | 3 | 2 | 2 | 2 | 2 |
| I-7 | 50 | 3 | 2 | 2 | 2 | 2 |
| I-8 | 50 | 3 | 2 | 2 | 2 | 2 |
| I-9 | 50 | 3 | 2 | 2 | 2 | 2 |
| I-16 | 50 | 3 | 2 | 2 | 2 | 2 |
| I-20 | 50 | 3 | 2 | 2 | 2 | 2 |
| I-24 | 50 | 3 | 1 | 1 | 3 | 3 |
| I-25 | 50 | 3 | 3 | 2 | 3 | 3 |
| I-29 | 50 | 3 | 2 | 2 | 3 | 3 |
| I-35 | 50 | 2 | 2 | 2 | 3 | 2 |
| I-36 | 50 | 3 | 2 | 2 | 2 | 2 |
| I-38 | 50 | 2 | 2 | 2 | 3 | 2 |
| I-41 | 50 | 3 | 2 | 2 | 3 | 2 |
| I-45 | 50 | 3 | 2 | 2 | 3 | 3 |
| I-46 | 50 | 3 | 3 | 3 | 3 | 3 |
| I-49 | 50 | 3 | 3 | 3 | 3 | 3 |
| I-53 | 50 | 3 | 2 | 2 | 3 | 2 |
| I-57 | 50 | 3 | 2 | 2 | 2 | 2 |
| I-58 | 50 | 3 | 2 | 2 | 3 | 3 |
| I-59 | 50 | 2 | 2 | 2 | 2 | 2 |
| I-61 | 50 | 3 | 2 | 2 | 2 | 2 |
| I-66 | 50 | 3 | 2 | 2 | 2 | 2 |
| I-68 | 50 | 3 | 2 | 2 | 3 | 3 |
| I-173 | 50 | 3 | 1 | 1 | 1 | 1 |
| I-343 | 50 | 3 | 1 | 1 | 3 | 3 |
| I-359 | 50 | 3 | 2 | 2 | 3 | 2 |
| I-361 | 50 | 3 | 3 | 3 | 3 | 3 |
| I-362 | 50 | 3 | 3 | 3 | 3 | 3 |
| I-371 | 50 | 3 | 1 | 1 | 3 | 3 |
| I-372 | 50 | 3 | 3 | 3 | 3 | 3 |
| I-471 | 50 | 3 | 2 | 2 | 2 | 3 |
| I-472 | 50 | 3 | 2 | 2 | 2 | 2 |
| I-482 | 50 | 3 | 2 | 2 | 3 | 3 |
| I-581 | 50 | 3 | 2 | 2 | 2 | 2 |
| I-592 | 50 | 3 | 2 | 3 | 3 | 3 |
| I-812 | 50 | 3 | 2 | 2 | 3 | 3 |
| I-912 | 50 | 3 | 2 | 2 | 3 | 3 |
| I-922 | 50 | 3 | 2 | 2 | 3 | 3 |
| I-1021 | 50 | 3 | 3 | 3 | 3 | 3 |
| I-1032 | 50 | 3 | 3 | 3 | 3 | 3 |
| I-1142 | 50 | 3 | 2 | 2 | 2 | 3 |
| I-1252 | 50 | 3 | 2 | 2 | 3 | 3 |
| I-1351 | 50 | 3 | 2 | 2 | 2 | 2 |
| I-1352 | 50 | 3 | 2 | 3 | 3 | 2 |
| I-1362 | 50 | 3 | 2 | 3 | 3 | 3 |
| I-1454 | 50 | 2 | 2 | 3 | 2 | 2 |
| I-1461 | 50 | 3 | 2 | 2 | 2 | 2 |
| I-1462 | 50 | 3 | 2 | 2 | 3 | 3 |
| I-1472 | 50 | 3 | 3 | 3 | 3 | 3 |
| I-1582 | 50 | 3 | 2 | 2 | 3 | 3 |
| I-1692 | 50 | 3 | 2 | 2 | 3 | 3 |

AR: *Amaranthus retroflexus*
SN: *Solanum nigrum*
MC: *Matricaria chamomilla*
SV: *Setaria viridis*
CI: *Cyperus iria*

What is claimed is:

1. A herbicidal composition comprising a herbicidally effective amount of a 2-benzyloxypyrimidine derivative represented by the formula (I):

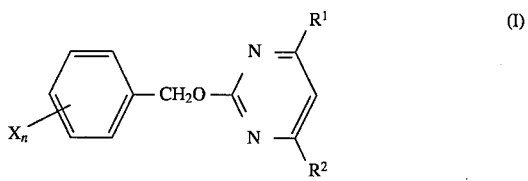

wherein $R^1$ and $R^2$ are each independently H, a halogen, hydroxyl, $C_1$–$C_4$ alkyl, $C_1$–$C_4$ haloalkyl, $C_3$–$C_5$ alkenyl, $C_3$–$C_5$ alkynyl, $C_1$–$C_4$ alkoxy, $C_1$–$C_4$ haloalkoxy, $C_3$–$C_5$ alkenyloxy, $C_3$–$C_5$ alkynyloxy, $C_1$–$C_4$ alkylthio, or phenyl;

n is an integer of 0 to 5; and each X which may be identical or different if n is greater than 1, is a halogen, $C_1$–$C_4$ alkyl, $C_1$–$C_4$ haloalkyl, $C_1$–$C_4$ alkoxy, $C_1$–$C_4$ alkylthio, $C_7$–$C_9$ aralkyloxy, phenyl, hydroxymethyl, hydroxycarbonyl, $C_1$–$C_4$ alkoxycarbonyl, or nitro, and an adjuvant.

2. A herbicidal composition according to claim 1, wherein $R^1$ and $R^2$ are each independently methyl or methoxy, at least one of $R^1$ and $R^2$ is methoxy, n is 0 to 2, and X is a halogen.

3. A 2-benzyloxypyrimidine derivative represented by the formula (I):

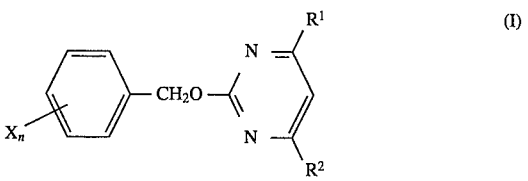

wherein $R^1$ and $R^2$ are each independently H, a halogen, hydroxyl, $C_1$–$C_4$ alkyl, $C_1$–$C_4$ haloalkyl, $C_3$–$C_5$ alkenyl, $C_3$–$C_5$ alkynyl, $C_1$–$C_4$ alkoxy, $C_1$–$C_4$ haloalkoxy, $C_3$–$C_5$ alkenyloxy, $C_3$–$C_5$ alkynyloxy, $C_1$–$C_4$ alkylthio or phenyl;

n is an integer of 0 to 5; and each X which may be identical or different if n is greater than 1, is a halogen, $C_1$–$C_4$ alkyl, $C_1$–$C_4$ haloalkyl, $C_1$–$C_4$ alkoxy, $C_1$–$C_4$ alkylthio, $C_7$–$C_9$ aralkyloxy, phenyl, hydroxymethyl, hydroxycarbonyl, $C_1$–$C_4$ alkoxycarbonyl, or nitro, with a proviso that 2-benzyloxypyrimidine, 2-benzyloxy-4-ethoxypyrimidine and 2-benzyloxy-4,6-dimethylpyrimidine are excluded.

4. A 2-benzyloxypyrimidine derivative according to claim 3, wherein $R^1$ and $R^2$ are each independently methyl or methoxy, at least one of $R^1$ and $R^2$ is methoxy, n is 0 to 2, and X is a halogen.

* * * * *